US011311376B2

(12) United States Patent
Fung et al.

(10) Patent No.: US 11,311,376 B2
(45) Date of Patent: Apr. 26, 2022

(54) LOW PROFILE PROSTHETIC MITRAL VALVE

(71) Applicant: Neovasc Tiara Inc., Richmond (CA)

(72) Inventors: Eric Soun-Sang Fung, Vancouver (CA); Karen Tsoek-Ji Wong, Richmond (CA); Ephraim Ben-Abraham, Rochester, MN (US)

(73) Assignee: Neovasc Tiara Inc., Richmond (CA)

( * ) Notice: Subject to any disclaimer, the term of this patent is extended or adjusted under 35 U.S.C. 154(b) by 0 days.

(21) Appl. No.: 16/906,782

(22) Filed: Jun. 19, 2020

(65) Prior Publication Data

US 2020/0397570 A1 Dec. 24, 2020

Related U.S. Application Data

(60) Provisional application No. 62/864,008, filed on Jun. 20, 2019.

(51) Int. Cl.
*A61F 2/24* (2006.01)

(52) U.S. Cl.
CPC ............ *A61F 2/2418* (2013.01); *A61F 2/243* (2013.01); *A61F 2/2409* (2013.01); *A61F 2220/0008* (2013.01); *A61F 2230/0054* (2013.01); *A61F 2230/0067* (2013.01); *A61F 2250/0039* (2013.01)

(58) Field of Classification Search
CPC ...................... A61F 2/418; A61F 2/243; A61F 2250/00398; A61F 2220/0008; A61F 2230/0054; A61F 2/2409; A61F 2230/0067
See application file for complete search history.

(56) References Cited

U.S. PATENT DOCUMENTS

| 2,967,856 A | 1/1961 | Coover, Jr. et al. |
| 2001/0021872 A1 | 9/2001 | Bailey et al. |
| 2007/0142906 A1 | 6/2007 | Figulla et al. |

(Continued)

FOREIGN PATENT DOCUMENTS

| CA | 2874219 C | 7/2020 |
| DE | 10103955 B4 | 11/2001 |

(Continued)

OTHER PUBLICATIONS

"International Application Serial No. PCT/US2020/038726, International Search Report dated Nov. 6, 2020", 4 pgs.

(Continued)

*Primary Examiner* — Suba Ganesan
(74) *Attorney, Agent, or Firm* — Schwegman Lundberg & Woessner, P.A.

(57) ABSTRACT

A low-profile prosthetic valve for treating a native valve includes a radially expandable frame having an expanded configuration and a collapsed configuration. The atrial end of the prosthetic valve forms a flared shape that engages an atrial surface of the native valve. The flare shape flares downward toward a ventricle of the native valve when initially expanded followed by inversion of the flared shape to form a tapered shape tapering toward the ventricle and flaring toward the atrium of the native valve when fully expanded. The prosthetic valve also has a plurality of prosthetic valve leaflets that open and close to control fluid flow through the prosthetic valve.

18 Claims, 29 Drawing Sheets

(56) References Cited

U.S. PATENT DOCUMENTS

| | | |
|---|---|---|
| 2009/0276040 A1 | 11/2009 | Rowe et al. |
| 2013/0172992 A1* | 7/2013 | Gross ............... A61B 17/068 623/2.11 |
| 2013/0325114 A1 | 12/2013 | Mclean et al. |
| 2014/0052237 A1 | 2/2014 | Lane et al. |
| 2014/0194983 A1* | 7/2014 | Kovalsky ............. A61F 2/2418 623/2.38 |
| 2017/0281343 A1* | 10/2017 | Christianson ......... A61F 2/2436 |
| 2018/0078370 A1 | 3/2018 | Kovalsky et al. |

FOREIGN PATENT DOCUMENTS

| | | |
|---|---|---|
| DE | 10033858 B4 | 1/2002 |
| DE | 102006052564 B3 | 12/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 114387981 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335683 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1684671 A1 | 8/2006 |
| EP | 1519695 B1 | 9/2006 |
| EP | 1444993 B1 | 10/2006 |
| EP | 1117350 B1 | 11/2006 |
| EP | 1212011 B1 | 11/2006 |
| EP | 1261294 B1 | 11/2006 |
| EP | 1318775 B1 | 11/2006 |
| EP | 1429690 B1 | 11/2006 |
| EP | 1173111 B1 | 12/2006 |
| EP | 1239795 B1 | 12/2006 |
| EP | 1299049 B1 | 12/2006 |
| EP | 1487382 B1 | 12/2006 |
| EP | 1112044 B1 | 1/2007 |
| EP | 1482997 B1 | 1/2007 |
| EP | 1117352 B1 | 2/2007 |
| EP | 1128849 B1 | 2/2007 |
| EP | 1392666 B1 | 2/2007 |
| EP | 1474077 B1 | 2/2007 |
| EP | 1251805 B1 | 3/2007 |
| EP | 1117334 B1 | 4/2007 |
| EP | 1263484 B1 | 5/2007 |
| EP | 1313410 B1 | 5/2007 |
| EP | 1370200 B1 | 5/2007 |
| EP | 1560526 B1 | 6/2007 |
| EP | 1173117 B1 | 7/2007 |
| EP | 1434615 B1 | 7/2007 |
| EP | 1465546 B1 | 7/2007 |
| EP | 1499366 B1 | 7/2007 |
| EP | 1225948 B1 | 8/2007 |
| EP | 1519962 B1 | 9/2007 |
| EP | 1337285 B1 | 10/2007 |
| EP | 1112042 B1 | 11/2007 |
| EP | 114882181 | 11/2007 |
| EP | 1330189 B1 | 12/2007 |
| EP | 1489996 B1 | 12/2007 |
| EP | 114388281 | 12/2007 |
| EP | 1296618 B1 | 1/2008 |
| EP | 1401356 B1 | 1/2008 |
| EP | 1629795 B1 | 1/2008 |
| EP | 1128786 B1 | 2/2008 |
| EP | 1616532 B1 | 2/2008 |
| EP | 1289447 B1 | 3/2008 |
| EP | 1895942 A2 | 3/2008 |
| EP | 1115353 B1 | 5/2008 |
| EP | 1330190 B1 | 5/2008 |
| EP | 1383448 B1 | 6/2008 |
| EP | 1251804 B1 | 7/2008 |
| EP | 1294310 B1 | 7/2008 |
| EP | 1313409 B1 | 7/2008 |
| EP | 1395202 B1 | 7/2008 |

(56) References Cited

FOREIGN PATENT DOCUMENTS

| | | |
|---|---|---|
| EP | 1395204 B1 | 7/2008 |
| EP | 1395205 B1 | 7/2008 |
| EP | 1423066 B1 | 7/2008 |
| EP | 1560545 B1 | 7/2008 |
| EP | 1605871 B1 | 7/2008 |
| EP | 1671608 B1 | 7/2008 |
| EP | 1690515 B1 | 7/2008 |
| EP | 1180987 B1 | 8/2008 |
| EP | 1337386 B1 | 8/2008 |
| EP | 1492579 B1 | 9/2008 |
| EP | 1524942 B1 | 9/2008 |
| EP | 1627091 B1 | 9/2008 |
| EP | 1827577 B1 | 9/2008 |
| EP | 1259195 B1 | 10/2008 |
| EP | 1704834 B1 | 10/2008 |
| EP | 1498086 B1 | 11/2008 |
| EP | 1622548 B1 | 11/2008 |
| EP | 114683581 | 11/2008 |
| EP | 1235537 B1 | 12/2008 |
| EP | 1237509 B1 | 12/2008 |
| EP | 1355590 B1 | 12/2008 |
| EP | 1455680 B1 | 12/2008 |
| EP | 1472995 B1 | 12/2008 |
| EP | 1513474 B1 | 12/2008 |
| EP | 1562522 B1 | 12/2008 |
| EP | 1620042 B1 | 12/2008 |
| EP | 1690514 B1 | 12/2008 |
| EP | 1258232 B1 | 1/2009 |
| EP | 1420723 B1 | 1/2009 |
| EP | 1570809 B1 | 1/2009 |
| EP | 1395182 B1 | 2/2009 |
| EP | 1408882 B1 | 2/2009 |
| EP | 1482868 B1 | 2/2009 |
| EP | 1255510 B3 | 3/2009 |
| EP | 1330213 B1 | 3/2009 |
| EP | 1429651 B1 | 3/2009 |
| EP | 1610727 B1 | 4/2009 |
| EP | 1617788 B1 | 4/2009 |
| EP | 1634547 B1 | 4/2009 |
| EP | 1790318 B1 | 4/2009 |
| EP | 2040645 A1 | 4/2009 |
| EP | 1250165 B1 | 5/2009 |
| EP | 1842508 B1 | 6/2009 |
| EP | 1968482 B1 | 6/2009 |
| EP | 2072027 A1 | 6/2009 |
| EP | 1343438 B1 | 7/2009 |
| EP | 1406608 B1 | 7/2009 |
| EP | 1509256 B1 | 7/2009 |
| EP | 1626681 B1 | 7/2009 |
| EP | 1723935 B1 | 7/2009 |
| EP | 1803420 B1 | 7/2009 |
| EP | 2073755 A2 | 7/2009 |
| EP | 1401359 B1 | 8/2009 |
| EP | 1411865 B1 | 8/2009 |
| EP | 1485033 B1 | 8/2009 |
| EP | 1581120 B1 | 8/2009 |
| EP | 1620040 B1 | 8/2009 |
| EP | 1684667 B1 | 8/2009 |
| EP | 1872743 B1 | 8/2009 |
| EP | 1100378 B1 | 9/2009 |
| EP | 1198203 B1 | 9/2009 |
| EP | 1370201 B1 | 9/2009 |
| EP | 1408850 B1 | 9/2009 |
| EP | 1472996 B1 | 9/2009 |
| EP | 1478364 B1 | 9/2009 |
| EP | 1653888 B1 | 9/2009 |
| EP | 1785154 B1 | 9/2009 |
| EP | 1881804 B1 | 9/2009 |
| EP | 1903991 B1 | 9/2009 |
| EP | 1418865 B1 | 10/2009 |
| EP | 1561437 B1 | 10/2009 |
| EP | 1615595 B1 | 10/2009 |
| EP | 1353612 B1 | 11/2009 |
| EP | 1348406 B1 | 12/2009 |
| EP | 1370202 B1 | 12/2009 |
| EP | 1603492 B1 | 12/2009 |
| EP | 1670364 B1 | 12/2009 |
| EP | 1759663 B1 | 12/2009 |
| EP | 1994887 B1 | 12/2009 |
| EP | 1615593 B1 | 1/2010 |
| EP | 1643938 B1 | 1/2010 |
| EP | 1863402 B1 | 1/2010 |
| EP | 1943942 B1 | 1/2010 |
| EP | 2010101 B1 | 1/2010 |
| EP | 2081518 B1 | 1/2010 |
| EP | 1703865 B1 | 2/2010 |
| EP | 1276437 B1 | 3/2010 |
| EP | 1276439 B1 | 3/2010 |
| EP | 1411867 B1 | 3/2010 |
| EP | 1458313 B1 | 3/2010 |
| EP | 1520519 B1 | 3/2010 |
| EP | 1648340 B1 | 3/2010 |
| EP | 1682048 B1 | 3/2010 |
| EP | 1773239 B1 | 3/2010 |
| EP | 1935377 B1 | 3/2010 |
| EP | 1994912 B1 | 3/2010 |
| EP | 1154738 B1 | 4/2010 |
| EP | 1531762 B1 | 4/2010 |
| EP | 1600178 B1 | 4/2010 |
| EP | 1626682 B1 | 4/2010 |
| EP | 1511445 B1 | 5/2010 |
| EP | 1198213 B1 | 6/2010 |
| EP | 1250097 B1 | 6/2010 |
| EP | 1272249 B1 | 6/2010 |
| EP | 1978895 B1 | 6/2010 |
| EP | 1572033 B1 | 7/2010 |
| EP | 1968491 B1 | 7/2010 |
| EP | 2019652 B1 | 7/2010 |
| EP | 1610722 B1 | 8/2010 |
| EP | 1682047 B1 | 8/2010 |
| EP | 1952772 B1 | 8/2010 |
| EP | 1427356 B1 | 9/2010 |
| EP | 1631218 B1 | 9/2010 |
| EP | 1765224 B1 | 9/2010 |
| EP | 1871290 B1 | 9/2010 |
| EP | 1895288 B1 | 9/2010 |
| EP | 1895913 B1 | 9/2010 |
| EP | 2014257 B1 | 9/2010 |
| EP | 1176913 B1 | 10/2010 |
| EP | 1178758 B1 | 10/2010 |
| EP | 1248579 B1 | 10/2010 |
| EP | 1913899 B1 | 10/2010 |
| EP | 1259193 B1 | 11/2010 |
| EP | 1928357 B1 | 11/2010 |
| EP | 1968660 B1 | 11/2010 |
| EP | 2249711 A2 | 11/2010 |
| EP | 1408895 B1 | 12/2010 |
| EP | 1465554 B1 | 12/2010 |
| EP | 1732473 B1 | 12/2010 |
| EP | 1768610 B1 | 12/2010 |
| EP | 1827314 B1 | 12/2010 |
| EP | 1940321 B1 | 12/2010 |
| EP | 1964532 B1 | 12/2010 |
| EP | 2078498 B1 | 12/2010 |
| EP | 1600182 B1 | 1/2011 |
| EP | 1617789 B1 | 1/2011 |
| EP | 1663332 B1 | 1/2011 |
| EP | 2147659 B1 | 1/2011 |
| EP | 2268231 A2 | 1/2011 |
| EP | 2273951 A1 | 1/2011 |
| EP | 1187582 B1 | 2/2011 |
| EP | 1450733 B1 | 2/2011 |
| EP | 1803421 B1 | 2/2011 |
| EP | 1833425 B1 | 2/2011 |
| EP | 2029053 B1 | 2/2011 |
| EP | 2068770 B1 | 2/2011 |
| EP | 1441784 B1 | 3/2011 |
| EP | 1534177 B1 | 3/2011 |
| EP | 1893132 B1 | 3/2011 |
| EP | 1951153 B1 | 3/2011 |
| EP | 2289467 A1 | 3/2011 |
| EP | 2299938 A2 | 3/2011 |
| EP | 1359978 B1 | 4/2011 |
| EP | 1667750 B1 | 4/2011 |

(56) References Cited

FOREIGN PATENT DOCUMENTS

| | | | |
|---|---|---|---|
| EP | 1718249 B1 | 4/2011 |
| EP | 1903989 B1 | 4/2011 |
| EP | 2018122 B1 | 4/2011 |
| EP | 1610728 B1 | 5/2011 |
| EP | 2105110 B1 | 5/2011 |
| EP | 1347717 B1 | 6/2011 |
| EP | 2331018 A1 | 6/2011 |
| EP | 1347791 B1 | 7/2011 |
| EP | 1862128 B1 | 7/2011 |
| EP | 2120795 B1 | 7/2011 |
| EP | 2229920 B1 | 7/2011 |
| EP | 1637087 B1 | 8/2011 |
| EP | 2153799 B1 | 8/2011 |
| EP | 2247263 B1 | 8/2011 |
| EP | 2358307 A1 | 8/2011 |
| EP | 1441672 B1 | 9/2011 |
| EP | 1625832 B1 | 9/2011 |
| EP | 2173279 B1 | 9/2011 |
| EP | 2367505 A1 | 9/2011 |
| EP | 2160150 B1 | 10/2011 |
| EP | 2370138 A2 | 10/2011 |
| EP | 1626679 B1 | 11/2011 |
| EP | 1719476 B1 | 11/2011 |
| EP | 1928355 B1 | 11/2011 |
| EP | 2237747 B1 | 11/2011 |
| EP | 2381895 A2 | 11/2011 |
| EP | 2389121 A1 | 11/2011 |
| EP | 1572031 B1 | 12/2011 |
| EP | 1603493 B1 | 12/2011 |
| EP | 1945109 B1 | 12/2011 |
| EP | 1998688 B1 | 12/2011 |
| EP | 2393442 A2 | 12/2011 |
| EP | 2395944 A1 | 12/2011 |
| EP | 1443877 B1 | 1/2012 |
| EP | 2400922 A1 | 1/2012 |
| EP | 1281375 B1 | 2/2012 |
| EP | 1699501 B1 | 2/2012 |
| EP | 1788984 B1 | 2/2012 |
| EP | 1833415 B1 | 2/2012 |
| EP | 1952785 B1 | 2/2012 |
| EP | 2055266 B1 | 2/2012 |
| EP | 2205184 B1 | 2/2012 |
| EP | 2416736 A1 | 2/2012 |
| EP | 1337188 B1 | 3/2012 |
| EP | 1443974 B1 | 3/2012 |
| EP | 1542623 B1 | 3/2012 |
| EP | 1942835 B1 | 3/2012 |
| EP | 2074964 B1 | 3/2012 |
| EP | 2244661 B1 | 3/2012 |
| EP | 2273928 B1 | 3/2012 |
| EP | 2427144 A1 | 3/2012 |
| EP | 2429455 A1 | 3/2012 |
| EP | 1401336 B1 | 4/2012 |
| EP | 1749544 B1 | 4/2012 |
| EP | 2119417 B1 | 4/2012 |
| EP | 2152330 B1 | 4/2012 |
| EP | 2231069 B1 | 4/2012 |
| EP | 2437688 A1 | 4/2012 |
| EP | 2020958 B1 | 5/2012 |
| EP | 2192875 B1 | 5/2012 |
| EP | 2218425 B1 | 5/2012 |
| EP | 2445450 A1 | 5/2012 |
| EP | 1411847 B1 | 6/2012 |
| EP | 1727499 B1 | 6/2012 |
| EP | 2082690 B1 | 6/2012 |
| EP | 1740747 B1 | 7/2012 |
| EP | 1861044 B1 | 7/2012 |
| EP | 2052699 B1 | 7/2012 |
| EP | 2470121 A2 | 7/2012 |
| EP | 2471492 A1 | 7/2012 |
| EP | 1887975 B1 | 8/2012 |
| EP | 2000116 B1 | 8/2012 |
| EP | 2222247 B1 | 8/2012 |
| EP | 2486894 A1 | 8/2012 |
| EP | 1605870 B1 | 9/2012 |
| EP | 1887980 B1 | 9/2012 |
| EP | 2497445 A1 | 9/2012 |
| EP | 1740126 B1 | 10/2012 |
| EP | 1865889 B1 | 10/2012 |
| EP | 2033593 B1 | 10/2012 |
| EP | 2124824 B1 | 10/2012 |
| EP | 2139431 B1 | 10/2012 |
| EP | 2506777 A1 | 10/2012 |
| EP | 2512952 A2 | 10/2012 |
| EP | 1430853 B1 | 11/2012 |
| EP | 1928512 B1 | 11/2012 |
| EP | 2008615 B1 | 11/2012 |
| EP | 2088965 B1 | 11/2012 |
| EP | 2522307 A1 | 11/2012 |
| EP | 1557138 B1 | 12/2012 |
| EP | 1924221 B1 | 12/2012 |
| EP | 2023859 B1 | 12/2012 |
| EP | 2250970 B1 | 12/2012 |
| EP | 2285317 B1 | 12/2012 |
| EP | 2537486 A1 | 12/2012 |
| EP | 1494731 B1 | 1/2013 |
| EP | 1610752 B1 | 1/2013 |
| EP | 1796597 B1 | 1/2013 |
| EP | 1919397 B1 | 1/2013 |
| EP | 1942834 B1 | 1/2013 |
| EP | 2015709 B1 | 1/2013 |
| EP | 2079400 B1 | 1/2013 |
| EP | 2238947 B1 | 1/2013 |
| EP | 2241287 B1 | 1/2013 |
| EP | 2359774 B1 | 1/2013 |
| EP | 2538878 A1 | 1/2013 |
| EP | 2538883 A1 | 1/2013 |
| EP | 1512383 B1 | 2/2013 |
| EP | 1578474 B1 | 2/2013 |
| EP | 1648339 B1 | 2/2013 |
| EP | 1750622 B1 | 2/2013 |
| EP | 1994482 B1 | 2/2013 |
| EP | 2250975 B1 | 2/2013 |
| EP | 2257242 B1 | 2/2013 |
| EP | 2265225 B1 | 2/2013 |
| EP | 2558032 A1 | 2/2013 |
| EP | 1659992 B1 | 3/2013 |
| EP | 1701668 B1 | 3/2013 |
| EP | 2151216 B1 | 3/2013 |
| EP | 2340075 B1 | 3/2013 |
| EP | 2568924 A2 | 3/2013 |
| EP | 1781183 B1 | 4/2013 |
| EP | 1786367 B1 | 4/2013 |
| EP | 1850795 B1 | 4/2013 |
| EP | 1861041 B1 | 4/2013 |
| EP | 2319458 B1 | 4/2013 |
| EP | 2526898 B1 | 4/2013 |
| EP | 2537487 B1 | 4/2013 |
| EP | 1901682 B1 | 5/2013 |
| EP | 1951166 B1 | 5/2013 |
| EP | 1994913 B1 | 5/2013 |
| EP | 2231070 B1 | 5/2013 |
| EP | 2401970 B1 | 5/2013 |
| EP | 2409651 B1 | 5/2013 |
| EP | 2594230 A1 | 5/2013 |
| EP | 1694246 B1 | 6/2013 |
| EP | 1948087 B1 | 6/2013 |
| EP | 2135559 B1 | 6/2013 |
| EP | 1115335 B1 | 7/2013 |
| EP | 1663339 B1 | 7/2013 |
| EP | 1864687 B1 | 7/2013 |
| EP | 1977719 B1 | 7/2013 |
| EP | 2111337 B1 | 7/2013 |
| EP | 2298237 B1 | 7/2013 |
| EP | 2309949 B1 | 7/2013 |
| EP | 2608741 A2 | 7/2013 |
| EP | 2611389 A2 | 7/2013 |
| EP | 1599151 B1 | 8/2013 |
| EP | 1761211 B1 | 8/2013 |
| EP | 2047871 B1 | 8/2013 |
| EP | 2142144 B1 | 8/2013 |
| EP | 2150206 B1 | 8/2013 |
| EP | 2319459 B1 | 8/2013 |
| EP | 2397108 B1 | 8/2013 |

(56) References Cited

FOREIGN PATENT DOCUMENTS

| | | |
|---|---|---|
| EP | 2623068 A1 | 8/2013 |
| EP | 1758523 B1 | 9/2013 |
| EP | 1545392 B1 | 10/2013 |
| EP | 1638627 B1 | 10/2013 |
| EP | 1779868 B1 | 10/2013 |
| EP | 2073756 B1 | 10/2013 |
| EP | 2111190 B1 | 10/2013 |
| EP | 1848375 B1 | 11/2013 |
| EP | 1928356 B1 | 11/2013 |
| EP | 1933766 B1 | 11/2013 |
| EP | 2109417 B1 | 11/2013 |
| EP | 2194925 B1 | 11/2013 |
| EP | 2387977 B1 | 11/2013 |
| EP | 2476394 B1 | 11/2013 |
| EP | 2529701 B1 | 11/2013 |
| EP | 1945142 B1 | 12/2013 |
| EP | 2387972 B1 | 12/2013 |
| EP | 2477555 B1 | 12/2013 |
| EP | 2670349 A2 | 12/2013 |
| EP | 2117476 B1 | 1/2014 |
| EP | 2526895 B1 | 1/2014 |
| EP | 2526899 B1 | 1/2014 |
| EP | 2529696 B1 | 1/2014 |
| EP | 2529697 B1 | 1/2014 |
| EP | 2529698 B1 | 1/2014 |
| EP | 2529699 B1 | 1/2014 |
| EP | 2679198 A1 | 1/2014 |
| EP | 1395214 B1 | 2/2014 |
| EP | 1499266 B1 | 2/2014 |
| EP | 1838241 B1 | 2/2014 |
| EP | 2520250 B1 | 2/2014 |
| EP | 2526977 B1 | 2/2014 |
| EP | 2693985 A1 | 2/2014 |
| EP | 2699302 A2 | 2/2014 |
| EP | 1629794 B1 | 3/2014 |
| EP | 1919398 B1 | 3/2014 |
| EP | 2099508 B1 | 3/2014 |
| EP | 2399549 B1 | 3/2014 |
| EP | 2422823 B1 | 3/2014 |
| EP | 2706958 A1 | 3/2014 |
| EP | 1804860 B1 | 4/2014 |
| EP | 1926455 B1 | 4/2014 |
| EP | 2081519 B1 | 4/2014 |
| EP | 2117477 B1 | 4/2014 |
| EP | 2405966 B1 | 4/2014 |
| EP | 2420205 B1 | 4/2014 |
| EP | 2593048 B1 | 4/2014 |
| EP | 2713894 A2 | 4/2014 |
| EP | 2713955 A2 | 4/2014 |
| EP | 2723273 A2 | 4/2014 |
| EP | 1499265 B1 | 5/2014 |
| EP | 1594569 B1 | 5/2014 |
| EP | 2029056 B1 | 5/2014 |
| EP | 2257243 B1 | 5/2014 |
| EP | 1791500 B1 | 6/2014 |
| EP | 2073753 B1 | 6/2014 |
| EP | 2306933 B1 | 6/2014 |
| EP | 2331017 B1 | 6/2014 |
| EP | 2337522 B1 | 6/2014 |
| EP | 2389897 B1 | 6/2014 |
| EP | 2606723 B1 | 6/2014 |
| EP | 2739250 A1 | 6/2014 |
| EP | 1487350 B1 | 7/2014 |
| EP | 1977718 B1 | 7/2014 |
| EP | 2117469 B1 | 7/2014 |
| EP | 2124826 B1 | 7/2014 |
| EP | 2258316 B1 | 7/2014 |
| EP | 2747708 A1 | 7/2014 |
| EP | 2750630 A1 | 7/2014 |
| EP | 2750631 A1 | 7/2014 |
| EP | 1667604 B1 | 8/2014 |
| EP | 1786368 B1 | 8/2014 |
| EP | 2211779 B1 | 8/2014 |
| EP | 2217174 B1 | 8/2014 |
| EP | 2293740 B1 | 8/2014 |
| EP | 2367504 B1 | 8/2014 |
| EP | 2453942 B1 | 8/2014 |
| EP | 2475328 B1 | 8/2014 |
| EP | 2545884 B1 | 8/2014 |
| EP | 2571460 B1 | 8/2014 |
| EP | 2763708 A2 | 8/2014 |
| EP | 2765954 A1 | 8/2014 |
| EP | 1935378 B1 | 9/2014 |
| EP | 2246011 B1 | 9/2014 |
| EP | 2422749 B1 | 9/2014 |
| EP | 2531139 B1 | 9/2014 |
| EP | 2609893 B1 | 9/2014 |
| EP | 2777616 A1 | 9/2014 |
| EP | 2779945 A1 | 9/2014 |
| EP | 1853199 B1 | 10/2014 |
| EP | 2133039 B1 | 10/2014 |
| EP | 2549955 B1 | 10/2014 |
| EP | 2549956 B1 | 10/2014 |
| EP | 2651335 B1 | 10/2014 |
| EP | 2785281 A1 | 10/2014 |
| EP | 2793743 A1 | 10/2014 |
| EP | 2793752 A1 | 10/2014 |
| EP | 2049721 B1 | 11/2014 |
| EP | 2142143 B1 | 11/2014 |
| EP | 2229921 B1 | 11/2014 |
| EP | 2288403 B1 | 11/2014 |
| EP | 2415421 B1 | 11/2014 |
| EP | 1551274 B1 | 12/2014 |
| EP | 1768735 B1 | 12/2014 |
| EP | 1959865 B1 | 12/2014 |
| EP | 2077718 B1 | 12/2014 |
| EP | 2303185 B1 | 12/2014 |
| EP | 2334857 B1 | 12/2014 |
| EP | 2365840 B1 | 12/2014 |
| EP | 2420207 B1 | 12/2014 |
| EP | 2422750 B1 | 12/2014 |
| EP | 2707073 B1 | 12/2014 |
| EP | 1768630 B1 | 1/2015 |
| EP | 2254515 B1 | 1/2015 |
| EP | 2641569 B1 | 1/2015 |
| EP | 2709559 B1 | 1/2015 |
| EP | 2825203 A1 | 1/2015 |
| EP | 1903990 B1 | 2/2015 |
| EP | 2255753 B1 | 2/2015 |
| EP | 2335649 B1 | 2/2015 |
| EP | 2522308 B1 | 2/2015 |
| EP | 2591754 B1 | 2/2015 |
| EP | 2835112 A1 | 2/2015 |
| EP | 1861045 B1 | 3/2015 |
| EP | 2029057 B1 | 3/2015 |
| EP | 2193761 B1 | 3/2015 |
| EP | 2379010 B1 | 3/2015 |
| EP | 2416737 B1 | 3/2015 |
| EP | 1791495 B1 | 4/2015 |
| EP | 2298252 B1 | 4/2015 |
| EP | 2536359 B1 | 4/2015 |
| EP | 2538879 B1 | 4/2015 |
| EP | 2609894 B1 | 4/2015 |
| EP | 2693984 B1 | 4/2015 |
| EP | 2712633 B1 | 4/2015 |
| EP | 2747707 B1 | 4/2015 |
| EP | 2862546 A1 | 4/2015 |
| EP | 2863842 A1 | 4/2015 |
| EP | 1465555 B1 | 5/2015 |
| EP | 1924224 B1 | 5/2015 |
| EP | 1992369 B1 | 5/2015 |
| EP | 2410947 B1 | 5/2015 |
| EP | 2484311 B1 | 5/2015 |
| EP | 2654616 B1 | 5/2015 |
| EP | 2866741 A1 | 5/2015 |
| EP | 1646332 B1 | 6/2015 |
| EP | 2745805 B1 | 6/2015 |
| EP | 2749254 B1 | 6/2015 |
| EP | 2877123 A2 | 6/2015 |
| EP | 2882374 A1 | 6/2015 |
| EP | 2884906 A1 | 6/2015 |
| EP | 1729685 B1 | 7/2015 |
| EP | 1976439 B1 | 7/2015 |
| EP | 2068767 B1 | 7/2015 |

(56) References Cited

FOREIGN PATENT DOCUMENTS

| | | | |
|---|---|---|---|
| EP | 2068769 | B1 | 7/2015 |
| EP | 2444031 | B1 | 7/2015 |
| EP | 2455041 | B1 | 7/2015 |
| EP | 2498719 | B1 | 7/2015 |
| EP | 2558030 | B1 | 7/2015 |
| EP | 2752209 | B1 | 7/2015 |
| EP | 2892467 | A1 | 7/2015 |
| EP | 1702247 | B1 | 8/2015 |
| EP | 1729688 | B1 | 8/2015 |
| EP | 1887979 | B1 | 8/2015 |
| EP | 2032079 | B1 | 8/2015 |
| EP | 2219558 | B1 | 8/2015 |
| EP | 2234657 | B1 | 8/2015 |
| EP | 2250976 | B1 | 8/2015 |
| EP | 2262447 | B1 | 8/2015 |
| EP | 2303384 | B1 | 8/2015 |
| EP | 2387365 | B1 | 8/2015 |
| EP | 2560579 | B1 | 8/2015 |
| EP | 2575621 | B1 | 8/2015 |
| EP | 2590595 | B1 | 8/2015 |
| EP | 2709560 | B1 | 8/2015 |
| EP | 2755603 | B1 | 8/2015 |
| EP | 2906147 | A1 | 8/2015 |
| EP | 1534185 | B1 | 9/2015 |
| EP | 1765225 | B1 | 9/2015 |
| EP | 1778127 | B1 | 9/2015 |
| EP | 2094194 | B1 | 9/2015 |
| EP | 2201911 | B1 | 9/2015 |
| EP | 2306934 | B1 | 9/2015 |
| EP | 2397113 | B1 | 9/2015 |
| EP | 2453843 | B1 | 9/2015 |
| EP | 2459127 | B1 | 9/2015 |
| EP | 2675396 | B1 | 9/2015 |
| EP | 2675397 | B1 | 9/2015 |
| EP | 2736454 | B1 | 9/2015 |
| EP | 2754414 | A4 | 9/2015 |
| EP | 2790609 | B1 | 9/2015 |
| EP | 2805693 | B1 | 9/2015 |
| EP | 2916781 | A2 | 9/2015 |
| EP | 1734903 | B1 | 10/2015 |
| EP | 1863546 | B1 | 10/2015 |
| EP | 1900343 | B1 | 10/2015 |
| EP | 2081515 | B1 | 10/2015 |
| EP | 2191792 | B1 | 10/2015 |
| EP | 2254513 | B1 | 10/2015 |
| EP | 2381896 | B1 | 10/2015 |
| EP | 2450008 | B1 | 10/2015 |
| EP | 2544626 | B1 | 10/2015 |
| EP | 2561830 | B1 | 10/2015 |
| EP | 2600798 | B1 | 10/2015 |
| EP | 2626039 | B1 | 10/2015 |
| EP | 2647354 | B1 | 10/2015 |
| EP | 2729093 | B1 | 10/2015 |
| EP | 2836165 | B1 | 10/2015 |
| EP | 1863545 | B1 | 11/2015 |
| EP | 2303395 | B1 | 11/2015 |
| EP | 2497446 | B1 | 11/2015 |
| EP | 2772228 | B1 | 11/2015 |
| EP | 1482869 | B1 | 12/2015 |
| EP | 1551473 | B1 | 12/2015 |
| EP | 1748745 | B1 | 12/2015 |
| EP | 1755459 | B1 | 12/2015 |
| EP | 1850796 | B1 | 12/2015 |
| EP | 1922030 | B1 | 12/2015 |
| EP | 1954212 | B1 | 12/2015 |
| EP | 2424472 | B1 | 12/2015 |
| EP | 2470120 | B1 | 12/2015 |
| EP | 2542179 | B1 | 12/2015 |
| EP | 2948100 | A1 | 12/2015 |
| EP | 1991168 | B1 | 1/2016 |
| EP | 2254512 | B1 | 1/2016 |
| EP | 2422748 | B1 | 1/2016 |
| EP | 2967700 | A1 | 1/2016 |
| EP | 2967807 | A2 | 1/2016 |
| EP | 2967834 | A1 | 1/2016 |
| EP | 2967856 | A1 | 1/2016 |
| EP | 2967860 | A1 | 1/2016 |
| EP | 2967866 | A2 | 1/2016 |
| EP | 2977026 | A1 | 1/2016 |
| EP | 1754684 | B1 | 2/2016 |
| EP | 1835948 | B1 | 2/2016 |
| EP | 2012712 | B1 | 2/2016 |
| EP | 2285318 | B1 | 2/2016 |
| EP | 2731550 | B1 | 2/2016 |
| EP | 2926766 | B1 | 2/2016 |
| EP | 2982337 | A1 | 2/2016 |
| EP | 1585463 | B1 | 3/2016 |
| EP | 1638621 | B1 | 3/2016 |
| EP | 1804726 | B1 | 3/2016 |
| EP | 1865886 | B1 | 3/2016 |
| EP | 1887982 | B1 | 3/2016 |
| EP | 2150205 | B1 | 3/2016 |
| EP | 2278944 | B1 | 3/2016 |
| EP | 2291126 | B1 | 3/2016 |
| EP | 2517674 | B1 | 3/2016 |
| EP | 2520253 | B1 | 3/2016 |
| EP | 2526897 | B1 | 3/2016 |
| EP | 2670353 | B1 | 3/2016 |
| EP | 2674130 | B1 | 3/2016 |
| EP | 2780042 | B1 | 3/2016 |
| EP | 2991584 | A1 | 3/2016 |
| EP | 2991587 | A2 | 3/2016 |
| EP | 2994072 | A1 | 3/2016 |
| EP | 2994075 | A1 | 3/2016 |
| EP | 2996632 | A1 | 3/2016 |
| EP | 2996633 | A1 | 3/2016 |
| EP | 2996641 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |
| EP | 2572676 | B1 | 4/2016 |
| EP | 2606852 | B1 | 4/2016 |
| EP | 2621408 | B1 | 4/2016 |
| EP | 2626041 | B1 | 4/2016 |
| EP | 2633821 | B1 | 4/2016 |
| EP | 2670354 | B1 | 4/2016 |
| EP | 2702965 | B1 | 4/2016 |
| EP | 2704669 | B1 | 4/2016 |
| EP | 2815725 | B1 | 4/2016 |
| EP | 3007651 | A1 | 4/2016 |
| EP | 3010564 | A1 | 4/2016 |
| EP | 2194933 | B1 | 5/2016 |
| EP | 2237746 | B1 | 5/2016 |
| EP | 2378947 | B1 | 5/2016 |
| EP | 2542184 | B1 | 5/2016 |
| EP | 2572684 | B1 | 5/2016 |
| EP | 2582326 | B1 | 5/2016 |
| EP | 2618784 | B1 | 5/2016 |
| EP | 2654623 | B1 | 5/2016 |
| EP | 2656816 | B1 | 5/2016 |
| EP | 2680791 | B1 | 5/2016 |
| EP | 2693986 | B1 | 5/2016 |
| EP | 2806805 | B1 | 5/2016 |
| EP | 2866739 | B1 | 5/2016 |
| EP | 2889020 | B1 | 5/2016 |
| EP | 2926767 | B1 | 5/2016 |
| EP | 2949292 | B1 | 5/2016 |
| EP | 1734902 | B1 | 6/2016 |
| EP | 1906884 | B1 | 6/2016 |
| EP | 2111800 | B1 | 6/2016 |
| EP | 2160156 | B1 | 6/2016 |
| EP | 2190379 | B1 | 6/2016 |
| EP | 2193762 | B1 | 6/2016 |
| EP | 2416739 | B1 | 6/2016 |
| EP | 2453969 | B1 | 6/2016 |
| EP | 2515800 | B1 | 6/2016 |
| EP | 2558031 | B1 | 6/2016 |

(56) References Cited

FOREIGN PATENT DOCUMENTS

| | | | |
|---|---|---|---|
| EP | 2563236 B1 | 6/2016 |
| EP | 2572675 B1 | 6/2016 |
| EP | 2626040 B1 | 6/2016 |
| EP | 2704668 B1 | 6/2016 |
| EP | 2777611 B1 | 6/2016 |
| EP | 2815724 B1 | 6/2016 |
| EP | 2854710 B1 | 6/2016 |
| EP | 2901966 B1 | 6/2016 |
| EP | 3024527 A2 | 6/2016 |
| EP | 1605866 B1 | 7/2016 |
| EP | 1933756 B1 | 7/2016 |
| EP | 2393452 B1 | 7/2016 |
| EP | 2410948 B1 | 7/2016 |
| EP | 2412397 B1 | 7/2016 |
| EP | 2724690 B1 | 7/2016 |
| EP | 2815723 B1 | 7/2016 |
| EP | 2870945 B1 | 7/2016 |
| EP | 3040054 A1 | 7/2016 |
| EP | 3042635 A1 | 7/2016 |
| EP | 3043745 A1 | 7/2016 |
| EP | 3043747 A1 | 7/2016 |
| EP | 1401358 B1 | 8/2016 |
| EP | 1915105 B1 | 8/2016 |
| EP | 1937186 B1 | 8/2016 |
| EP | 2292186 B1 | 8/2016 |
| EP | 2379012 B1 | 8/2016 |
| EP | 2385809 B1 | 8/2016 |
| EP | 2536345 B1 | 8/2016 |
| EP | 2537490 B1 | 8/2016 |
| EP | 2549954 B1 | 8/2016 |
| EP | 2618779 B1 | 8/2016 |
| EP | 2670352 B1 | 8/2016 |
| EP | 2829235 B1 | 8/2016 |
| EP | 2853238 B1 | 8/2016 |
| EP | 2866738 B1 | 8/2016 |
| EP | 2906150 B1 | 8/2016 |
| EP | 3052053 A1 | 8/2016 |
| EP | 3060174 A1 | 8/2016 |
| EP | 3061421 A1 | 8/2016 |
| EP | 3061422 A1 | 8/2016 |
| EP | 1156755 B1 | 9/2016 |
| EP | 1492478 B1 | 9/2016 |
| EP | 1912697 B1 | 9/2016 |
| EP | 2393449 B1 | 9/2016 |
| EP | 2670356 B1 | 9/2016 |
| EP | 2793969 B1 | 9/2016 |
| EP | 2809271 B1 | 9/2016 |
| EP | 2896425 B1 | 9/2016 |
| EP | 3068345 A1 | 9/2016 |
| EP | 3068346 A1 | 9/2016 |
| EP | 3071148 A1 | 9/2016 |
| EP | 2023858 B1 | 10/2016 |
| EP | 2112912 B1 | 10/2016 |
| EP | 2640319 B1 | 10/2016 |
| EP | 2663257 B1 | 10/2016 |
| EP | 2727612 B1 | 10/2016 |
| EP | 2760384 B1 | 10/2016 |
| EP | 2806829 B1 | 10/2016 |
| EP | 2858599 B1 | 10/2016 |
| EP | 2918250 B1 | 10/2016 |
| EP | 2934387 B1 | 10/2016 |
| EP | 3076901 A1 | 10/2016 |
| EP | 1539047 B1 | 11/2016 |
| EP | 2282700 B1 | 11/2016 |
| EP | 2400926 B1 | 11/2016 |
| EP | 2467104 B1 | 11/2016 |
| EP | 2525743 B1 | 11/2016 |
| EP | 2549953 B1 | 11/2016 |
| EP | 2575696 B1 | 11/2016 |
| EP | 2598045 B1 | 11/2016 |
| EP | 2670355 B1 | 11/2016 |
| EP | 2676640 B1 | 11/2016 |
| EP | 2680792 B1 | 11/2016 |
| EP | 2707053 B1 | 11/2016 |
| EP | 2717803 B1 | 11/2016 |
| EP | 2773297 B1 | 11/2016 |
| EP | 2801387 B1 | 11/2016 |
| EP | 2844192 B1 | 11/2016 |
| EP | 2849679 B1 | 11/2016 |
| EP | 2877122 B1 | 11/2016 |
| EP | 2908778 B1 | 11/2016 |
| EP | 2922500 B1 | 11/2016 |
| EP | 2922501 B1 | 11/2016 |
| EP | 2967854 B1 | 11/2016 |
| EP | 3020365 B1 | 11/2016 |
| EP | 3090703 A1 | 11/2016 |
| EP | 1645244 B1 | 12/2016 |
| EP | 1667614 B1 | 12/2016 |
| EP | 1684656 B1 | 12/2016 |
| EP | 1684670 B1 | 12/2016 |
| EP | 1750592 B1 | 12/2016 |
| EP | 1883375 B1 | 12/2016 |
| EP | 2293739 B1 | 12/2016 |
| EP | 2339988 B1 | 12/2016 |
| EP | 2512375 B1 | 12/2016 |
| EP | 2754417 B1 | 12/2016 |
| EP | 2754418 B1 | 12/2016 |
| EP | 2755562 B1 | 12/2016 |
| EP | 2889019 B1 | 12/2016 |
| EP | 3010442 B1 | 12/2016 |
| EP | 3099271 A1 | 12/2016 |
| EP | 3107495 A1 | 12/2016 |
| EP | 3107498 A2 | 12/2016 |
| EP | 3107500 A1 | 12/2016 |
| EP | 1893127 B1 | 1/2017 |
| EP | 1951352 B1 | 1/2017 |
| EP | 2109419 B1 | 1/2017 |
| EP | 2185107 B1 | 1/2017 |
| EP | 2266503 B1 | 1/2017 |
| EP | 2340055 B1 | 1/2017 |
| EP | 2395941 B1 | 1/2017 |
| EP | 2400923 B1 | 1/2017 |
| EP | 2629699 B1 | 1/2017 |
| EP | 2645963 B1 | 1/2017 |
| EP | 2654622 B1 | 1/2017 |
| EP | 2706952 B1 | 1/2017 |
| EP | 2760347 B1 | 1/2017 |
| EP | 2771064 B1 | 1/2017 |
| EP | 2780077 B1 | 1/2017 |
| EP | 2809272 B1 | 1/2017 |
| EP | 2934385 B1 | 1/2017 |
| EP | 2986255 B1 | 1/2017 |
| EP | 3119351 A1 | 1/2017 |
| EP | 1507493 B1 | 2/2017 |
| EP | 2563238 B1 | 2/2017 |
| EP | 2752170 B1 | 2/2017 |
| EP | 2760371 B1 | 2/2017 |
| EP | 2793709 B1 | 2/2017 |
| EP | 2793748 B1 | 2/2017 |
| EP | 2793763 B1 | 2/2017 |
| EP | 2832317 B1 | 2/2017 |
| EP | 2921135 B1 | 2/2017 |
| EP | 2967931 B1 | 2/2017 |
| EP | 2974693 B1 | 2/2017 |
| EP | 3025680 B1 | 2/2017 |
| EP | 3025681 B1 | 2/2017 |
| EP | 3125826 A1 | 2/2017 |
| EP | 3125827 A2 | 2/2017 |
| EP | 3128927 A1 | 2/2017 |
| EP | 3131502 A1 | 2/2017 |
| EP | 1845895 B1 | 3/2017 |
| EP | 2190385 B1 | 3/2017 |
| EP | 2266504 B1 | 3/2017 |
| EP | 2341871 B1 | 3/2017 |
| EP | 2379011 B1 | 3/2017 |
| EP | 2379013 B1 | 3/2017 |
| EP | 2640316 B1 | 3/2017 |
| EP | 2731552 B1 | 3/2017 |
| EP | 2756109 B1 | 3/2017 |
| EP | 2773298 B1 | 3/2017 |
| EP | 2832316 B1 | 3/2017 |
| EP | 2854718 B1 | 3/2017 |
| EP | 2881083 B1 | 3/2017 |
| EP | 2934390 B1 | 3/2017 |

(56) References Cited

FOREIGN PATENT DOCUMENTS

| | | | |
|---|---|---|---|
| EP | 2934391 | B1 | 3/2017 |
| EP | 3010564 | A4 | 3/2017 |
| EP | 3145451 | A2 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2809270 | B1 | 5/2017 |
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384165 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3178443 | A1 | 6/2017 |
| EP | 3178445 | A1 | 6/2017 |
| EP | 3184081 | A1 | 6/2017 |
| EP | 1624810 | B1 | 7/2017 |
| EP | 2026703 | B1 | 7/2017 |
| EP | 2293718 | B1 | 7/2017 |
| EP | 2339989 | B1 | 7/2017 |
| EP | 2344076 | B1 | 7/2017 |
| EP | 2486893 | B1 | 7/2017 |
| EP | 2536356 | B1 | 7/2017 |
| EP | 2548534 | B1 | 7/2017 |
| EP | 2608742 | B1 | 7/2017 |
| EP | 2673038 | B1 | 7/2017 |
| EP | 2676638 | B1 | 7/2017 |
| EP | 2774630 | B1 | 7/2017 |
| EP | 2825107 | B1 | 7/2017 |
| EP | 2841020 | B1 | 7/2017 |
| EP | 2934386 | B1 | 7/2017 |
| EP | 2943151 | B1 | 7/2017 |
| EP | 3058894 | B1 | 7/2017 |
| EP | 3071151 | B1 | 7/2017 |
| EP | 3191025 | A1 | 7/2017 |
| EP | 3193740 | A2 | 7/2017 |
| EP | 3193782 | A1 | 7/2017 |
| EP | 1530441 | B1 | 8/2017 |
| EP | 1722716 | B1 | 8/2017 |
| EP | 1971289 | B1 | 8/2017 |
| EP | 2323591 | B1 | 8/2017 |
| EP | 2344070 | B1 | 8/2017 |
| EP | 2393442 | A4 | 8/2017 |
| EP | 2413842 | B1 | 8/2017 |
| EP | 2427143 | B1 | 8/2017 |
| EP | 2459077 | B1 | 8/2017 |
| EP | 2480167 | B1 | 8/2017 |
| EP | 2482749 | B1 | 8/2017 |
| EP | 2496181 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |
| EP | 2800602 | B1 | 8/2017 |
| EP | 2809263 | B1 | 8/2017 |
| EP | 2830536 | B1 | 8/2017 |
| EP | 2841009 | B1 | 8/2017 |
| EP | 2844190 | B1 | 8/2017 |
| EP | 2849681 | B1 | 8/2017 |
| EP | 2858600 | B1 | 8/2017 |
| EP | 2897556 | B1 | 8/2017 |
| EP | 2934388 | B1 | 8/2017 |
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |

(56) References Cited

FOREIGN PATENT DOCUMENTS

| | | |
|---|---|---|
| EP | 2618780 B1 | 11/2017 |
| EP | 2658480 B1 | 11/2017 |
| EP | 2710978 B1 | 11/2017 |
| EP | 2832315 B1 | 11/2017 |
| EP | 2954875 B1 | 11/2017 |
| EP | 2967861 B1 | 11/2017 |
| EP | 2982338 B1 | 11/2017 |
| EP | 3027144 B1 | 11/2017 |
| EP | 3043746 B1 | 11/2017 |
| EP | 3049026 B1 | 11/2017 |
| EP | 3068311 B1 | 11/2017 |
| EP | 3110368 B1 | 11/2017 |
| EP | 3110369 B1 | 11/2017 |
| EP | 3132773 B1 | 11/2017 |
| EP | 3238662 A1 | 11/2017 |
| EP | 3247312 A1 | 11/2017 |
| EP | 1667603 B1 | 12/2017 |
| EP | 1874954 B1 | 12/2017 |
| EP | 2427145 B1 | 12/2017 |
| EP | 2542185 B1 | 12/2017 |
| EP | 2723274 B1 | 12/2017 |
| EP | 2736455 B1 | 12/2017 |
| EP | 2736457 B1 | 12/2017 |
| EP | 2830534 B1 | 12/2017 |
| EP | 2830535 B1 | 12/2017 |
| EP | 2911592 B1 | 12/2017 |
| EP | 2916772 B1 | 12/2017 |
| EP | 2967922 B1 | 12/2017 |
| EP | 3009105 B1 | 12/2017 |
| EP | 3088037 B1 | 12/2017 |
| EP | 3115023 B1 | 12/2017 |
| EP | 3251633 A1 | 12/2017 |
| EP | 3256074 A1 | 12/2017 |
| EP | 3256076 A1 | 12/2017 |
| EP | 3256178 A1 | 12/2017 |
| EP | 1492458 B1 | 1/2018 |
| EP | 1768604 B1 | 1/2018 |
| EP | 1951154 B1 | 1/2018 |
| EP | 2091465 B1 | 1/2018 |
| EP | 2345380 B1 | 1/2018 |
| EP | 2456363 B1 | 1/2018 |
| EP | 2531143 B1 | 1/2018 |
| EP | 2621407 B1 | 1/2018 |
| EP | 2694123 B1 | 1/2018 |
| EP | 2775962 B1 | 1/2018 |
| EP | 2874568 B1 | 1/2018 |
| EP | 2967863 B1 | 1/2018 |
| EP | 2967869 B1 | 1/2018 |
| EP | 3033047 B1 | 1/2018 |
| EP | 3037065 B1 | 1/2018 |
| EP | 3049025 B1 | 1/2018 |
| EP | 3052052 B1 | 1/2018 |
| EP | 3078350 B1 | 1/2018 |
| EP | 3267946 A1 | 1/2018 |
| EP | 3269331 A1 | 1/2018 |
| EP | 3273911 A1 | 1/2018 |
| EP | 3275404 A1 | 1/2018 |
| EP | 2197512 B1 | 2/2018 |
| EP | 2248486 B1 | 2/2018 |
| EP | 2344066 B1 | 2/2018 |
| EP | 2381854 B1 | 2/2018 |
| EP | 2667823 B1 | 2/2018 |
| EP | 2699169 B1 | 2/2018 |
| EP | 2714177 B1 | 2/2018 |
| EP | 2736544 B1 | 2/2018 |
| EP | 2846736 B1 | 2/2018 |
| EP | 2886082 B1 | 2/2018 |
| EP | 2886084 B1 | 2/2018 |
| EP | 2931178 B1 | 2/2018 |
| EP | 2934392 B1 | 2/2018 |
| EP | 3150173 B1 | 2/2018 |
| EP | 3277222 A1 | 2/2018 |
| EP | 3281608 A1 | 2/2018 |
| EP | 3283011 A1 | 2/2018 |
| EP | 3287099 A1 | 2/2018 |
| EP | 1959864 B1 | 3/2018 |
| EP | 2513200 B1 | 3/2018 |
| EP | 2608815 B1 | 3/2018 |
| EP | 2858711 B1 | 3/2018 |
| EP | 2938292 B1 | 3/2018 |
| EP | 2943132 B1 | 3/2018 |
| EP | 2983620 B1 | 3/2018 |
| EP | 3003219 B1 | 3/2018 |
| EP | 3005979 B1 | 3/2018 |
| EP | 3037064 B1 | 3/2018 |
| EP | 3046511 B1 | 3/2018 |
| EP | 3142603 B1 | 3/2018 |
| EP | 3288479 A1 | 3/2018 |
| EP | 3288494 A1 | 3/2018 |
| EP | 3288497 A2 | 3/2018 |
| EP | 3288498 A1 | 3/2018 |
| EP | 3288499 A1 | 3/2018 |
| EP | 3290004 A1 | 3/2018 |
| EP | 3290007 A1 | 3/2018 |
| EP | 3294214 A1 | 3/2018 |
| EP | 3294215 A1 | 3/2018 |
| EP | 3294218 A1 | 3/2018 |
| EP | 3298970 A1 | 3/2018 |
| EP | 3298987 A1 | 3/2018 |
| EP | 2209440 B1 | 4/2018 |
| EP | 2536357 B1 | 4/2018 |
| EP | 2605725 B1 | 4/2018 |
| EP | 2608743 B1 | 4/2018 |
| EP | 2709561 B1 | 4/2018 |
| EP | 2787925 B1 | 4/2018 |
| EP | 2789314 B1 | 4/2018 |
| EP | 2900150 B1 | 4/2018 |
| EP | 2908779 B1 | 4/2018 |
| EP | 2922502 B1 | 4/2018 |
| EP | 2964441 B1 | 4/2018 |
| EP | 2967868 B1 | 4/2018 |
| EP | 2979665 B1 | 4/2018 |
| EP | 2994073 B1 | 4/2018 |
| EP | 3095394 B1 | 4/2018 |
| EP | 3128927 A4 | 4/2018 |
| EP | 3134033 B1 | 4/2018 |
| EP | 3137146 A4 | 4/2018 |
| EP | 3302362 A1 | 4/2018 |
| EP | 3308745 A1 | 4/2018 |
| EP | 3310301 A1 | 4/2018 |
| EP | 328048244 | 4/2018 |
| EP | 1945112 B1 | 5/2018 |
| EP | 2007313 B1 | 5/2018 |
| EP | 2316381 B2 | 5/2018 |
| EP | 2377469 B1 | 5/2018 |
| EP | 2531115 B1 | 5/2018 |
| EP | 2561831 B1 | 5/2018 |
| EP | 2605724 B1 | 5/2018 |
| EP | 2723277 B1 | 5/2018 |
| EP | 2741711 B1 | 5/2018 |
| EP | 2755573 B1 | 5/2018 |
| EP | 2768429 B1 | 5/2018 |
| EP | 2819618 B1 | 5/2018 |
| EP | 2833836 B1 | 5/2018 |
| EP | 2886083 B1 | 5/2018 |
| EP | 2926840 B1 | 5/2018 |
| EP | 2943157 B1 | 5/2018 |
| EP | 2948099 B1 | 5/2018 |
| EP | 3000437 B1 | 5/2018 |
| EP | 3145448 B1 | 5/2018 |
| EP | 3154475 B1 | 5/2018 |
| EP | 3316819 A1 | 5/2018 |
| EP | 3316821 A1 | 5/2018 |
| EP | 3322381 A1 | 5/2018 |
| EP | 3323353 A1 | 5/2018 |
| EP | 3323439 A1 | 5/2018 |
| EP | 3324892 A1 | 5/2018 |
| EP | 3326584 A1 | 5/2018 |
| EP | 2150312 B1 | 6/2018 |
| EP | 2379322 B1 | 6/2018 |
| EP | 2400925 B1 | 6/2018 |
| EP | 2552355 B1 | 6/2018 |
| EP | 2560589 B1 | 6/2018 |
| EP | 2563277 B1 | 6/2018 |

(56) References Cited

FOREIGN PATENT DOCUMENTS

| | | | |
|---|---|---|---|
| EP | 2661305 | B1 | 6/2018 |
| EP | 2736456 | B1 | 6/2018 |
| EP | 2782523 | B1 | 6/2018 |
| EP | 3056170 | B1 | 6/2018 |
| EP | 3062745 | B1 | 6/2018 |
| EP | 3130320 | B1 | 6/2018 |
| EP | 3187150 | B1 | 6/2018 |
| EP | 3334380 | A1 | 6/2018 |
| EP | 3334381 | A1 | 6/2018 |
| EP | 3337412 | A1 | 6/2018 |
| EP | 3337424 | A1 | 6/2018 |
| EP | 2478872 | B1 | 7/2018 |
| EP | 2563278 | B1 | 7/2018 |
| EP | 2616004 | B1 | 7/2018 |
| EP | 2779943 | B1 | 7/2018 |
| EP | 2802290 | B1 | 7/2018 |
| EP | 2816980 | B1 | 7/2018 |
| EP | 2938293 | B1 | 7/2018 |
| EP | 3107496 | B1 | 7/2018 |
| EP | 3178450 | B1 | 7/2018 |
| EP | 3212097 | B1 | 7/2018 |
| EP | 3340936 | A1 | 7/2018 |
| EP | 3342355 | A1 | 7/2018 |
| EP | 3342377 | A1 | 7/2018 |
| EP | 3348235 | A1 | 7/2018 |
| EP | 2536354 | B1 | 8/2018 |
| EP | 2616006 | B1 | 8/2018 |
| EP | 2797556 | B1 | 8/2018 |
| EP | 2822473 | B1 | 8/2018 |
| EP | 2854711 | B1 | 8/2018 |
| EP | 2866847 | B1 | 8/2018 |
| EP | 2918246 | B1 | 8/2018 |
| EP | 2967845 | B1 | 8/2018 |
| EP | 2999436 | B1 | 8/2018 |
| EP | 3013281 | B1 | 8/2018 |
| EP | 3060170 | B1 | 8/2018 |
| EP | 3104811 | B1 | 8/2018 |
| EP | 3143944 | B1 | 8/2018 |
| EP | 3157467 | B1 | 8/2018 |
| EP | 3193791 | B1 | 8/2018 |
| EP | 3241526 | B1 | 8/2018 |
| EP | 3355800 | A1 | 8/2018 |
| EP | 3360513 | A1 | 8/2018 |
| EP | 3360514 | A1 | 8/2018 |
| EP | 3361988 | A1 | 8/2018 |
| EP | 2114305 | B1 | 9/2018 |
| EP | 2155115 | B1 | 9/2018 |
| EP | 2601910 | B1 | 9/2018 |
| EP | 2617390 | B1 | 9/2018 |
| EP | 2734157 | B1 | 9/2018 |
| EP | 2968674 | B1 | 9/2018 |
| EP | 2999415 | B1 | 9/2018 |
| EP | 3106130 | B1 | 9/2018 |
| EP | 3151763 | B1 | 9/2018 |
| EP | 3213717 | B1 | 9/2018 |
| EP | 3245985 | B1 | 9/2018 |
| EP | 3367979 | A1 | 9/2018 |
| EP | 1827256 | B1 | 10/2018 |
| EP | 1850790 | B1 | 10/2018 |
| EP | 2063823 | B1 | 10/2018 |
| EP | 2124825 | B1 | 10/2018 |
| EP | 2249746 | B1 | 10/2018 |
| EP | 2254514 | B1 | 10/2018 |
| EP | 2285309 | B1 | 10/2018 |
| EP | 2455042 | B1 | 10/2018 |
| EP | 2571561 | B1 | 10/2018 |
| EP | 2616008 | B1 | 10/2018 |
| EP | 2647393 | B1 | 10/2018 |
| EP | 2739214 | B1 | 10/2018 |
| EP | 2739247 | B1 | 10/2018 |
| EP | 2776114 | B1 | 10/2018 |
| EP | 2836171 | B1 | 10/2018 |
| EP | 2842581 | B1 | 10/2018 |
| EP | 2870946 | B1 | 10/2018 |
| EP | 2923665 | B1 | 10/2018 |
| EP | 2964277 | B1 | 10/2018 |
| EP | 3001978 | B1 | 10/2018 |
| EP | 3010562 | B1 | 10/2018 |
| EP | 3072475 | B1 | 10/2018 |
| EP | 3081161 | B1 | 10/2018 |
| EP | 3081195 | B1 | 10/2018 |
| EP | 3099345 | B1 | 10/2018 |
| EP | 3120809 | B1 | 10/2018 |
| EP | 3238663 | B1 | 10/2018 |
| EP | 3275404 | A4 | 10/2018 |
| EP | 3384879 | A1 | 10/2018 |
| EP | 1708650 | B1 | 11/2018 |
| EP | 1945143 | B1 | 11/2018 |
| EP | 2205183 | B1 | 11/2018 |
| EP | 2663258 | B1 | 11/2018 |
| EP | 2790615 | B1 | 11/2018 |
| EP | 2854709 | B1 | 11/2018 |
| EP | 2898859 | B1 | 11/2018 |
| EP | 2921139 | B1 | 11/2018 |
| EP | 2928538 | B1 | 11/2018 |
| EP | 3075354 | B1 | 11/2018 |
| EP | 3082949 | B1 | 11/2018 |
| EP | 3145452 | B1 | 11/2018 |
| EP | 3216424 | B1 | 11/2018 |
| EP | 3260084 | B1 | 11/2018 |
| EP | 3400908 | A1 | 11/2018 |
| EP | 3405139 | A1 | 11/2018 |
| EP | 1858450 | B1 | 12/2018 |
| EP | 2150208 | B1 | 12/2018 |
| EP | 2326261 | B1 | 12/2018 |
| EP | 2344075 | B1 | 12/2018 |
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3206628 | B1 | 12/2018 |
| EP | 3242629 | B1 | 12/2018 |
| EP | 3260085 | B1 | 12/2018 |
| EP | 3266416 | B1 | 12/2018 |
| EP | 3326583 | B1 | 12/2018 |
| EP | 3410987 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3332743 | B1 | 1/2019 |
| EP | 3429507 | A1 | 1/2019 |
| EP | 3432832 | A1 | 1/2019 |
| EP | 3432834 | A1 | 1/2019 |
| EP | 3558168 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688562 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |

(56) References Cited

FOREIGN PATENT DOCUMENTS

| | | | |
|---|---|---|---|
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3435919 | A1 | 2/2019 |
| EP | 3441045 | A1 | 2/2019 |
| EP | 3442469 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3454785 | A1 | 3/2019 |
| EP | 3454786 | A1 | 3/2019 |
| EP | 3454794 | A1 | 3/2019 |
| EP | 3457987 | A1 | 3/2019 |
| EP | 3457988 | A1 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |
| EP | 2536358 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3479797 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3488822 | A1 | 5/2019 |
| EP | 1624792 | B1 | 6/2019 |
| EP | 1737394 | B1 | 6/2019 |
| EP | 1858451 | B1 | 6/2019 |
| EP | 1895944 | B1 | 6/2019 |
| EP | 1968487 | B1 | 6/2019 |
| EP | 2004095 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |
| EP | 2868296 | B1 | 6/2019 |
| EP | 2961358 | B1 | 6/2019 |
| EP | 2967847 | B1 | 6/2019 |
| EP | 2985006 | B1 | 6/2019 |
| EP | 3033048 | B1 | 6/2019 |
| EP | 3119451 | B1 | 6/2019 |
| EP | 3131503 | B1 | 6/2019 |
| EP | 3213718 | B1 | 6/2019 |
| EP | 3275390 | B1 | 6/2019 |
| EP | 3300692 | B1 | 6/2019 |
| EP | 3326585 | B1 | 6/2019 |
| EP | 3338737 | B1 | 6/2019 |
| EP | 3357457 | B1 | 6/2019 |
| EP | 3372198 | B1 | 6/2019 |
| EP | 3490465 | A1 | 6/2019 |
| EP | 3496626 | A1 | 6/2019 |
| EP | 3496664 | A1 | 6/2019 |
| EP | 3498224 | A1 | 6/2019 |
| EP | 3501454 | A1 | 6/2019 |
| EP | 1659981 | B1 | 7/2019 |
| EP | 1924223 | B1 | 7/2019 |
| EP | 2249745 | B1 | 7/2019 |
| EP | 2296744 | B1 | 7/2019 |
| EP | 2331019 | B1 | 7/2019 |
| EP | 2368527 | B1 | 7/2019 |
| EP | 2509542 | B1 | 7/2019 |
| EP | 2555710 | B1 | 7/2019 |
| EP | 2575682 | B1 | 7/2019 |
| EP | 2575683 | B1 | 7/2019 |
| EP | 2640431 | B1 | 7/2019 |
| EP | 2641572 | B1 | 7/2019 |
| EP | 2649964 | B1 | 7/2019 |
| EP | 2767260 | B1 | 7/2019 |
| EP | 2777615 | B1 | 7/2019 |
| EP | 2838476 | B1 | 7/2019 |
| EP | 2861186 | B1 | 7/2019 |
| EP | 2877124 | B1 | 7/2019 |
| EP | 2877132 | B1 | 7/2019 |
| EP | 2921565 | B1 | 7/2019 |
| EP | 2938291 | B1 | 7/2019 |
| EP | 2999433 | B1 | 7/2019 |
| EP | 3145450 | B1 | 7/2019 |
| EP | 3254644 | B1 | 7/2019 |
| EP | 3315093 | B1 | 7/2019 |
| EP | 3344189 | B1 | 7/2019 |
| EP | 3503813 | A1 | 7/2019 |
| EP | 3503846 | A1 | 7/2019 |
| EP | 3503847 | A1 | 7/2019 |
| EP | 3503848 | A1 | 7/2019 |
| EP | 3505077 | A1 | 7/2019 |
| EP | 3512465 | A1 | 7/2019 |
| EP | 1861043 | B1 | 8/2019 |

(56) References Cited

FOREIGN PATENT DOCUMENTS

| | | | |
|---|---|---|---|
| EP | 2303190 | B1 | 8/2019 |
| EP | 2593171 | B1 | 8/2019 |
| EP | 2632393 | B1 | 8/2019 |
| EP | 2663355 | B1 | 8/2019 |
| EP | 2665509 | B1 | 8/2019 |
| EP | 2688525 | B1 | 8/2019 |
| EP | 2699201 | B1 | 8/2019 |
| EP | 2755564 | B1 | 8/2019 |
| EP | 2769681 | B1 | 8/2019 |
| EP | 2793751 | B1 | 8/2019 |
| EP | 2900177 | B1 | 8/2019 |
| EP | 2967536 | B1 | 8/2019 |
| EP | 3050541 | B1 | 8/2019 |
| EP | 3102152 | B1 | 8/2019 |
| EP | 3157607 | B1 | 8/2019 |
| EP | 3231392 | B1 | 8/2019 |
| EP | 3284411 | B1 | 8/2019 |
| EP | 3328318 | B1 | 8/2019 |
| EP | 3348233 | B1 | 8/2019 |
| EP | 3366262 | B1 | 8/2019 |
| EP | 3527170 | A1 | 8/2019 |
| EP | 3530236 | A1 | 8/2019 |
| EP | 2358297 | B1 | 9/2019 |
| EP | 2368525 | B1 | 9/2019 |
| EP | 2542186 | B1 | 9/2019 |
| EP | 2656863 | B1 | 9/2019 |
| EP | 3003221 | B1 | 9/2019 |
| EP | 3003452 | B1 | 9/2019 |
| EP | 3220971 | B1 | 9/2019 |
| EP | 3223874 | B1 | 9/2019 |
| EP | 3288495 | B1 | 9/2019 |
| EP | 3311776 | B1 | 9/2019 |
| EP | 3334379 | B1 | 9/2019 |
| EP | 3531975 | A1 | 9/2019 |
| EP | 3534840 | A1 | 9/2019 |
| EP | 3534845 | A2 | 9/2019 |
| EP | 3535010 | A1 | 9/2019 |
| EP | 3538027 | A1 | 9/2019 |
| EP | 3539508 | A1 | 9/2019 |
| EP | 3539509 | A1 | 9/2019 |
| EP | 1740265 | B1 | 10/2019 |
| EP | 2039756 | B1 | 10/2019 |
| EP | 2456506 | B1 | 10/2019 |
| EP | 2470122 | B1 | 10/2019 |
| EP | 2613738 | B1 | 10/2019 |
| EP | 2637607 | B1 | 10/2019 |
| EP | 2674174 | B1 | 10/2019 |
| EP | 2811923 | B1 | 10/2019 |
| EP | 2901967 | B1 | 10/2019 |
| EP | 3010431 | B1 | 10/2019 |
| EP | 3019091 | B1 | 10/2019 |
| EP | 3019123 | B1 | 10/2019 |
| EP | 3057522 | B1 | 10/2019 |
| EP | 3067075 | B1 | 10/2019 |
| EP | 3146937 | B1 | 10/2019 |
| EP | 3238777 | B1 | 10/2019 |
| EP | 3359211 | B1 | 10/2019 |
| EP | 3388026 | B1 | 10/2019 |
| EP | 3432806 | B1 | 10/2019 |
| EP | 3496626 | A4 | 10/2019 |
| EP | 3544548 | A1 | 10/2019 |
| EP | 3547936 | A1 | 10/2019 |
| EP | 3547966 | A1 | 10/2019 |
| EP | 3549555 | A1 | 10/2019 |
| EP | 3558165 | A1 | 10/2019 |
| EP | 3558169 | A2 | 10/2019 |
| EP | 2043559 | B1 | 11/2019 |
| EP | 2358308 | B1 | 11/2019 |
| EP | 2405863 | B1 | 11/2019 |
| EP | 2701633 | B1 | 11/2019 |
| EP | 2898857 | B1 | 11/2019 |
| EP | 2967853 | B1 | 11/2019 |
| EP | 3009104 | B1 | 11/2019 |
| EP | 3021792 | B1 | 11/2019 |
| EP | 3076900 | B1 | 11/2019 |
| EP | 3111889 | B1 | 11/2019 |
| EP | 3142607 | B1 | 11/2019 |
| EP | 3167850 | B1 | 11/2019 |
| EP | 3397205 | B1 | 11/2019 |
| EP | 3572117 | A1 | 11/2019 |
| EP | 3479800 | A4 | 12/2019 |
| EP | 3576677 | A1 | 12/2019 |
| EP | 3579761 | A2 | 12/2019 |
| EP | 3582697 | A1 | 12/2019 |
| EP | 3583922 | A1 | 12/2019 |
| EP | 3445443 | A4 | 1/2020 |
| EP | 3590471 | A1 | 1/2020 |
| EP | 3590472 | A1 | 1/2020 |
| EP | 3592284 | A1 | 1/2020 |
| EP | 3592288 | A1 | 1/2020 |
| EP | 3592289 | A1 | 1/2020 |
| EP | 3593763 | A1 | 1/2020 |
| EP | 3600159 | A1 | 2/2020 |
| EP | 3606472 | A1 | 2/2020 |
| EP | 2241287 | B2 | 3/2020 |
| EP | 2376013 | B1 | 3/2020 |
| EP | 2911593 | B1 | 3/2020 |
| EP | 2995279 | B1 | 3/2020 |
| EP | 3009103 | B1 | 3/2020 |
| EP | 3038664 | B1 | 3/2020 |
| EP | 3167848 | B1 | 3/2020 |
| EP | 3175822 | B1 | 3/2020 |
| EP | 3179960 | B1 | 3/2020 |
| EP | 3280479 | B1 | 3/2020 |
| EP | 3616651 | A1 | 3/2020 |
| EP | 3619136 | A1 | 3/2020 |
| EP | 3626208 | A1 | 3/2020 |
| EP | 1667614 | B2 | 4/2020 |
| EP | 2119417 | B2 | 4/2020 |
| EP | 2155114 | B1 | 4/2020 |
| EP | 2299937 | B1 | 4/2020 |
| EP | 2331016 | B1 | 4/2020 |
| EP | 2376013 | B8 | 4/2020 |
| EP | 2413843 | B1 | 4/2020 |
| EP | 2854705 | B1 | 4/2020 |
| EP | 2918249 | B1 | 4/2020 |
| EP | 2922593 | B1 | 4/2020 |
| EP | 2950753 | B1 | 4/2020 |
| EP | 2967810 | B1 | 4/2020 |
| EP | 3110367 | B1 | 4/2020 |
| EP | 3111888 | B1 | 4/2020 |
| EP | 3128927 | B1 | 4/2020 |
| EP | 3134032 | B1 | 4/2020 |
| EP | 3142606 | B1 | 4/2020 |
| EP | 3270825 | B1 | 4/2020 |
| EP | 3300696 | B1 | 4/2020 |
| EP | 3316823 | B1 | 4/2020 |
| EP | 3334487 | B1 | 4/2020 |
| EP | 3342355 | B1 | 4/2020 |
| EP | 3373863 | B1 | 4/2020 |
| EP | 3459498 | B1 | 4/2020 |
| EP | 3470105 | B1 | 4/2020 |
| EP | 3632338 | A1 | 4/2020 |
| EP | 3636312 | A1 | 4/2020 |
| EP | 3639792 | A1 | 4/2020 |
| EP | 3639888 | A1 | 4/2020 |
| EP | 3643273 | A1 | 4/2020 |
| EP | 1895942 | B1 | 5/2020 |
| EP | 2120821 | B1 | 5/2020 |
| EP | 2437688 | B1 | 5/2020 |
| EP | 2785281 | B1 | 5/2020 |
| EP | 2852354 | B1 | 5/2020 |
| EP | 2884906 | B1 | 5/2020 |
| EP | 2999412 | B1 | 5/2020 |
| EP | 3060174 | B1 | 5/2020 |
| EP | 3071147 | B1 | 5/2020 |
| EP | 3104812 | B1 | 5/2020 |
| EP | 3139861 | B1 | 5/2020 |
| EP | 3232989 | B1 | 5/2020 |
| EP | 3294219 | B1 | 5/2020 |
| EP | 3298970 | B1 | 5/2020 |
| EP | 3302366 | B1 | 5/2020 |
| EP | 3323389 | B1 | 5/2020 |
| EP | 3332744 | B1 | 5/2020 |

(56) References Cited

FOREIGN PATENT DOCUMENTS

| | | | |
|---|---|---|---|
| EP | 3402440 | B1 | 5/2020 |
| EP | 3417813 | B1 | 5/2020 |
| EP | 3417831 | B1 | 5/2020 |
| EP | 3457987 | B1 | 5/2020 |
| EP | 3484413 | B1 | 5/2020 |
| EP | 3531975 | B1 | 5/2020 |
| EP | 3644866 | A1 | 5/2020 |
| EP | 3646822 | A1 | 5/2020 |
| EP | 3646824 | A1 | 5/2020 |
| EP | 3646825 | A1 | 5/2020 |
| EP | 3656354 | A1 | 5/2020 |
| EP | 1648339 | B2 | 6/2020 |
| EP | 2072027 | B1 | 6/2020 |
| EP | 2331016 | B8 | 6/2020 |
| EP | 2616007 | B1 | 6/2020 |
| EP | 2967856 | B1 | 6/2020 |
| EP | 3042635 | B1 | 6/2020 |
| EP | 3060165 | B1 | 6/2020 |
| EP | 3280338 | B1 | 6/2020 |
| EP | 3283010 | B1 | 6/2020 |
| EP | 3400908 | B1 | 6/2020 |
| EP | 3494928 | B1 | 6/2020 |
| EP | 3498225 | B1 | 6/2020 |
| EP | 3583920 | B1 | 6/2020 |
| EP | 3659553 | A1 | 6/2020 |
| EP | 3668450 | A1 | 6/2020 |
| EP | 3668452 | A1 | 6/2020 |
| EP | 3669828 | A1 | 6/2020 |
| EP | 3669829 | A1 | 6/2020 |
| EP | 2271284 | B1 | 7/2020 |
| EP | 2291145 | B1 | 7/2020 |
| EP | 2512952 | B1 | 7/2020 |
| EP | 2558029 | B1 | 7/2020 |
| EP | 2693985 | B1 | 7/2020 |
| EP | 2858708 | B1 | 7/2020 |
| EP | 2862546 | B1 | 7/2020 |
| EP | 2967807 | B1 | 7/2020 |
| EP | 2967866 | B1 | 7/2020 |
| EP | 3061421 | B1 | 7/2020 |
| EP | 3107497 | B1 | 7/2020 |
| EP | 3139862 | B1 | 7/2020 |
| EP | 3423000 | B1 | 7/2020 |
| EP | 3441045 | B1 | 7/2020 |
| EP | 3451972 | B1 | 7/2020 |
| EP | 3501454 | B1 | 7/2020 |
| EP | 3512466 | B1 | 7/2020 |
| EP | 3616652 | B1 | 7/2020 |
| EP | 3672528 | A1 | 7/2020 |
| EP | 3672529 | A1 | 7/2020 |
| EP | 3673925 | A1 | 7/2020 |
| EP | 3679894 | A1 | 7/2020 |
| EP | 3681439 | A1 | 7/2020 |
| EP | 3681441 | A1 | 7/2020 |
| EP | 3682852 | A1 | 7/2020 |
| EP | 3682854 | A1 | 7/2020 |
| EP | 2367505 | B1 | 8/2020 |
| EP | 2497445 | B1 | 8/2020 |
| EP | 2537486 | B1 | 8/2020 |
| EP | 2777616 | B1 | 8/2020 |
| EP | 3007651 | B1 | 8/2020 |
| EP | 3052053 | B1 | 8/2020 |
| EP | 3237033 | B1 | 8/2020 |
| EP | 3388005 | B1 | 8/2020 |
| EP | 3410986 | B1 | 8/2020 |
| EP | 3451974 | B1 | 8/2020 |
| EP | 3463192 | B1 | 8/2020 |
| EP | 3554423 | B1 | 8/2020 |
| EP | 3568089 | A4 | 8/2020 |
| EP | 3573544 | B1 | 8/2020 |
| EP | 3634255 | B1 | 8/2020 |
| EP | 3689299 | A1 | 8/2020 |
| EP | 3691567 | A1 | 8/2020 |
| EP | 3697346 | A1 | 8/2020 |
| EP | 2485795 | B1 | 9/2020 |
| EP | 3125777 | B1 | 9/2020 |
| EP | 3182930 | B1 | 9/2020 |
| EP | 3285690 | B1 | 9/2020 |
| EP | 3459500 | B1 | 9/2020 |
| EP | 3570782 | B1 | 9/2020 |
| EP | 3700467 | A1 | 9/2020 |
| EP | 3711711 | A1 | 9/2020 |
| EP | 3714936 | A1 | 9/2020 |
| EP | 2979667 | B2 | 10/2020 |
| EP | 3193783 | B1 | 10/2020 |
| EP | 3490501 | B1 | 10/2020 |
| EP | 3720363 | A1 | 10/2020 |
| EP | 2387973 | B1 | 11/2020 |
| EP | 2427144 | B1 | 11/2020 |
| EP | 2506777 | B1 | 11/2020 |
| EP | 2793743 | B1 | 11/2020 |
| EP | 2825203 | B1 | 11/2020 |
| EP | 2863842 | B1 | 11/2020 |
| EP | 2967700 | B1 | 11/2020 |
| EP | 2977026 | B1 | 11/2020 |
| EP | 3139864 | B1 | 11/2020 |
| EP | 3145451 | B1 | 11/2020 |
| EP | 3156007 | B1 | 11/2020 |
| EP | 3244834 | B1 | 11/2020 |
| EP | 3298987 | B1 | 11/2020 |
| EP | 3302362 | B1 | 11/2020 |
| EP | 3311777 | B1 | 11/2020 |
| EP | 3316819 | B1 | 11/2020 |
| EP | 3361988 | B1 | 11/2020 |
| EP | 3503813 | B1 | 11/2020 |
| EP | 3527170 | B1 | 11/2020 |
| EP | 3530236 | B1 | 11/2020 |
| EP | 3590471 | B1 | 11/2020 |
| EP | 3593762 | B1 | 11/2020 |
| EP | 3740162 | A1 | 11/2020 |
| EP | 2370138 | B1 | 12/2020 |
| EP | 2445450 | B1 | 12/2020 |
| EP | 2739250 | B1 | 12/2020 |
| EP | 2877123 | B1 | 12/2020 |
| EP | 2967834 | B1 | 12/2020 |
| EP | 2996632 | B1 | 12/2020 |
| EP | 3090703 | B1 | 12/2020 |
| EP | 3191025 | B1 | 12/2020 |
| EP | 3202371 | B1 | 12/2020 |
| EP | 3316822 | B1 | 12/2020 |
| EP | 3334382 | B1 | 12/2020 |
| EP | 3337424 | B1 | 12/2020 |
| EP | 3367896 | B1 | 12/2020 |
| EP | 3368582 | B1 | 12/2020 |
| EP | 3397208 | B1 | 12/2020 |
| EP | 3476366 | B1 | 12/2020 |
| EP | 3481303 | B1 | 12/2020 |
| EP | 3538028 | B1 | 12/2020 |
| EP | 3539510 | B1 | 12/2020 |
| EP | 3544548 | B1 | 12/2020 |
| EP | 3545906 | B1 | 12/2020 |
| EP | 3572117 | B1 | 12/2020 |
| EP | 3593763 | B1 | 12/2020 |
| EP | 3749254 | A1 | 12/2020 |
| EP | 3753535 | A1 | 12/2020 |
| EP | 1906883 | B1 | 1/2021 |
| EP | 2334261 | B1 | 1/2021 |
| EP | 2349096 | B1 | 1/2021 |
| EP | 2568924 | B1 | 1/2021 |
| EP | 2699202 | B1 | 1/2021 |
| EP | 2713894 | B1 | 1/2021 |
| EP | 2835112 | B1 | 1/2021 |
| EP | 3040054 | B1 | 1/2021 |
| EP | 3131502 | B1 | 1/2021 |
| EP | 3197397 | B1 | 1/2021 |
| EP | 3256178 | B1 | 1/2021 |
| EP | 3290007 | B1 | 1/2021 |
| EP | 3316821 | B1 | 1/2021 |
| EP | 3337412 | B1 | 1/2021 |
| EP | 3432834 | B1 | 1/2021 |
| EP | 3454786 | B1 | 1/2021 |
| EP | 3474778 | B1 | 1/2021 |
| EP | 3528748 | B1 | 1/2021 |
| EP | 3547966 | B1 | 1/2021 |
| EP | 3603576 | B1 | 1/2021 |

(56) References Cited

FOREIGN PATENT DOCUMENTS

| | | |
|---|---|---|
| EP | 3760164 A1 | 1/2021 |
| EP | 2273951 B1 | 2/2021 |
| EP | 2379008 B1 | 2/2021 |
| EP | 2996641 B1 | 2/2021 |
| EP | 3043747 B1 | 2/2021 |
| EP | 3340936 B1 | 2/2021 |
| EP | 3457985 B1 | 2/2021 |
| EP | 3503847 B1 | 2/2021 |
| EP | 3538027 B1 | 2/2021 |
| EP | 3558168 B1 | 2/2021 |
| EP | 3581232 B1 | 2/2021 |
| EP | 3656354 B1 | 2/2021 |
| EP | 3697324 B1 | 2/2021 |
| EP | 2299938 B1 | 3/2021 |
| EP | 2470121 B1 | 3/2021 |
| EP | 2564811 B1 | 3/2021 |
| EP | 2679198 B1 | 3/2021 |
| EP | 3068346 B1 | 3/2021 |
| EP | 3160394 B1 | 3/2021 |
| EP | 3169245 B1 | 3/2021 |
| EP | 3178443 B1 | 3/2021 |
| EP | 3184081 B1 | 3/2021 |
| EP | 3226956 B1 | 3/2021 |
| EP | 3324892 B1 | 3/2021 |
| EP | 3334354 B1 | 3/2021 |
| EP | 3402446 B1 | 3/2021 |
| EP | 3442469 B1 | 3/2021 |
| EP | 3503851 B1 | 3/2021 |
| EP | 3506855 B1 | 3/2021 |
| EP | 3531979 B1 | 3/2021 |
| EP | 3535010 B1 | 3/2021 |
| EP | 3581151 B1 | 3/2021 |
| EP | 3590472 B1 | 3/2021 |
| EP | 3593760 B1 | 3/2021 |
| EP | 3646825 B1 | 3/2021 |
| EP | 3649985 B1 | 3/2021 |
| EP | 3787561 A1 | 3/2021 |
| EP | 3791795 A1 | 3/2021 |
| EP | 1734872 B1 | 4/2021 |
| EP | 2594230 B1 | 4/2021 |
| EP | 2624785 B1 | 4/2021 |
| EP | 2670349 B1 | 4/2021 |
| EP | 2793752 B1 | 4/2021 |
| EP | 2823769 B1 | 4/2021 |
| EP | 2964152 B1 | 4/2021 |
| EP | 3253331 B1 | 4/2021 |
| EP | 3290004 B1 | 4/2021 |
| EP | 3311778 B1 | 4/2021 |
| EP | 3367979 B1 | 4/2021 |
| EP | 3454794 B1 | 4/2021 |
| EP | 3487420 B1 | 4/2021 |
| EP | 3558165 B1 | 4/2021 |
| EP | 3616651 B1 | 4/2021 |
| EP | 3619136 B1 | 4/2021 |
| EP | 3626208 B1 | 4/2021 |
| EP | 3632379 B1 | 4/2021 |
| EP | 3646823 B1 | 4/2021 |
| EP | 3646824 B1 | 4/2021 |
| EP | 3653173 B1 | 4/2021 |
| EP | 1951155 B1 | 5/2021 |
| EP | 2073755 B1 | 5/2021 |
| EP | 2948100 B1 | 5/2021 |
| EP | 3099270 B1 | 5/2021 |
| EP | 3150172 B1 | 5/2021 |
| EP | 3178445 B1 | 5/2021 |
| EP | 3310301 B1 | 5/2021 |
| EP | 3582697 B1 | 5/2021 |
| EP | 3592295 B1 | 5/2021 |
| EP | 3639888 B1 | 5/2021 |
| EP | 366982881 | 5/2021 |
| EP | 2471492 B1 | 6/2021 |
| EP | 2486894 B1 | 6/2021 |
| EP | 2750630 B1 | 6/2021 |
| EP | 3247312 B1 | 6/2021 |
| EP | 3294215 B1 | 6/2021 |
| EP | 3323353 B1 | 6/2021 |
| EP | 3360513 B1 | 6/2021 |
| EP | 3488821 B1 | 6/2021 |
| EP | 3549555 B1 | 6/2021 |
| EP | 3576677 B1 | 6/2021 |
| EP | 3632338 B1 | 6/2021 |
| EP | 2381895 B1 | 7/2021 |
| EP | 2611389 B1 | 7/2021 |
| EP | 2779945 B1 | 7/2021 |
| EP | 3193740 B1 | 7/2021 |
| EP | 3206629 B1 | 7/2021 |
| EP | 3277222 B1 | 7/2021 |
| EP | 3400907 B1 | 7/2021 |
| EP | 3435919 B1 | 7/2021 |
| EP | 3522800 B1 | 7/2021 |
| EP | 3539508 B1 | 7/2021 |
| EP | 3539509 B1 | 7/2021 |
| EP | 3572044 B1 | 7/2021 |
| EP | 3592289 B1 | 7/2021 |
| EP | 3668450 B1 | 7/2021 |
| EP | 3681439 B1 | 7/2021 |
| EP | 3691567 B1 | 7/2021 |
| EP | 2558032 B1 | 8/2021 |
| EP | 2992857 B1 | 8/2021 |
| EP | 2994075 B1 | 8/2021 |
| EP | 3038539 B1 | 8/2021 |
| EP | 3287099 B1 | 8/2021 |
| EP | 3348235 B1 | 8/2021 |
| EP | 3643273 B1 | 8/2021 |
| EP | 3646822 B1 | 8/2021 |
| EP | 3658215 B1 | 8/2021 |
| EP | 3723665 B1 | 8/2021 |
| EP | 3744290 B1 | 8/2021 |
| EP | 3860530 A1 | 8/2021 |
| EP | 365955381 | 8/2021 |
| EP | 2040645 B1 | 9/2021 |
| EP | 2329796 B1 | 9/2021 |
| EP | 3125827 B1 | 9/2021 |
| EP | 3137146 B1 | 9/2021 |
| EP | 3288494 B1 | 9/2021 |
| EP | 3288497 B1 | 9/2021 |
| EP | 3446660 B1 | 9/2021 |
| EP | 3454784 B1 | 9/2021 |
| EP | 3456293 B1 | 9/2021 |
| EP | 3457989 B1 | 9/2021 |
| EP | 3496664 B1 | 9/2021 |
| EP | 3503848 B1 | 9/2021 |
| EP | 3512465 B1 | 9/2021 |
| EP | 3544664 B1 | 9/2021 |
| EP | 3568089 B1 | 9/2021 |
| EP | 3592288 B1 | 9/2021 |
| EP | 3606472 B1 | 9/2021 |
| EP | 3669829 B1 | 9/2021 |
| EP | 367252881 | 9/2021 |
| EP | 2249711 B1 | 10/2021 |
| EP | 2538883 B1 | 10/2021 |
| EP | 2723273 B1 | 10/2021 |
| EP | 3119351 B1 | 10/2021 |
| EP | 3256076 B1 | 10/2021 |
| EP | 3267946 B1 | 10/2021 |
| EP | 3275404 B1 | 10/2021 |
| EP | 3280482 B1 | 10/2021 |
| EP | 3334381 B1 | 10/2021 |
| EP | 3639792 B1 | 10/2021 |
| EP | 2331018 B1 | 11/2021 |
| EP | 2429455 B1 | 11/2021 |
| EP | 2538878 B1 | 11/2021 |
| EP | 2699302 B1 | 11/2021 |
| EP | 2706958 B1 | 11/2021 |
| EP | 2892467 B1 | 11/2021 |
| EP | 2999434 B1 | 11/2021 |
| EP | 3024527 B1 | 11/2021 |
| EP | 3061422 B1 | 11/2021 |
| EP | 3107500 B1 | 11/2021 |
| EP | 3110468 B1 | 11/2021 |
| EP | 3154474 B1 | 11/2021 |
| EP | 3213715 B1 | 11/2021 |
| EP | 3288499 B1 | 11/2021 |
| EP | 3360514 B1 | 11/2021 |

(56) References Cited

FOREIGN PATENT DOCUMENTS

| | | | |
|---|---|---|---|
| EP | 3429507 B1 | 11/2021 |
| EP | 3445443 B1 | 11/2021 |
| EP | 3454785 B1 | 11/2021 |
| EP | 3505077 B1 | 11/2021 |
| EP | 3672529 B1 | 11/2021 |
| EP | 3760164 B1 | 11/2021 |
| EP | 2358307 B1 | 12/2021 |
| EP | 2765954 B1 | 12/2021 |
| EP | 2991584 B1 | 12/2021 |
| EP | 3283011 B1 | 12/2021 |
| EP | 3288479 B1 | 12/2021 |
| EP | 3344167 B1 | 12/2021 |
| EP | 3410987 B1 | 12/2021 |
| EP | 3481339 B1 | 12/2021 |
| EP | 3482718 B1 | 12/2021 |
| EP | 3490465 B1 | 12/2021 |
| EP | 3498224 B1 | 12/2021 |
| EP | 3503846 B1 | 12/2021 |
| EP | 3592284 B1 | 12/2021 |
| EP | 3749254 B1 | 12/2021 |
| FR | 2815844 B1 | 1/2003 |
| FR | 2826863 B1 | 9/2003 |
| FR | 2828091 B1 | 11/2003 |
| FR | 2847800 B1 | 10/2005 |
| FR | 2858543 B1 | 2/2006 |
| FR | 2828263 B1 | 5/2007 |
| FR | 2874812 B1 | 6/2007 |
| FR | 2874813 B1 | 6/2007 |
| FR | 2883721 B1 | 6/2007 |
| FR | 2894131 B1 | 12/2008 |
| FR | 2899096 B1 | 12/2008 |
| FR | 2910269 B1 | 2/2009 |
| FR | 2909857 B1 | 3/2009 |
| FR | 2906454 B1 | 4/2009 |
| FR | 2906998 B1 | 4/2009 |
| FR | 2913879 B1 | 6/2009 |
| FR | 2916959 B1 | 9/2009 |
| FR | 2892939 B1 | 1/2010 |
| FR | 2915678 B1 | 4/2010 |
| FR | 2930137 B1 | 4/2010 |
| FR | 2915903 B1 | 6/2010 |
| FR | 2916627 B1 | 9/2010 |
| FR | 2920664 B1 | 9/2010 |
| FR | 2932376 B1 | 4/2011 |
| FR | 2947716 B1 | 9/2011 |
| FR | 2945440 B1 | 12/2012 |
| FR | 2951549 B1 | 8/2013 |
| FR | 2964855 B1 | 10/2013 |
| FR | 2977792 B1 | 10/2013 |
| FR | 2980968 B1 | 12/2013 |
| FR | 2986149 B1 | 12/2014 |
| FR | 2997288 B1 | 1/2015 |
| FR | 2998167 B1 | 1/2015 |
| FR | 2996747 B1 | 2/2015 |
| FR | 2996748 B1 | 2/2015 |
| FR | 3004638 B1 | 5/2015 |
| FR | 2982763 B1 | 7/2015 |
| FR | 2991162 B1 | 7/2015 |
| FR | 3006582 B1 | 7/2015 |
| FR | 3001121 B1 | 1/2016 |
| FR | 2998166 B1 | 2/2016 |
| FR | 3021862 B1 | 5/2016 |
| FR | 3004917 B1 | 6/2016 |
| FR | 3006884 B1 | 6/2016 |
| FR | 3023704 B1 | 8/2016 |
| FR | 3008885 B1 | 12/2016 |
| FR | 3033494 B1 | 3/2017 |
| FR | 3057154 B1 | 10/2018 |
| FR | 3058631 B1 | 1/2019 |
| FR | 3058632 B1 | 1/2019 |
| FR | 3060292 B1 | 1/2019 |
| FR | 3063631 B1 | 3/2019 |
| FR | 3020265 B1 | 9/2019 |
| FR | 3072013 B1 | 9/2019 |
| GB | 243370 A | 8/1926 |
| GB | 2407146 B | 4/2006 |
| GB | 2398245 B | 3/2007 |
| GB | 2433700 B | 12/2007 |
| GB | 2478498 B | 7/2012 |
| GB | 2530487 B | 12/2016 |
| GB | 2517609 B | 5/2017 |
| GB | 2538749 B | 8/2017 |
| GB | 2538072 B | 11/2017 |
| GB | 2536538 B | 7/2018 |
| GB | 2548891 B | 7/2018 |
| WO | WO-2020257643 A1 | 12/2020 |

OTHER PUBLICATIONS

"International Application Serial No. PCT/US2020/038726, Written Opinion dated Nov. 6, 2020", 7 pgs.
"International Application Serial No. PCT/US2020/038726, Invitation to Pay Additional Fees mailed Aug. 25, 20", 2 pgs.
"International Application Serial No. PCT/US2020/038726, International Preliminary Report on Patentability dated Dec. 30, 21", 9 pgs.

* cited by examiner

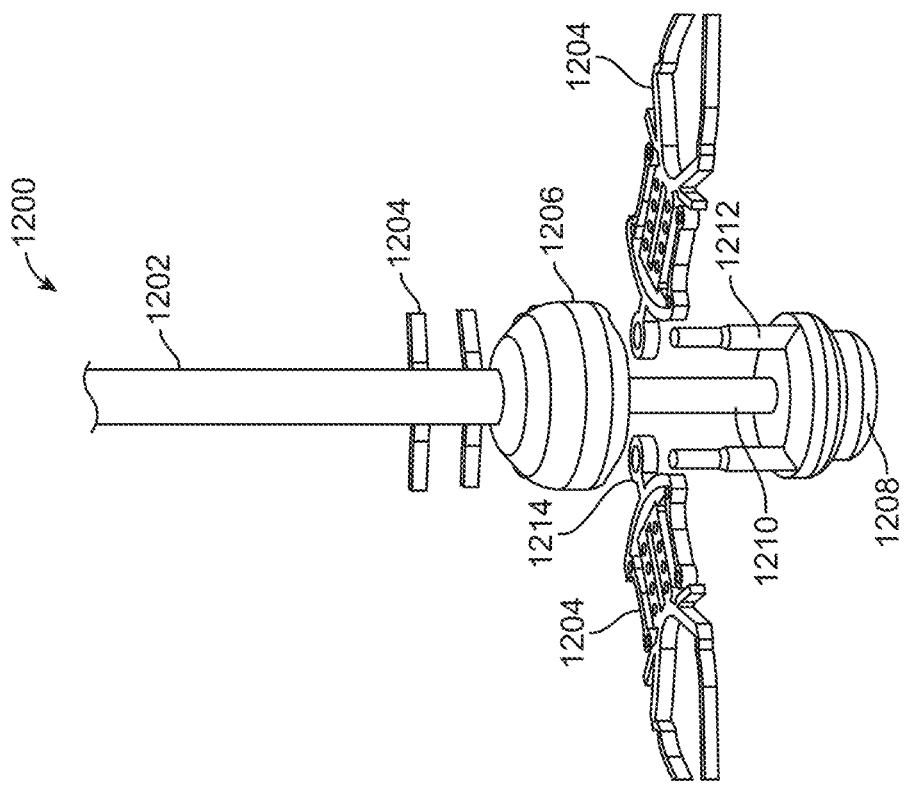
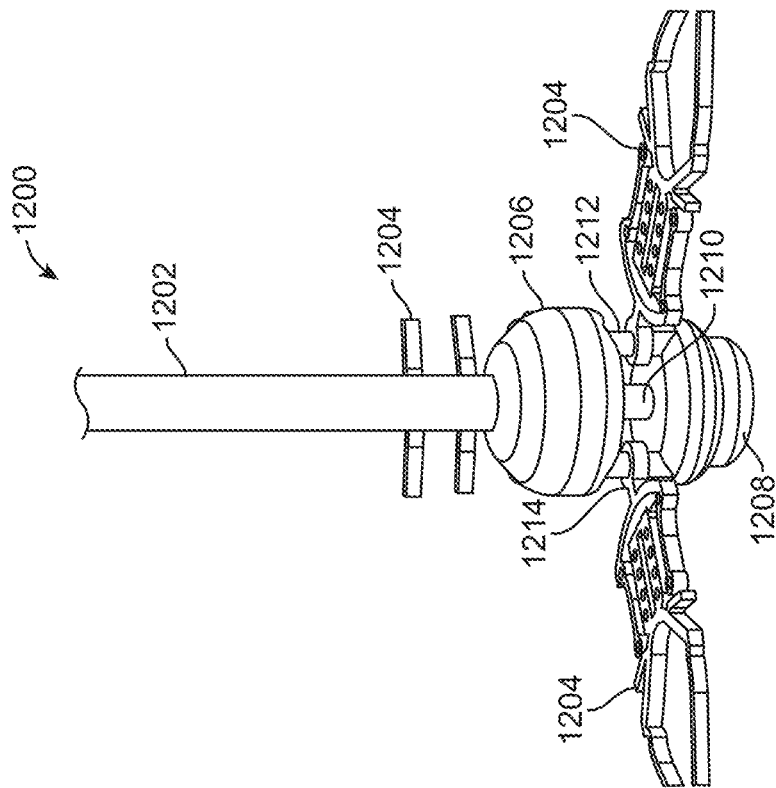

LOW PROFILE PROSTHETIC MITRAL VALVE

CLAIM OF PRIORITY

The present application is a non-provisional of, and claims the benefit of U.S. Provisional Patent Application No. 62/864,008 filed on Jun. 20, 2019; the entire contents of which are incorporated herein by reference.

BACKGROUND

Mitral valve regurgitation, also known as mitral incompetence, is a serious cardiac condition where the mitral valve fails to properly close and prevent retrograde blood flow across the native mitral valve. This condition can compromise cardiac function and can be debilitating or life threatening.

Current treatments for mitral insufficiency include traditional surgical repair of the native valve. Less invasive transcatheter treatments are being developed.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 12A-12B show a locking mechanism for releasably coupling a prosthetic valve with a delivery catheter.

DETAILED DESCRIPTION

Traditional surgical repair of the mitral valve can be an effective treatment but requires open heart surgery, a long hospitalization and recovery period. Less invasive transcatheter treatments are being developed and are promising but can be challenging to implant and many have not received regulatory approval for commercial distribution. Therefore, there is a need for improved devices to treat mitral insufficiency. At least some of these challenges are addressed by the examples disclosed herein.

While the examples disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc., as well as other valves in the body such as venous valves or any anatomical structure which is used to control the flow of fluids or other materials.

Cardiac Anatomy.

Figure 1:
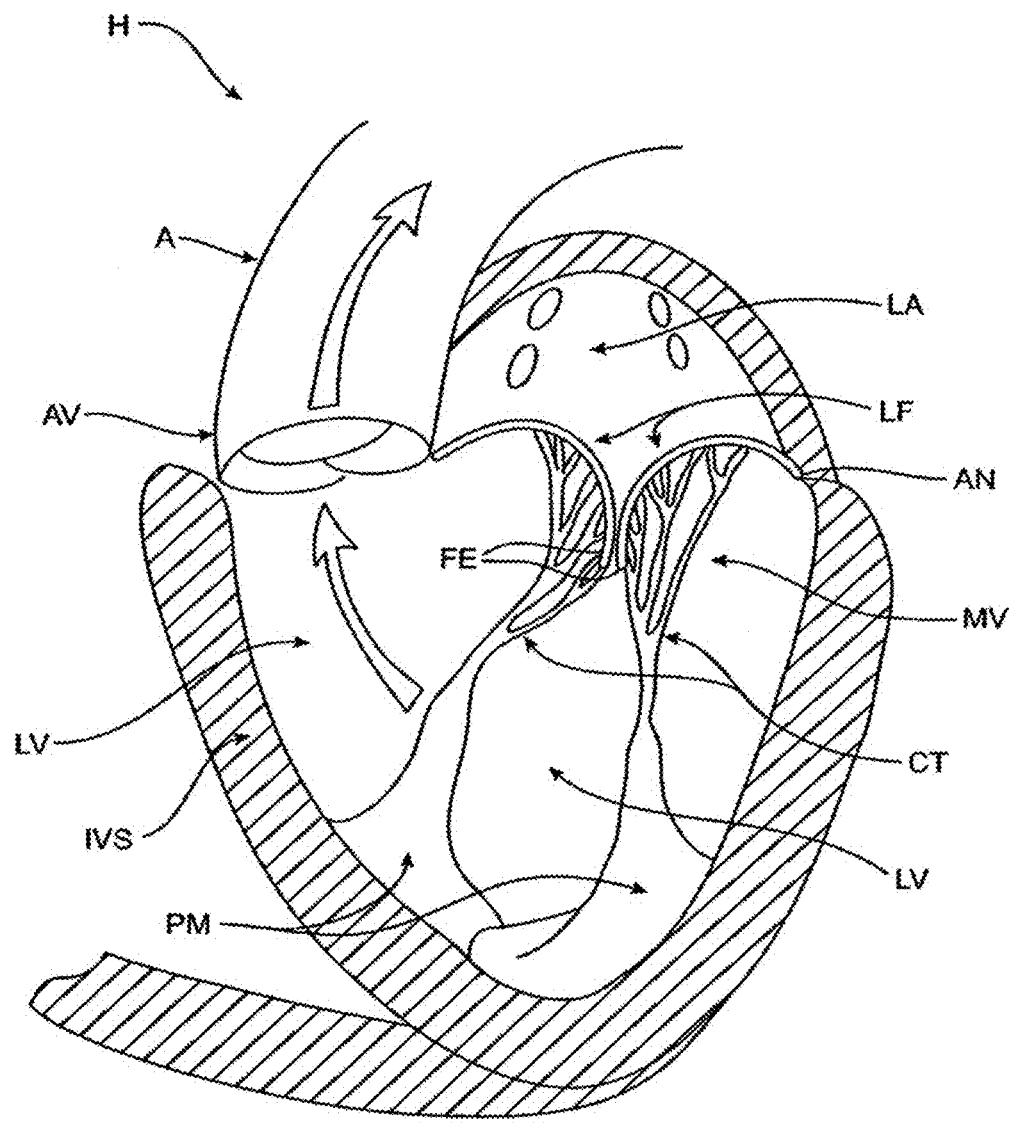
FIG. 1 is a schematic illustration of the left ventricle of a heart showing blood flow during systole.

The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
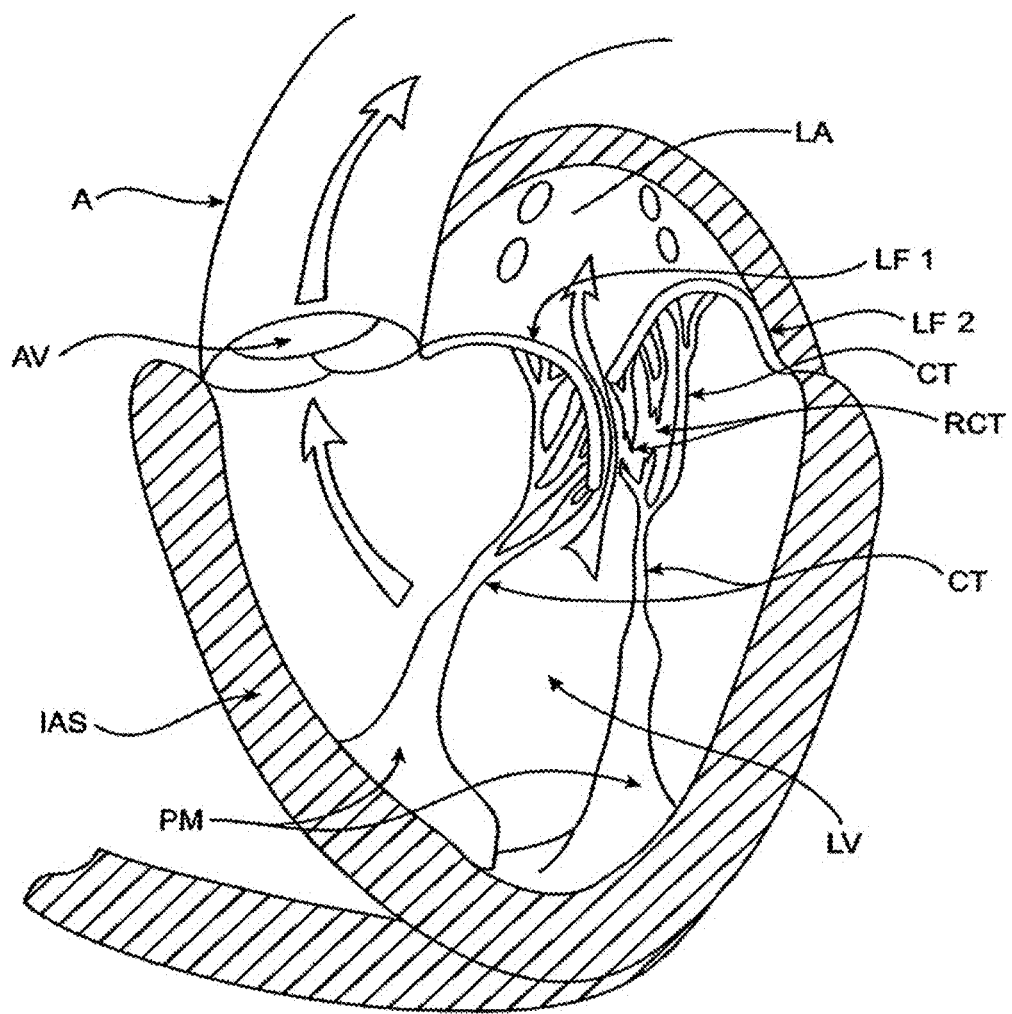
FIG. 2 is a schematic illustration of the left ventricle of a heart having prolapsed leaflets in the mitral valve.
Figure 3A:
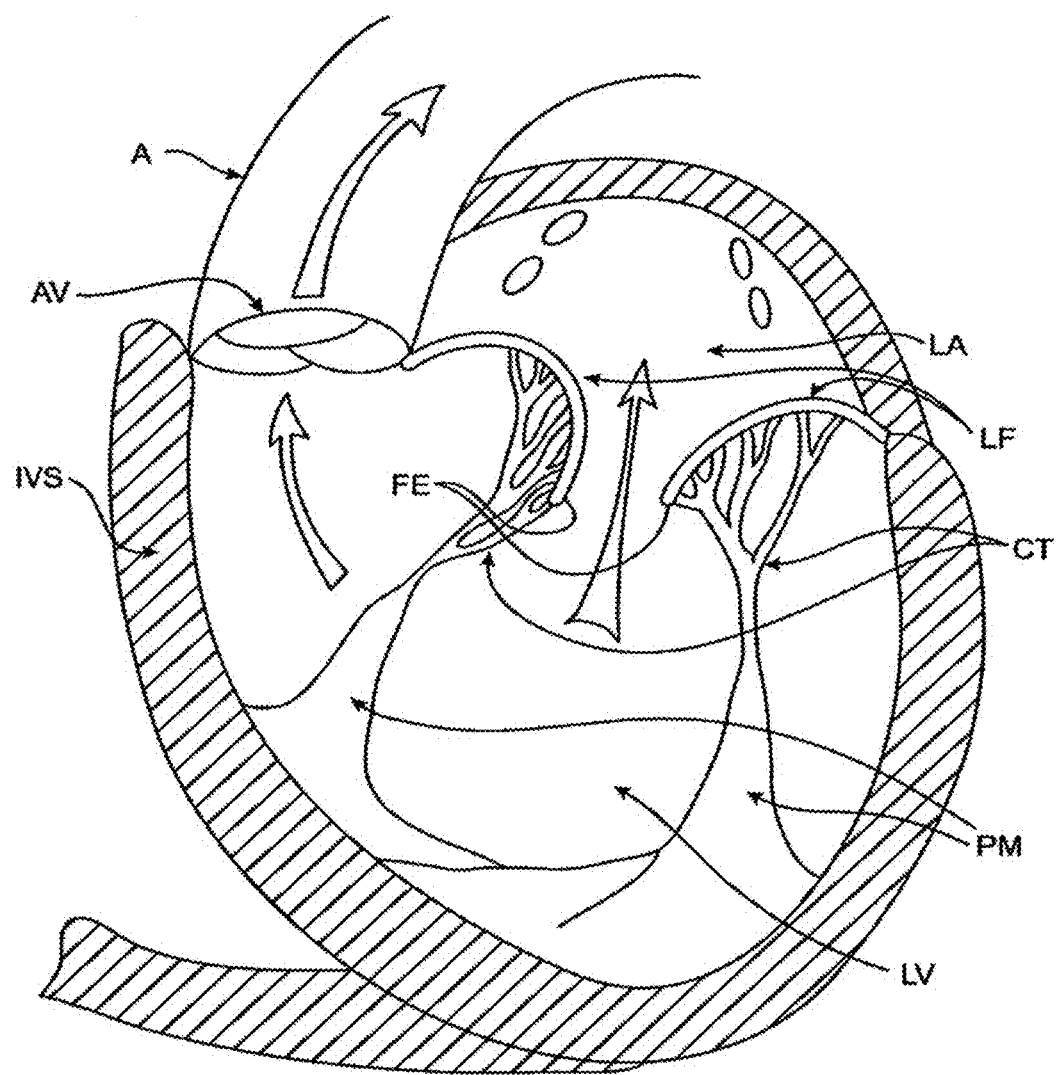
FIG. 3A is a schematic illustration of a heart in a patient suffering from cardiomyopathy where the heart is dilated, and the leaflets do not meet.
Figure 3B:
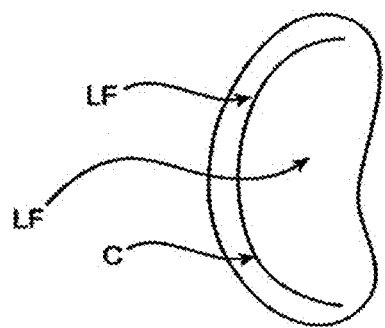
FIG. 3B shows, normal closure of the leaflets.
Figure 3C:
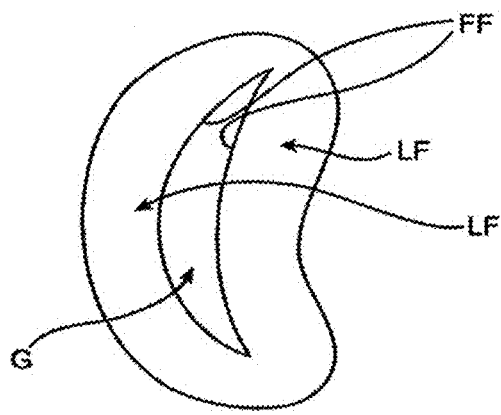
FIG. 3C shows abnormal closure in the dilated heart.
Figure 4:
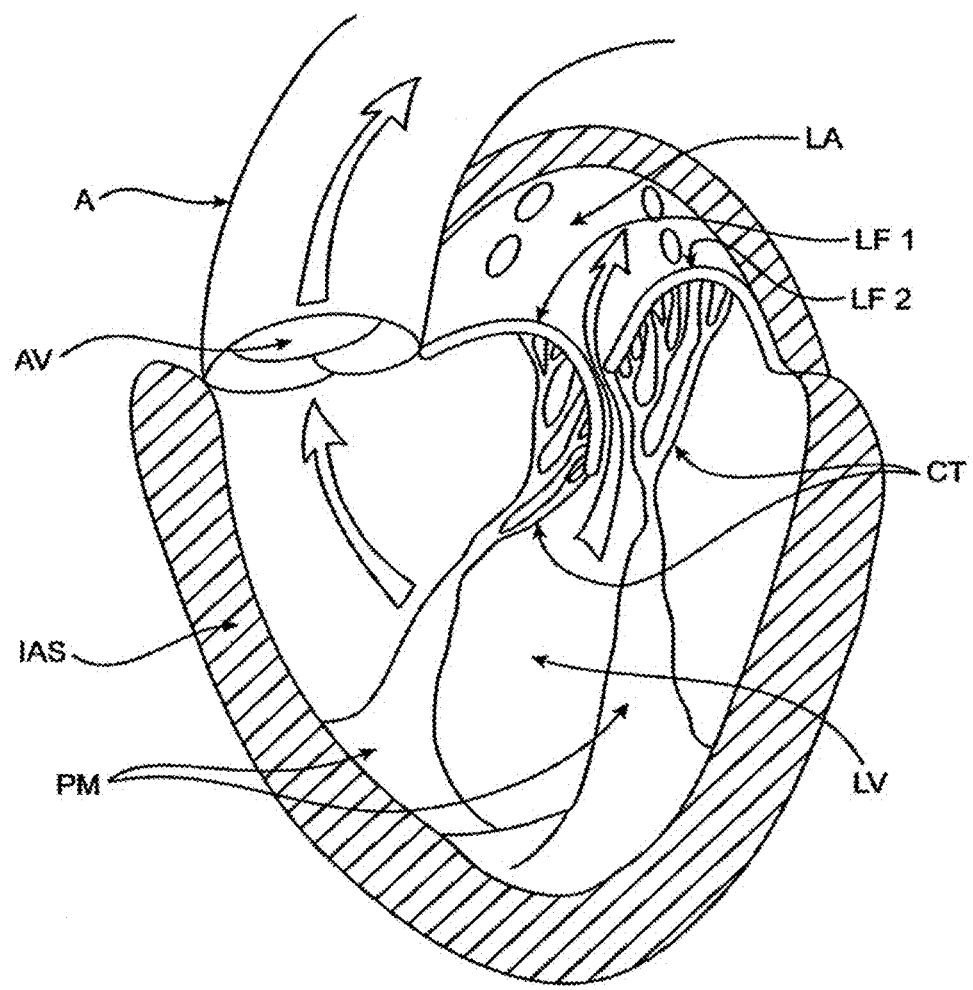
FIG. 4 illustrates mitral valve regurgitation in the left ventricle of a heart having impaired papillary muscles.

Referring now to FIGS. 2-4, a number of structural defects in the heart can cause mitral prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Regurgitation also occurs in the patients suffering from cardiomyopathy where the heart is dilated and the increased size prevents the valve leaflets LF from meeting properly, as shown in FIG. 3A. The enlargement of the heart causes the mitral annulus to become enlarged, making it impossible for the free edges FE to meet during systole. The free edges of the anterior and posterior leaflets normally meet along a line of coaptation C as shown in FIG. 3B, but a significant gap G can be left in patients suffering from cardiomyopathy, as shown in FIG. 3C.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
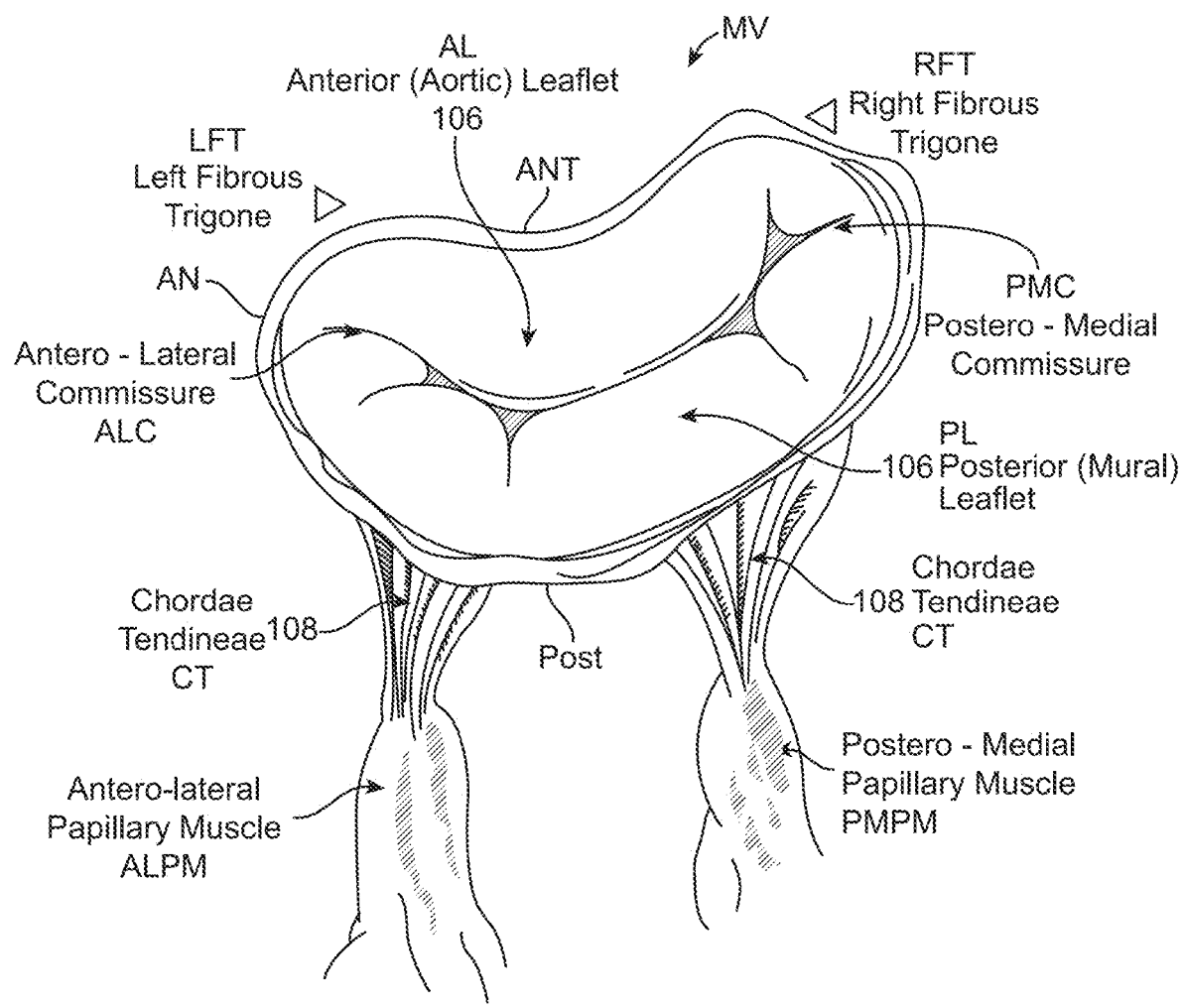
FIGS. 5A-5B illustrate the anatomy of the mitral valve.
Figure 5B:
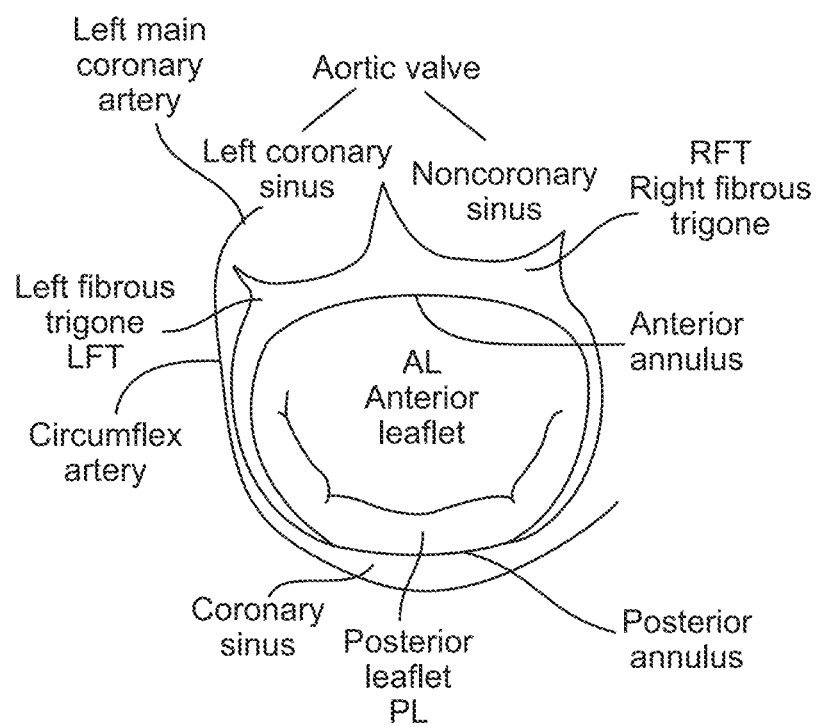

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted by generally by the solid triangles. FIG. 5B more clearly illustrates the left and right fibrous trigones, LFT, RFT.

Prosthetic Valve

Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the prosthetic valve to the patient's heart, and a valve mechanism coupled to the anchor. The valve mechanism often is either a mechanical valve, a valve with animal tissue, or combinations thereof. The prosthetic valve once implanted, takes over for the malfunctioning native valve, thereby reducing or eliminating valvar insufficiency. Some of these valves are challenging to deliver and some are difficult to accurately anchor. Others are large in size which can obstruct the chambers of the heart. While some of these valves appear promising, there still is a need for improved valves that address at least some of these challenges. The following specification discloses examples of a prosthetic valve, a delivery system for the prosthetic valve, and methods of delivering the valve that may overcome some of the challenges associated with existing prosthetic valves.

Figure 6A:
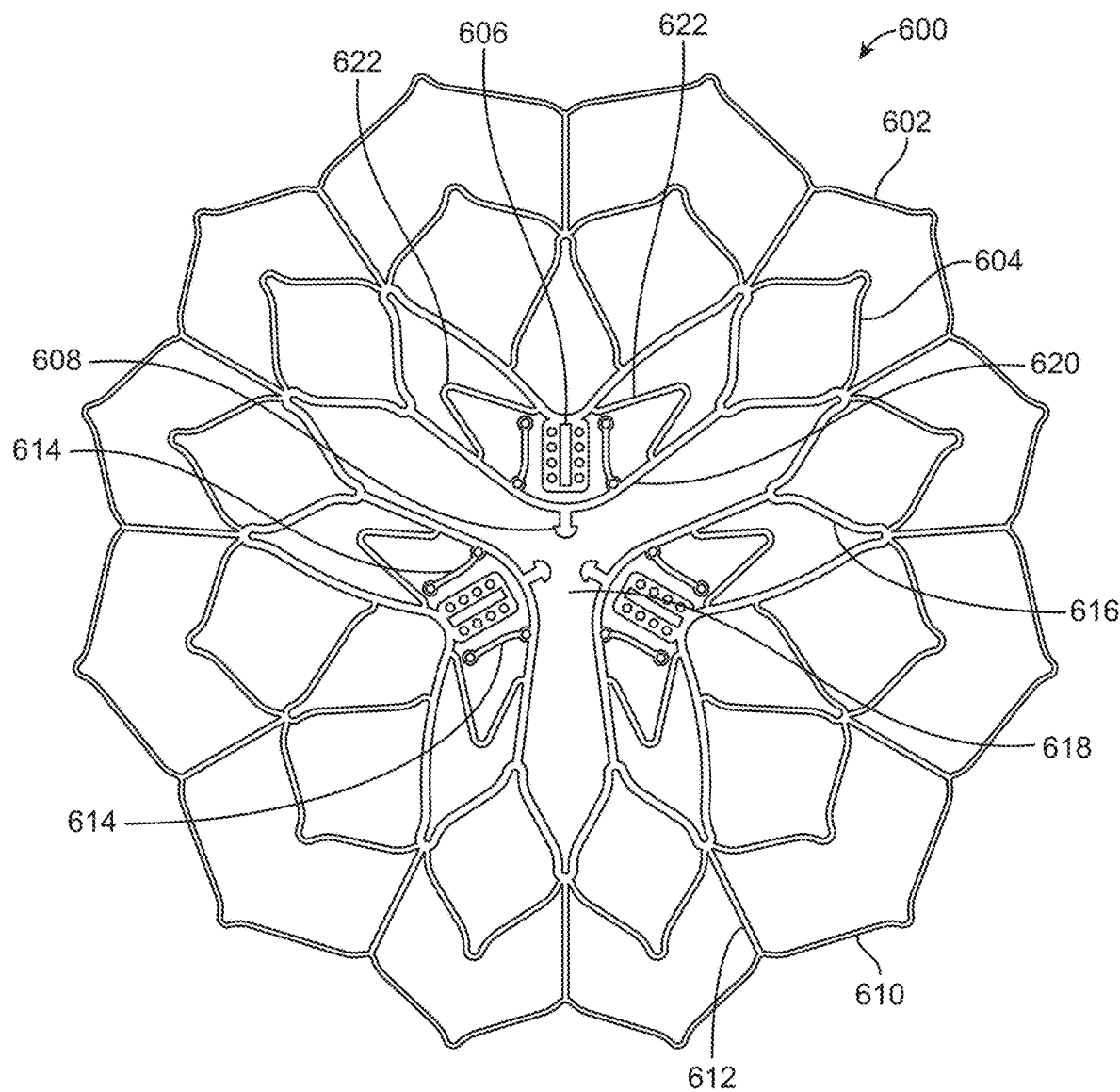
FIG. 6A shows a top view of an example of a low-profile prosthetic valve.

FIG. 6A illustrates an example of a low profile prosthetic mitral valve 600 shown in a flat cut view. The prosthetic mitral valve 600 is an expandable frame formed from a plurality of interconnected struts and may be cut from a flat sheet of material such as stainless steel, nitinol or other biocompatible materials. It may be balloon expandable or self-expanding. The expandable frame is in a flat planar configuration after cutting from the sheet of material and may be heat treated and shape set into a desired shape as will be discussed below. The flat pattern includes a plurality of concentric annular rings 602, 604 that are formed from a plurality of struts which extend around the circumference of the prosthesis. Rings are smaller in diameter and circumference as they get closer to the center of the prosthetic valve. Thus ring 602 has a larger diameter and larger circumference than ring 604. Adjacent rings are coupled together with a plurality of radially extending struts 612 to form a plurality of closed cells circumferentially disposed around the prosthetic valve with adjacent closed cells sharing at least one common strut. Each ring 602, 604 may include a plurality of circumferentially oriented struts that all have the same geometry. For example, outer-most ring 602 includes a plurality of wishbone shaped struts coupled together to form the annular ring. The wishbone shaped struts may all be the same in ring 602 and they may include two oppositely sloped struts that are coupled together with an arcuate strut that forms a protuberance or peak in the wishbone shaped strut at the inflection point between the two oppositely sloped struts.

The next adjacent ring 604 disposed radially inward from ring 602 is similarly formed with a plurality of wishbone shaped struts coupled together. The wishbone shaped struts in ring 604 may all be the same in ring 604 and they may be similarly formed from two oppositely sloped struts that are coupled together with an arcuate strut that forms a protuberance or peak in the wishbone shaped strut at the inflection point between the two oppositely sloped struts. The sizes and angles of the struts in ring 604 may be different than ring 602 since the two rings are concentric with one another and therefore ring 604 has a smaller diameter and circumference than outer ring 602. A plurality of linear struts 612 that extend radially outward from the center of the prosthesis couple rings 602 and 604 together to form closed cells 610. The closed cells 610 formed between ring 602 and 604 may all have the same geometry, or they may vary.

Struts may be wishbone shaped in order to divert stress and strain away from the apex of the wishbone thereby allowing a greater angular range of motion to be achieved for a given maximum strain, or allowing a lower maximum strain to occur for the same given range of motion.

A Y-shaped strut 616 is coupled to the wishbone shaped second ring 604 with the tail of the Y extending radially inward toward the center of the prosthesis, thereby forming a lemon shaped closed cell with a peak and valley on opposite sides of the closed cell, and pointed ends on the two other sides of the closed cell. The tails of the Y may be coupled together to define a central aperture 618 in the prosthesis. In this example, the central aperture 618 is star shaped with three pointed arms extending radially outward to form the star shape.

A plurality of inner closed cells 620, here three closed cells 620, are formed by two V-shaped struts 622 on opposite sides of the closed cell 620 coupled to the tails of adjacent Y-shaped struts 616 to form the closed cells 620. Each closed cell 620 contains a commissure tab 606 and two ventricular anchor struts 614

Commissure tabs 606 may be adjacent the center of the prosthesis and may include a plurality of suture holes so that the prosthetic valve leaflets may be sutured to the commissure tabs. The commissure tabs 606 may be a rectangular shaped strut with a slit through the middle for receiving prosthetic leaflets. In this example there are three prosthetic valve leaflets (not shown) attached to the commissure tabs forming a tricuspid prosthetic valve. The prosthetic valve leaflets are not illustrated for ease in viewing the expandable frame. The commissure tabs are disposed in between struts 614 which form ventricular anchor tabs that anchor the prosthesis to a ventricular portion of the native valve, such as an anterior portion of the native valve (such as the fibrous trigones) and a posterior portion of the native valve. Struts 614 form part of the ventricular anchors. Two struts 614 are disposed on either side of the commissure tabs 606. One end of strut 614 is coupled to a tail of the Y-shaped strut 616, and the opposite end of struts 614 is a free end that may be bend radially outward. The free end may include a through hole which is used for attachment of a cover (not shown). The cover may be any material such as a polymer like Dacron, and forms a foot which is a soft atraumatic tip for engaging tissue. The Dacron or other polymer cover material provides greater surface area and therefore reduces the chance of the ventricular anchor tabs piercing tissue. The ventricular tabs can then angulate away from the valve frame during expansion to allow anchoring on the fibrous trigones or any other anterior portion of the ventricular side of the native valve, or any portion on the posterior annulus of the native valve.

Facing radially inward toward the center of the device may be a plurality of anchor tabs 608, here mushroom head shaped tabs 608 or T-shaped heads, which allow the prosthesis to be coupled to a delivery catheter as will be described below. In this or any other example, the T-shaped or mushroom head anchor tabs may be omitted and simply have an aperture through the tab that allows a pin or other connector element to be disposed in the aperture for releasable coupling with a delivery catheter, as will be described in greater detail below. The anchor tabs 608 are disposed on a portion of strut that joins two tails of Y-shaped struts 616 together. Thus, in this example there are three connection points that may be made with a delivery catheter.

Figure 6B:
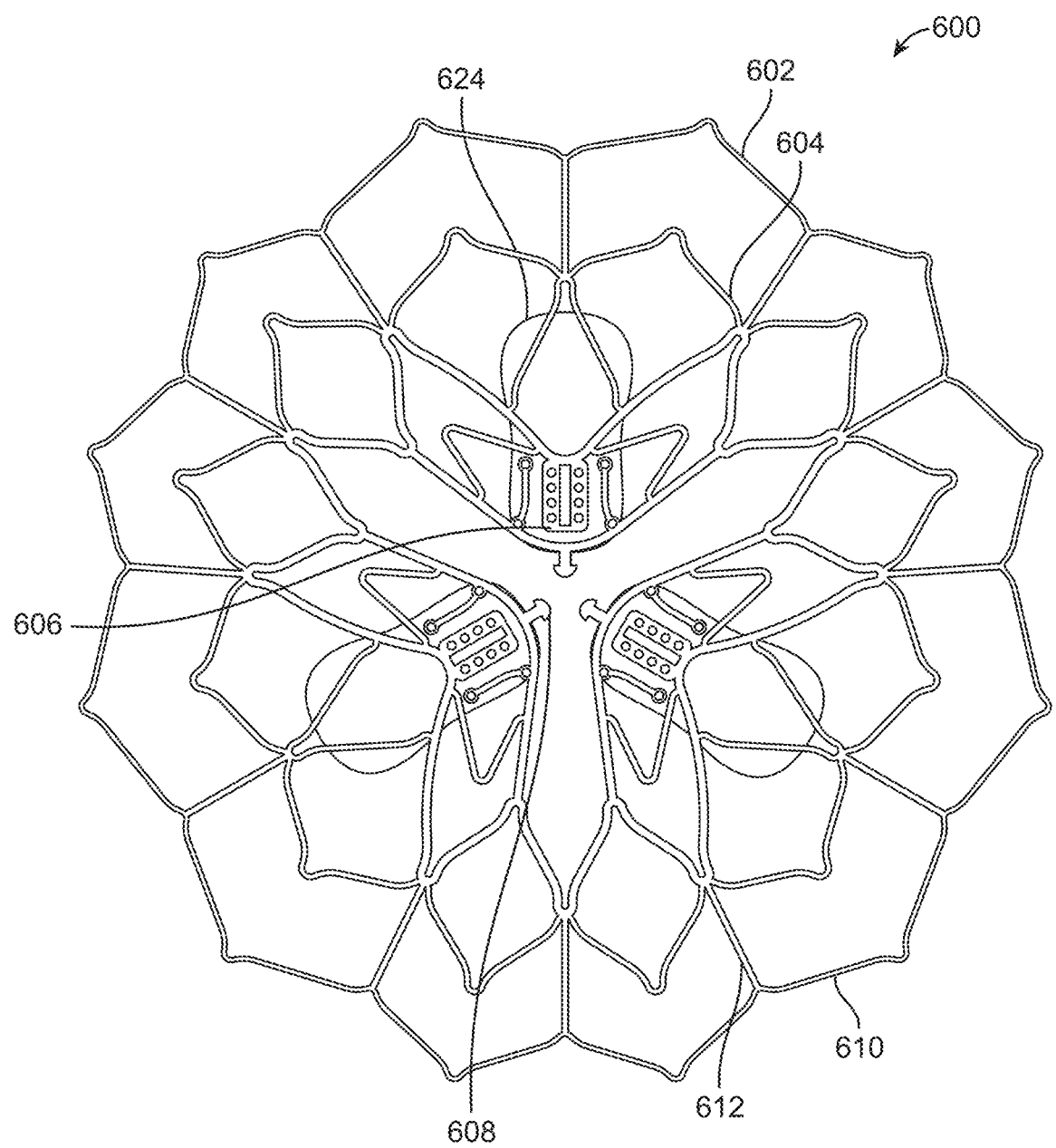
FIG. 6B shows the ventricular anchors of the example in FIG. 6A.

FIG. 6B illustrates prosthetic valve 600 with the cover 624 disposed over the struts 614 and prosthetic frame to form a foot which helps create the ventricular anchors. This is shown by the shaded regions. The foot includes an enlarged head region and a narrower body. Again, the enlarged head provides a larger surface area and therefore minimizes pressure applied to tissue during anchoring in order to eliminate or reduce tissue trauma. Other aspects of FIG. 6B are the same as FIG. 6A.

Figure 6C:
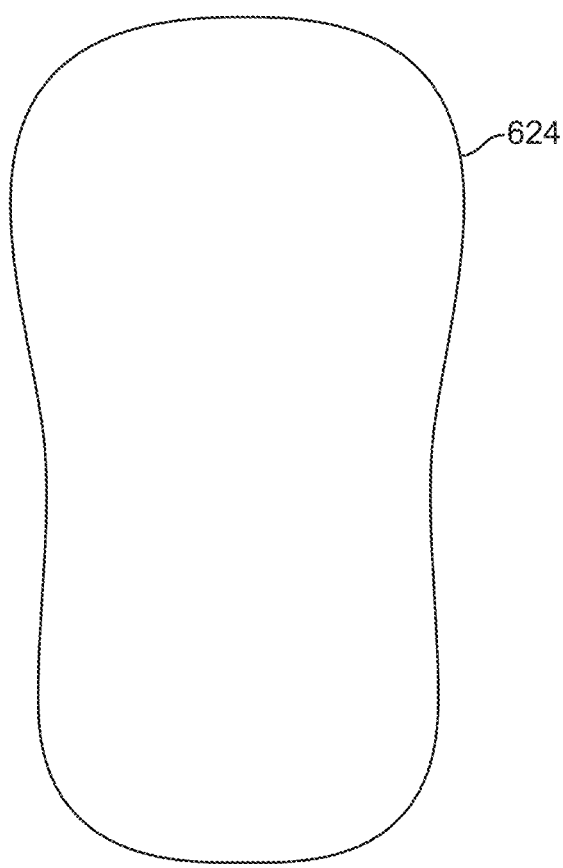
FIG. 6C shows a cover that may be attached to the ventricular anchors of the valve in FIG. 6A

FIG. 6C shows an example of a cover 624 that may be attached to struts 614 to form the atraumatic tip of the ventricular anchors. The cover may be Dacron, or another polymer, or any material that has the desired mechanical properties. Cover 624 has an enlarged head region and a thinner elongate body region. The enlarged head region provided greater surface area in order to reduce contact pressure with tissue during anchoring in order to eliminate or reduce tissue piercing and trauma.

Figure 6D:
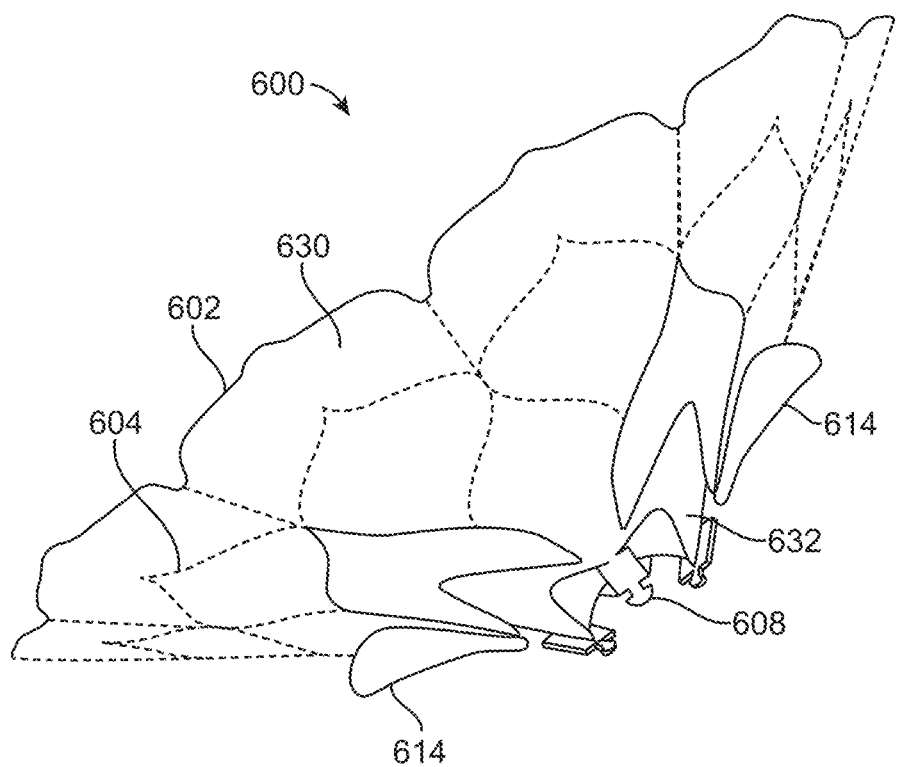
FIG. 6D shows a perspective view of the valve in FIG. 6A.

FIG. 6D is a perspective view of the prosthetic valve 600 shown in FIGS. 6A-6B but with the covering 630 shown disposed over the expandable frame and after shape setting. In addition to a covering disposed over the ventricular anchors 614 to form atraumatic anchor tabs, the same material or another material may be disposed over any or all of the struts and closed cells to minimize perivalvular leakage and promote tissue ingrowth. FIG. 6D shows the prosthetic valve 600 in the fully expanded configuration after shape setting, where the prosthesis is flared upward in an atrial direction (or tapered in a ventricular direction) and the upper atrial end which is the inflow end of the prosthesis is the largest diameter and the valve tapers down to a smaller diameter on the ventricular end which is the outflow end. The funnel shape of the frame may also be described as parabaloidal-like with the concave portion of the paraboloid facing up toward the atrium and the convex portion of the paraboloid facing downward toward the ventricle. The prosthetic valve has an intermediate expanded configuration where the paraboloid is inverted so that the prosthesis flares outward from the upper to lower ends so the flaring is in the direction of the ventricle or the tapering is in the direction of the atrium. If paraboloid shaped, then and the concave portion of the paraboloid faces downward toward the ventricle while the convex portion of the paraboloid faces upward toward the atrium. This intermediate expanded configuration is illustrated and described in greater detail below. Prosthetic valve 600 also includes three commissure posts with three prosthetic valve leaflets 632 coupled to the commissure posts to form the prosthetic valve mechanism.

Figure 7A:
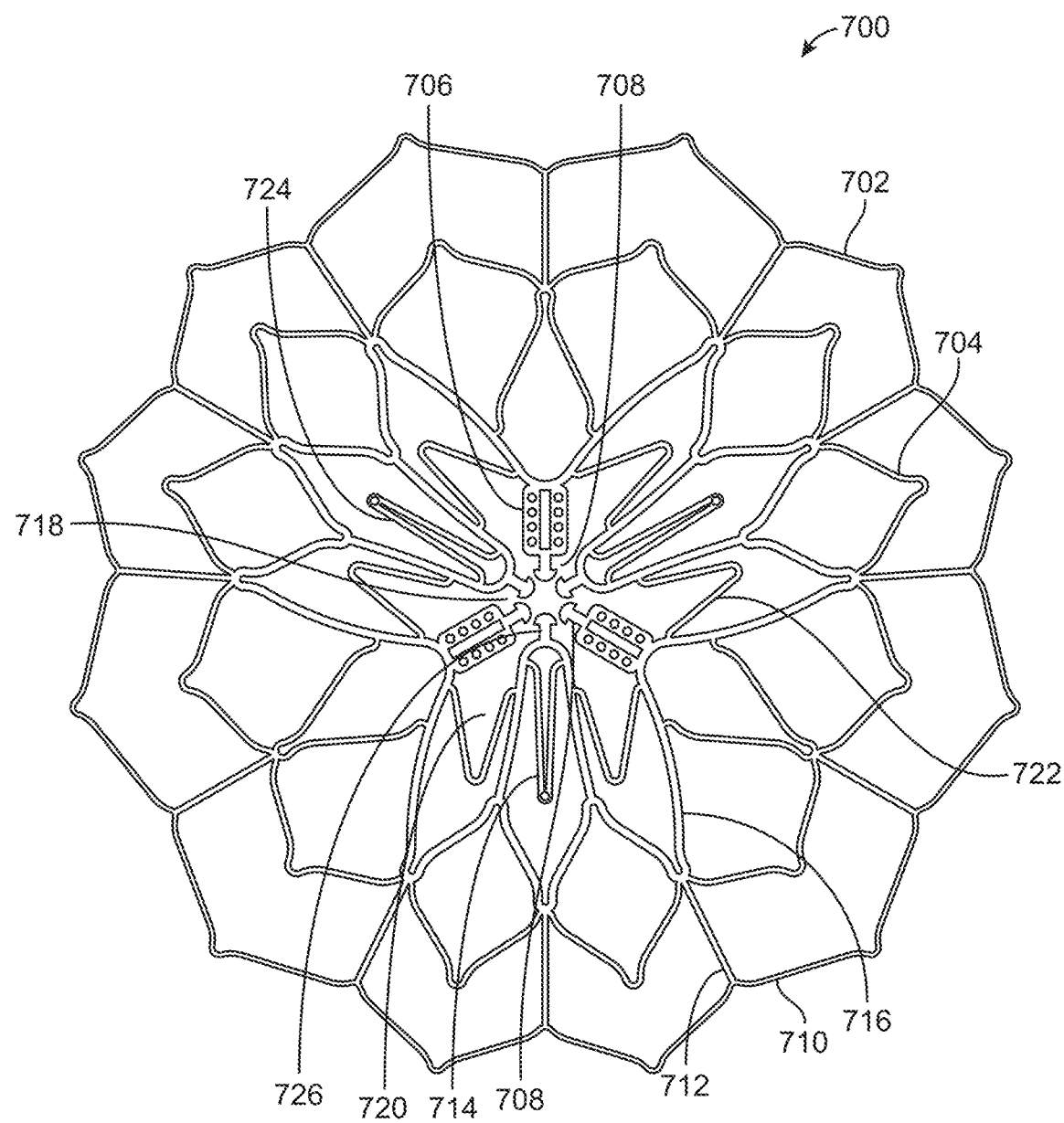
FIG. 7A shows a top view of another example of a low-profile prosthetic valve.

FIG. 7A illustrates an example of a low profile prosthetic mitral valve 700 shown in a flat cut view. The prosthetic mitral valve 700 is an expandable frame formed from a plurality of interconnected struts and may be cut from a flat sheet of material such as stainless steel, nitinol or other biocompatible materials. It may be balloon expandable or self-expanding. The expandable frame is in a flat planar configuration after cutting from the sheet of material and may be heat treated and shape set into a desired shape as will be discussed below. The flat pattern includes a plurality of concentric annular rings 702, 704 that are formed from a plurality of struts which extend around the circumference of the prosthesis. Rings are smaller in diameter and circumference as they get closer to the center of the prosthetic valve. Thus ring 702 has a larger diameter and larger circumference than ring 704. Adjacent rings are coupled together with a plurality of radially extending struts 712 to form a plurality of closed cells circumferentially disposed around the prosthetic valve with adjacent closed cells sharing at least one common strut. Each ring 702, 704 may include a plurality of circumferentially oriented struts that all have the same geometry. For example, outer-most ring 702 includes a plurality of wishbone shaped struts coupled together to form the annular ring. The wishbone shaped struts may all be the same in ring 702 and they may include two oppositely sloped struts that are coupled together with an arcuate strut that forms a protuberance or peak in the wishbone shaped strut at the inflection point between the two oppositely sloped struts.

The next adjacent ring 704 disposed radially inward from ring 702 is similarly formed with a plurality of wishbone shaped struts coupled together. The wishbone shaped struts in ring 704 may all be the same in ring 704 and they may be similarly formed from two oppositely sloped struts that are coupled together with an arcuate strut that forms a protuberance or peak in the wishbone shaped strut at the inflection point between the two oppositely sloped struts. The sizes and angles of the struts in ring 704 may be different than ring 702 since the two rings are concentric with one another and therefore ring 704 has a smaller diameter and circumference than outer ring 702. A plurality of linear struts 712 that extend radially outward from the center of the prosthesis couple rings 702 and 704 together to form closed cells 710. The closed cells 710 formed between ring 702 and 704 may all have the same geometry, or they may vary. The construct of the connected struts making rings coupled together to form closed cells creates a lattice structure that once shape set provides a flower-like shape, for example similar to a daisy.

Struts may be wishbone shaped in order to divert stress and strain away from the apex of the wishbone thereby allowing a greater angular range of motion to be achieved for a given maximum strain, or allowing a lower maximum strain to occur for the same given range of motion.

A Y-shaped strut 716 is coupled to the wishbone shaped second ring 704 with the tail of the Y extending radially inward toward the center of the prosthesis, thereby forming several tear drop shaped closed cells with pointed ends on opposite sides of the tear drop shape as well as several lemon shaped closed cells which are substantially the same as in the example FIG. 6A. The tails of the Y may be coupled together with V-shaped struts to define an inner closed cell 720 with a central aperture 718 in the prosthesis. In this example, the central aperture 718 has a central circular hole with a plurality of pointed arms extending radially outward from the central circular hole.

Inner closed cell 720 is formed by V-shaped struts 722 coupled to the tails of adjacent Y-shaped struts 716 to form the closed cell 720. Closed cell 720 contains three commissure tabs 706 and extending radially outward from closed cell 720 are three V-shaped struts which form ventricular anchors 724 configured to engage a ventricular inferior surface of the native valve. The legs of the ventricular anchors may be coupled to the tails of the Y-shaped struts, and the apex of the V (or the trough of the V, or free end of the V) may include a hole extending therethrough sized to receive a suture so that a cover similar to the cover in FIG. 6C may be attached to the anchor to form an atraumatic tip.

Commissure tabs 706 may be adjacent the center of the prosthesis and may include a plurality of suture holes so that the prosthetic valve leaflets may be sutured to the commissure tabs. The commissure tabs 706 may be a rectangular shaped strut with a slit through the middle for receiving prosthetic leaflets. In this example there are three prosthetic valve leaflets (not shown) attached to the commissure tabs forming a tricuspid prosthetic valve. The prosthetic valve leaflets are not illustrated for ease in viewing the expandable frame. The commissure tabs are disposed in between adjacent ventricular anchors 724 that anchor the prosthesis to a ventricular portion of the native valve, such as an anterior portion of the native valve (such as the fibrous trigones) and a posterior portion of the native valve. The free end of the ventricular anchor may be bend radially outward. The free end may include a through hole which is used for attachment of a cover (not shown). The cover may be any material such as a polymer like Dacron, and forms a foot which is a soft atraumatic tip for engaging tissue. The Dacron or other polymer cover material provides greater surface area and therefore reduces the chance of the ventricular anchor tabs piercing tissue. The ventricular tabs can then angulate away from the valve frame during expansion to allow anchoring on the fibrous trigones or any other anterior portion of the ventricular side of the native valve, or any portion on the posterior annulus of the native valve.

Facing radially inward toward the center of the device may be a plurality of anchor tabs 708 coupled to the commissures 706, here mushroom head shaped tabs 708 or T-shaped heads, which allow the prosthesis to be coupled to a delivery catheter as will be described below. In addition to the three anchor tabs 708 on the commissures, three additional anchor tabs 726 are coupled to a strut that joins the tails of two adjacent Y-shaped struts 716 and anchor tabs 726 face radially inward toward the center of the prosthesis. Anchor tabs 726 may also be mushroom head shaped, or T-shaped, or other shapes. Both anchor tabs 708, 726 may be used to releasably couple the prosthesis with a delivery catheter. Thus, in this example there are six connection points that may be made with a delivery catheter. Other aspects of the example in FIG. 7A may be substantially similar to the example in FIG. 6A.

Figure 7B:
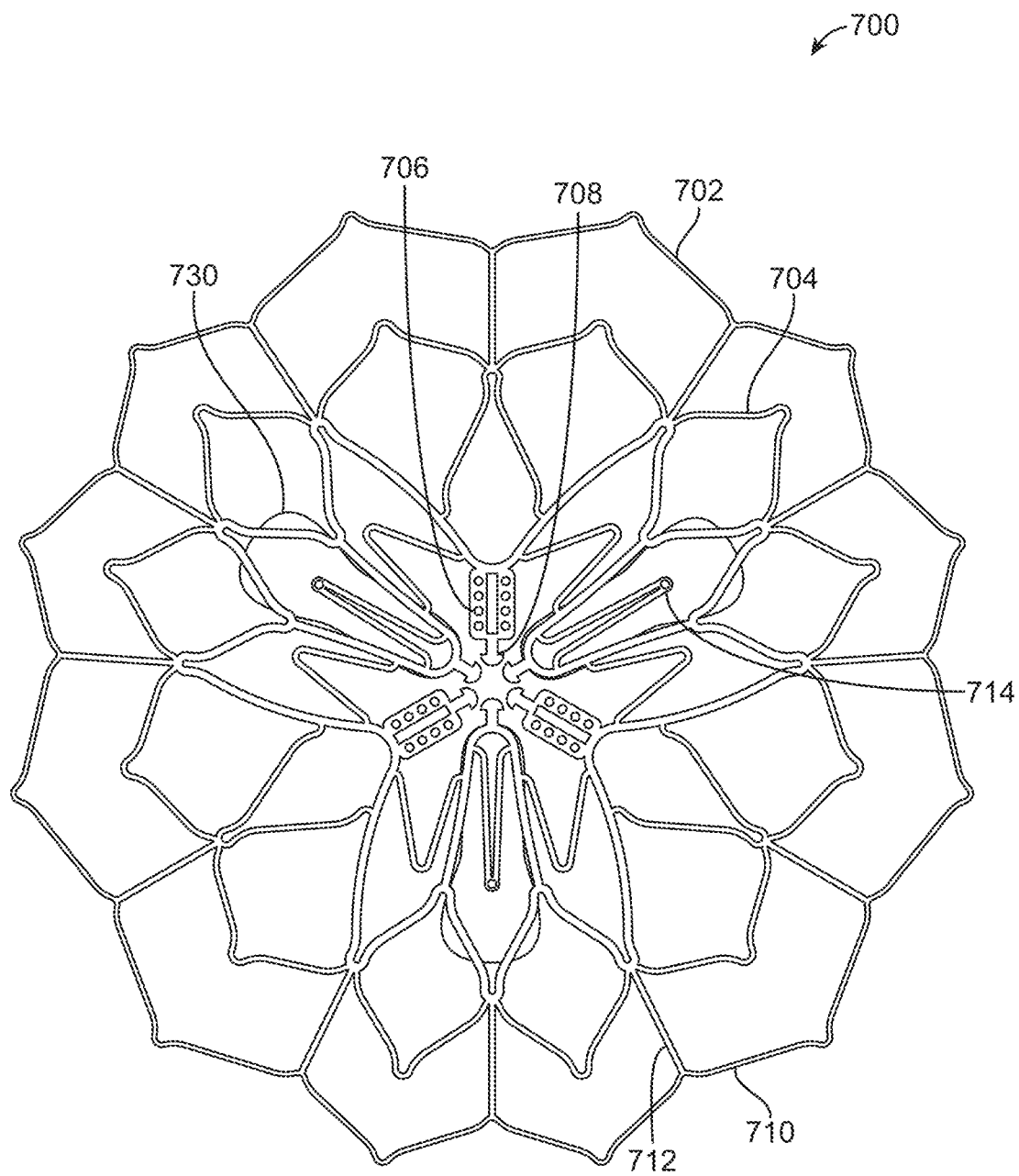
FIG. 7B shows the ventricular anchors of the example in FIG. 7A.

FIG. 7B illustrates prosthetic valve 700 with the cover 730 disposed over the ventricular anchors 714 and prosthetic frame to form a foot which helps create the ventricular anchors. The foot includes an enlarged head region and a narrower body. Again, the enlarged head provides a larger surface area and therefore minimizes pressure applied to tissue during anchoring in order to eliminate or reduce tissue trauma. Other aspects of FIG. 7B are the same as FIG. 7A.

Figure 7C:
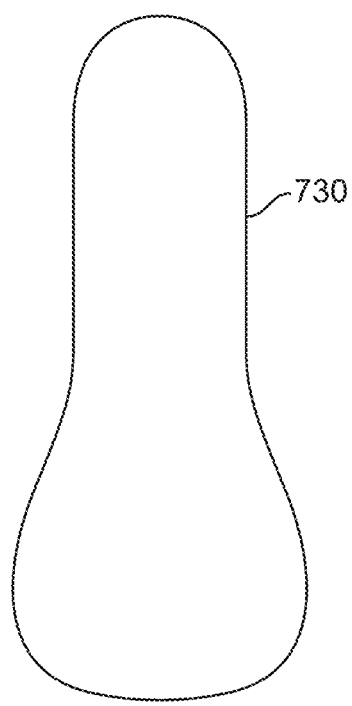
FIG. 7C shows an example of a cover that may be used on the ventricular anchors of FIG. 7B.

FIG. 7C shows an example of a cover 730 that may be attached to ventricular anchors 714 to form the atraumatic tip of the ventricular anchors. The cover may be Dacron, or another polymer, or any material that has the desired mechanical properties. Cover 730 has an enlarged head region and a thinner elongate body region. The enlarged head region provides greater surface area in order to reduce contact pressure with tissue during anchoring in order to eliminate or reduce tissue piercing and trauma.

Figure 7D:
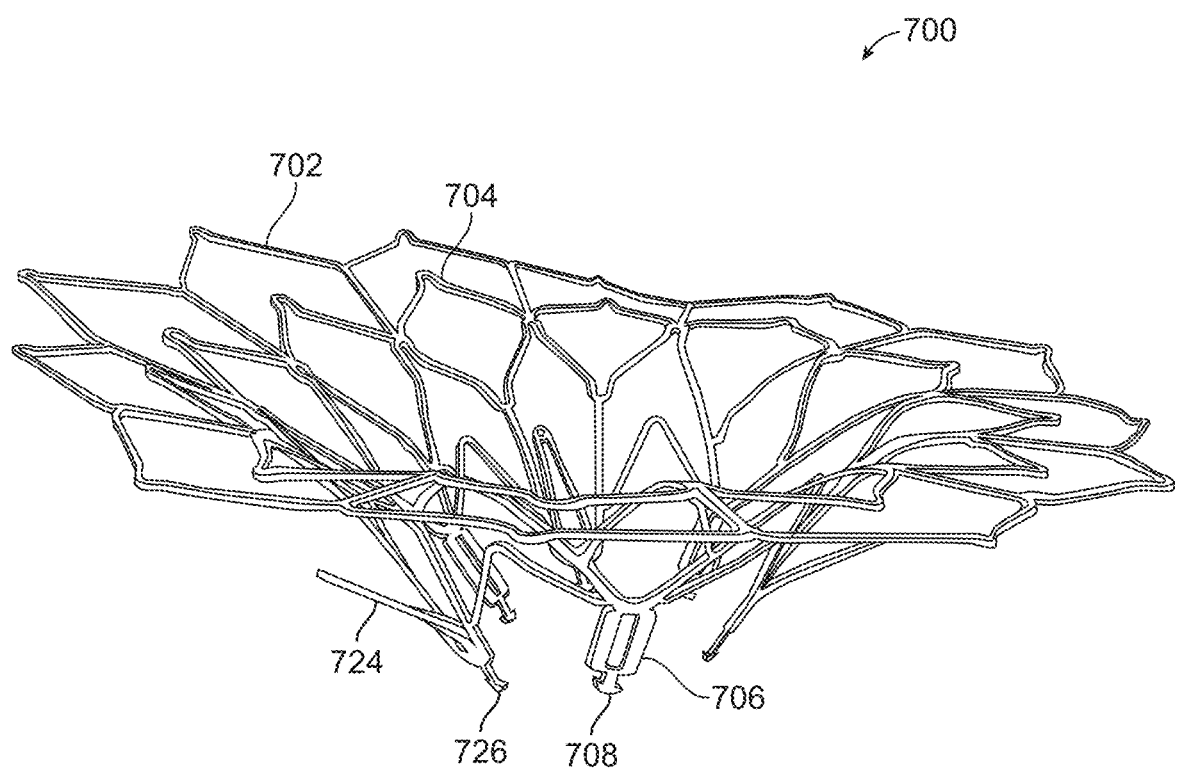
FIG. 7D shows a perspective view of the example in FIG. 7A.

FIG. 7D is a perspective view of the prosthetic valve 700 shown in FIGS. 7A-7B but with the covering removed for ease in viewing the struts of the expandable frame, and after shape setting. In addition to a covering disposed over the ventricular anchors, the same material or another material may be disposed over the any or all of the struts and closed cells. FIG. 7D shows the prosthetic valve 700 in the fully expanded configuration after shape setting, where the prosthesis flares in the atrial direction (or tapers toward the ventricle) and the upper atrial end which is the inflow end of the prosthesis is the largest diameter and the valve tapers down to a smaller diameter on the ventricular end which is the outflow end. The funnel shape of the frame may also be described as parabaloidal-like with the concave portion of the paraboloid facing up toward the atrium and the convex portion of the paraboloid facing downward toward the ventricle. The prosthetic valve has an intermediate expanded configuration where the prosthesis is tapered toward the atrium or flared toward the ventricle, and if paraboloid shaped, the paraboloid is inverted so that the prosthesis flares outward from the upper end to the lower end and the concave portion of the paraboloid faces downward toward the ventricle while the convex portion of the paraboloid faces upward toward the atrium. This intermediate expanded configuration is illustrated and described in greater detail below.

Figure 8A:
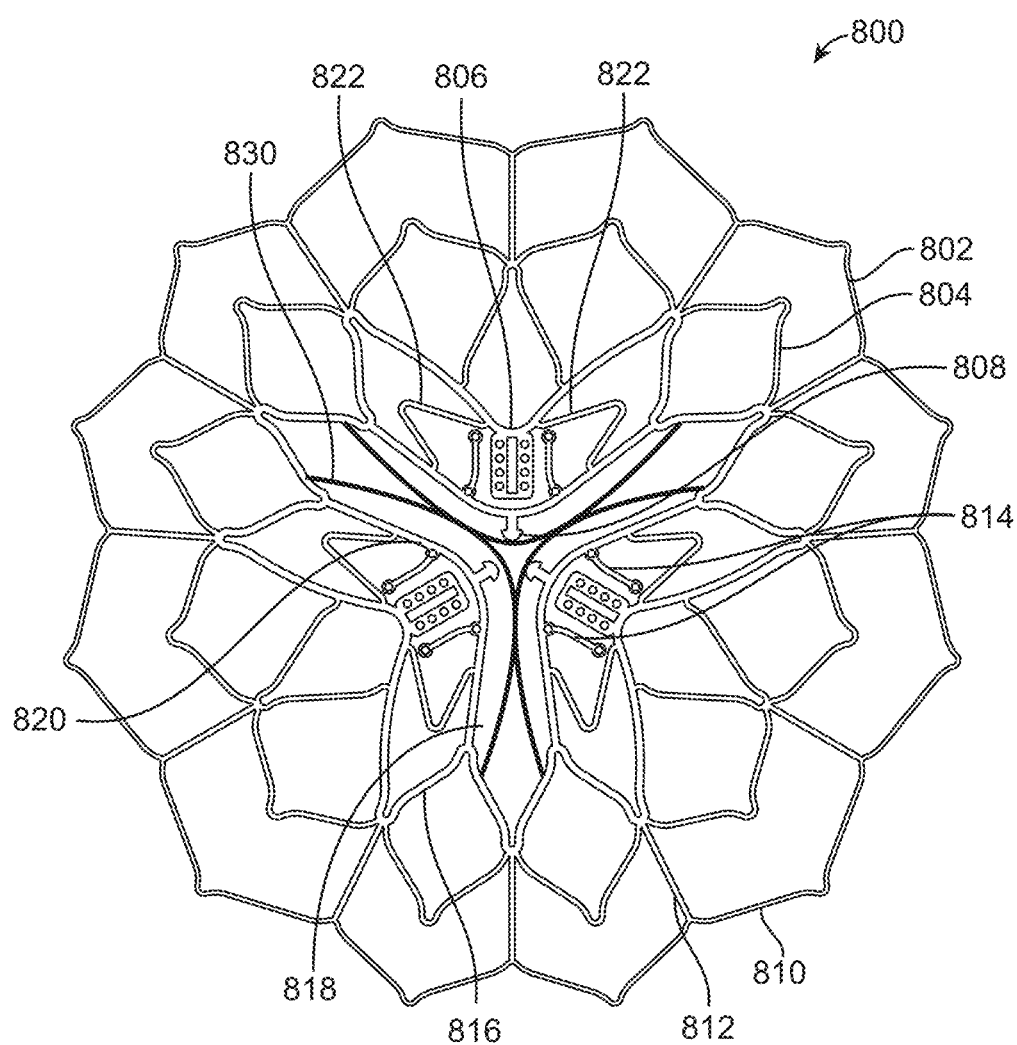
FIG. 8A shows a top view of another example of a low-profile prosthetic valve.

FIG. 8A illustrates another example of a low profile prosthetic mitral valve 800 shown in a flat cut view. Prosthetic valve 800 is substantially similar to the prosthetic valve 600 in FIGS. 6A-6D with the major difference being the addition of ventricular petals or wings 830 to help anchor the prosthesis to the ventricular side of the native valve and capture adjacent native valve leaflets. The prosthetic mitral valve 800 is an expandable frame formed from a plurality of interconnected struts and may be cut from a flat sheet of material such as stainless steel, nitinol or other biocompatible materials. It may be balloon expandable or self-expanding. The expandable frame is in a flat planar configuration after cutting from the sheet of material and may be heat treated and shape set into a desired shape as will be discussed below. The flat pattern includes a plurality of concentric annular rings 802, 804 that are formed from a plurality of struts which extend around the circumference of the prosthesis. Rings are smaller in diameter and circumference as they get closer to the center of the prosthetic valve. Thus ring 802 has a larger diameter and larger circumference than ring 804. Adjacent rings are coupled together with a plurality of radially extending struts 812 to form a plurality of closed cells circumferentially disposed around the prosthetic valve with adjacent closed cells sharing at least one common strut. Each ring 802, 804 may include a plurality of circumferentially oriented struts that all have the same geometry. For example, outer-most ring 802 includes a plurality of wishbone shaped struts coupled together to form the annular ring. The wishbone shaped struts may all be the same in ring 802 and they may include two oppositely sloped struts that are coupled together with an arcuate strut that forms a protuberance or peak in the wishbone shaped strut at the inflection point between the two oppositely sloped struts.

The next adjacent ring 804 disposed radially inward from ring 802 is similarly formed with a plurality of wishbone shaped struts coupled together. The wishbone shaped struts in ring 804 may all be the same in ring 804 and they may be similarly formed from two oppositely sloped struts that are coupled together with an arcuate strut that forms a protuberance or peak in the wishbone shaped strut at the inflection point between the two oppositely sloped struts. The sizes and angles of the struts in ring 804 may be different than ring 802 since the two rings are concentric with one another and therefore ring 804 has a smaller diameter and circumference than outer ring 802. A plurality of linear struts 812 that extend radially outward from the center of the prosthesis couple rings 802 and 804 together to form closed cells 810. The closed cells 810 formed between ring 802 and 804 may all have the same geometry, or they may vary.

Struts may be wishbone shaped in order to divert stress and strain away from the apex of the wishbone thereby allowing a greater angular range of motion to be achieved for a given maximum strain, or allowing a lower maximum strain to occur for the same given range of motion.

A Y-shaped strut 816 is coupled to the wishbone shaped second ring 804 with the tail of the Y extending radially inward toward the center of the prosthesis, thereby forming a lemon shaped closed cell with a peak and valley on opposite sides of the closed cell, and pointed ends on the two other sides of the closed cell. The Y-shaped strut may also be coupled to the wishbone shaped second ring 804 with the tail of the Y extending radially inward toward the center of the prosthesis to form several tear drop shaped closed cells with pointed ends on opposite side of the tear drop shape. The tails of the Y may be coupled together to define a central aperture 818 in the prosthesis. In this example, the central aperture 818 is star shaped with three pointed arms extending radially outward to form the star shape.

A plurality of inner closed cells 820, here three closed cells 820, are formed by two V-shaped struts 822 on opposite sides of the closed cell 820 coupled to the tails of adjacent Y-shaped struts 816 to form the closed cells 820. Each closed cell 820 contains a commissure tab 806 and two ventricular anchor struts 814.

Commissure tabs 806 may be adjacent the center of the prosthesis and may include a plurality of suture holes so that the prosthetic valve leaflets may be sutured to the commissure tabs. The commissure tabs 806 may be a rectangular shaped strut with a slit through the middle for receiving prosthetic leaflets. In this example there are three prosthetic valve leaflets (not shown) attached to the commissure tabs forming a tricuspid prosthetic valve. The prosthetic valve leaflets are not illustrated for ease in viewing the expandable frame. The commissure tabs are disposed in between struts 814 which form ventricular anchor tabs that anchor the prosthesis to a ventricular portion of the native valve, such as an anterior portion of the native valve (such as the fibrous trigones) and a posterior portion of the native valve. Struts 814 form part of the ventricular anchors. Two struts 814 are disposed on either side of the commissure tabs 806. One end of strut 814 is coupled to a tail of the Y-shaped strut 816, and the opposite end of struts 814 is a free end that may be bent radially outward. The free end may include a through hole which is used for attachment of a cover (not shown) such as suturing. The cover may be any material such as a polymer like Dacron, and forms a foot which is a soft atraumatic tip for engaging tissue. The Dacron or other polymer cover material provides greater surface area and therefore reduces the chance of the ventricular anchor tabs piercing tissue. The ventricular tabs can then angulate away from the valve frame during expansion to allow anchoring on the fibrous trigones or any other anterior portion of the ventricular side of the native valve, or any portion on the posterior annulus of the native valve. The ventricular anchors may also help capture the native valve leaflets between the ventricular anchor and an outer surface of the expandable frame. If the prosthetic valve has ventricular wings or petals (as described below), the native valve leaflets may also be captured by the wings or petals and this may help keep the native valve leaflets out of the flow path. There may be any number of ventricular anchors, but in this example, there are three.

Facing radially inward toward the center of the device may be a plurality of anchor tabs 808, here mushroom head shaped tabs or T-shaped heads, which allow the prosthesis to be coupled to a delivery catheter as will be described below. The anchor tabs 808 are disposed on a portion of strut that joins two tails of Y-shaped struts 816 together. Thus, in this example there are three connection points that may be made with a delivery catheter.

Prosthetic valve 800 also includes arcuate struts 830 which have opposed ends which slope in opposite directions and a curved connector at the inflection point. Here, there are three arcuate struts 830 and each end of the arcuate struts is coupled to the arms of a Y-shaped strut 818 to form petals or wings. The petals or wings form a second ventricular anchor on the ventricular side of the prosthesis as well helping to capture native valve leaflets. The petals or wings may extend downward away from the prosthesis toward the ventricle during delivery and initial deployment and then the petals or wings extend radially outward and away from the anchor in the fully expanded configuration to form a flange circumferentially disposed around the expandable frame that can engage a ventricular portion of the native valve just below the annulus so that the annulus is captured between the petals or wings, and the upper rings. The upper atrial flared region and the lower ventricular wings or petals therefore provide upper and lower shoulders that may act as a clamp that can capture or sandwich the native valve annulus therebetween, providing good purchase of the tissue for anchoring the prosthesis into the native anatomy. Additionally, the ventricular wings or petals also may help capture the native valve leaflets and move them out of the flow passage to ensure optimal valve function. Here, three struts 830 are shown but any number may be used. The ventricular anchors 814 are substantially the same as previously described in FIG. 6A and may be used in conjunction with the petals or wings to further help secure the prosthetic valve to the native valve.

Figure 8C:
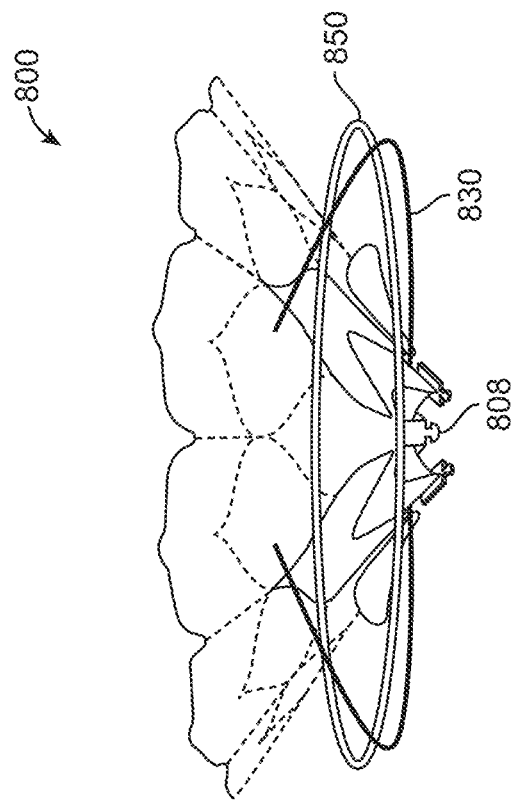
FIG. 8C shows the prosthetic valve of FIG. 8A in a fully deployed configuration.
Figure 8B:
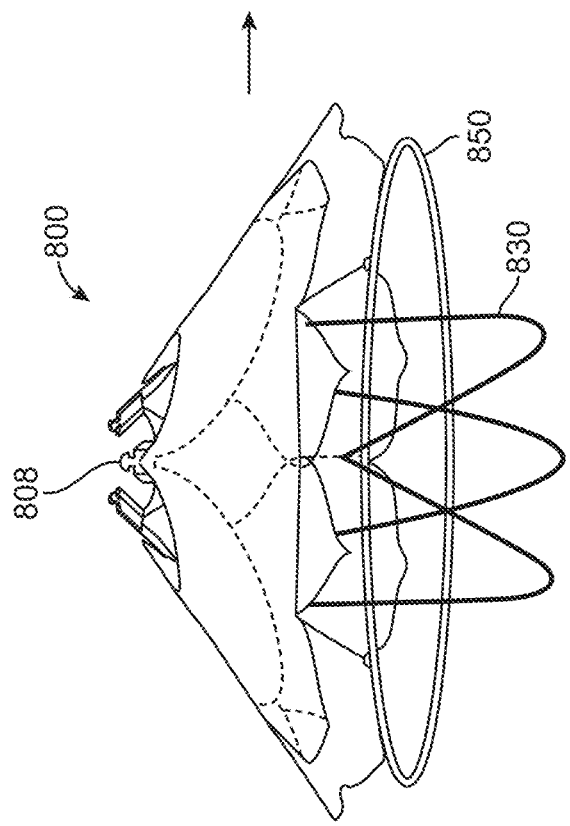
FIG. 8B shows the prosthetic valve of FIG. 8A in a partially deployed configuration.

FIG. 8B illustrates prosthetic valve 800 of FIG. 8A after shape setting and in a partially deployed configuration where the atrial end has expanded into a conical shape with the atrial diameter increasing toward the ventricle to form the cone or flared region. The expanded configuration may be a paraboloid with a concave portion facing downward toward the ventricle, but still disposed above the valve annulus 850. A delivery catheter is not shown for convenience. The petals or wings 830 extend axially downward from the expandable frame and pass through the native valve orifice through the annulus 850. The petals or wings 830 extend substantially parallel with the longitudinal axis of the prosthesis in this partially deployed configuration. A cover (not shown) similar to cover 624 in FIG. 6B may be disposed over the struts 814 and any or all portions of the prosthetic frame to form a foot which helps create the ventricular anchors. The foot may include an enlarged head region and a narrower body. Again, the enlarged head provides a larger surface area and therefore minimizes pressure applied to tissue during anchoring in order to eliminate or reduce tissue trauma. Other aspects of FIG. 8B are the same as FIG. 8A.

FIG. 8C shows the prosthetic valve 800 of FIG. 8B in the fully deployed configuration where the atrial cone has been inverted to now form a paraboloid with the concave portion facing upward toward the atrium but above the annulus 850. The cone can then fit into the native valve and the walls of flared cone prevent the valve from slipping through the native valve orifice. Also, the petals or wings 830 have now radially expanded outward so they are orthogonal or otherwise transverse to the longitudinal axis of the prosthesis to form a flange that can be anchored against a lower surface of the native valve on the ventricular side. Additionally, the prosthetic valve also has ventricular anchors and they are shown extending radially outward to engage with the underside of the annulus, for example on the fibrous trigones on the anterior side of the native valve or on a posterior portion of the native valve. Again, a cover like cover 624 in FIG. 6B may be disposed over the ventricular anchors 814 to form the atraumatic tip of the ventricular anchors. The cover may be Dacron, or another polymer, or any material that has the desired mechanical properties. The cover may have an enlarged head region and a thinner elongate body region. The enlarged head region provided greater surface area in order to reduce contact pressure with tissue during anchoring in order to eliminate or reduce tissue piercing and trauma.

Figure 8D:
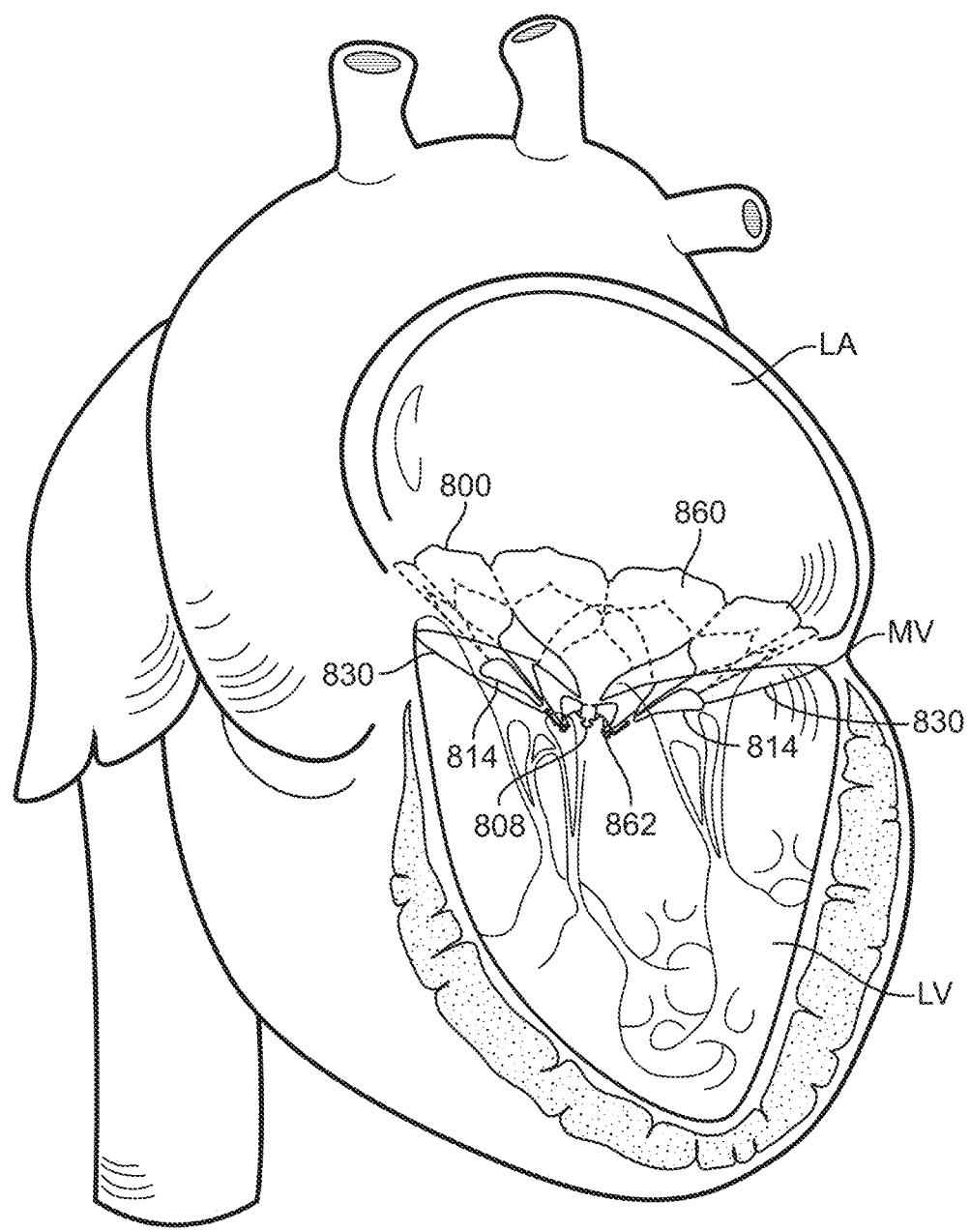
FIG. 8D shows the prosthetic valve of FIG. 8A disposed in a native mitral valve.

FIG. 8D shows the prosthetic valve 800 from FIG. 8A fully deployed in a native mitral valve MV. When fully deployed the larger diameter portion of the flare rests in the left atrium LA and prevents the prosthesis from migrating into the left ventricle LV. Ventricular anchor tabs 814 may include two anterior anchor tabs for anchoring on the fibrous trigones on an anterior portion of the native valve and a posterior anchor tab which anchors on a posterior portion such as a posterior shelf of the native valve. Ventricular wings 830 or petals are also disposed on the ventricular side to further help with anchoring on a ventricular side of the native valve. FIG. 8D is shown with the cover 860 such as Dacron or another polymer, fabric, or tissue coupled to the expandable frame. Prosthetic leaflets 862 are shown attached to the commissure posts. Anchor tabs 808 on the commissure posts are used to releasably couple the prosthesis with a delivery catheter. Here, there are three anchor tabs.

Releasable Coupling with a Delivery Catheter

FIGS. 9A-9F illustrate a delivery catheter which may be used to carry any of the prosthetic valves disclosed herein. The delivery catheter may be releasably coupled to the prosthesis so that once the prosthesis has been correctly positioned and deployed, the prosthetic valve is released from the delivery catheter and left in place while the delivery system is removed from the patient.

Figure 9A:
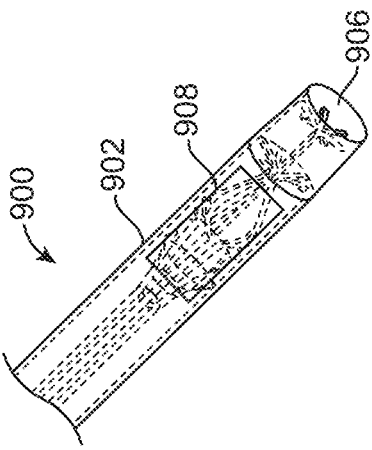
FIG. 9A-9F show a delivery catheter that is releasably coupled to a prosthetic valve.

FIG. 9A shows the outer surface of a delivery catheter 900 which includes an outer sheath 902 and a tapered atraumatic distal tip 904. The tapered atraumatic distal tip 904 may be removed before the prosthetic valve is inserted and expanded.

Figure 9B:
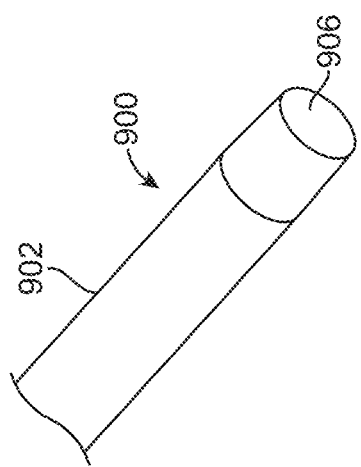

FIG. 9B shows that outer sheath 902 is generally tubular shaft with a single lumen 906 extending through the shaft. The lumen 906 is configured to house any of the prosthetic valves disclosed herein and provide a constraint that keeps the prosthetic valve in the collapsed configuration during delivery.

Figure 9C:
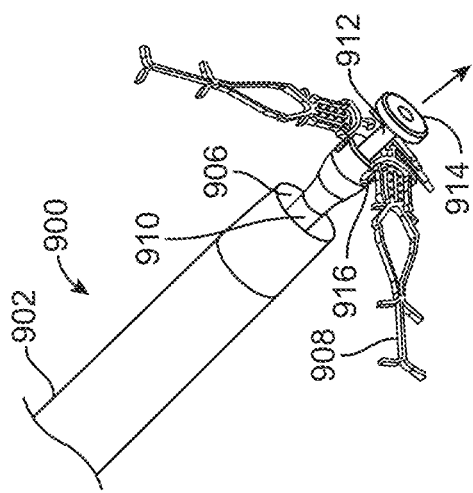

FIG. 9C shows the prosthesis 908 schematically disposed in lumen 906 of outer sheath 902. Prosthesis 908 may be any of the prosthetic valves disclosed herein, and is constrained in a collapsed configuration.

Figure 9D:
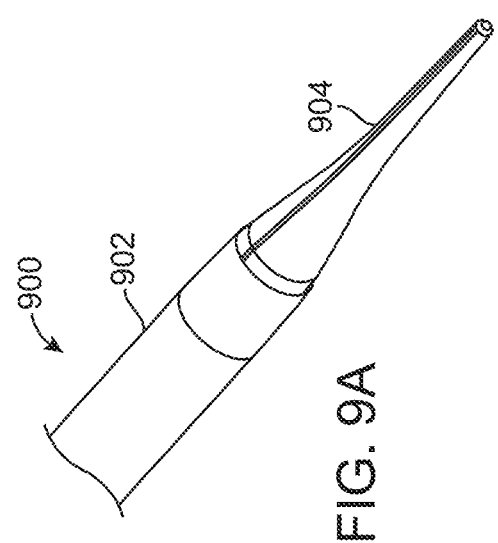

FIG. 9D shows proximal retraction of outer sheath 902 removes a constraint from prosthesis 908 and allows the prosthesis to partially self-expand but the sheath still is disposed over the portion of the prosthesis that is releasably engaged with the delivery catheter and this provides a constraint that prevents the prosthesis from inverting and fully expanding. Here, only the portions of the prosthesis which are releasably coupled to the delivery catheter are illustrated. The rest of the prosthetic valve has been omitted from FIGS. 9D-9F for convenience. As outer sheath 906 is retracted proximally, the prosthesis self-expands to form the partially deployed prosthesis where a paraboloid is formed with a concave portion facing downward toward the ventricle of the patient's heart. Therefore, an inverted cone shape is formed with the small end of the cone facing toward the atrium and the large end of the cone facing downward toward the ventricle. Only the arms of the prosthesis with the connector tabs remain coupled to the delivery catheter. Examples of tabs include the mushroom head shaped tabs or T-shaped tabs previously described above. The prosthesis remains in the atrium above the native valve at this stage of delivery and expansion.

Figure 9E:
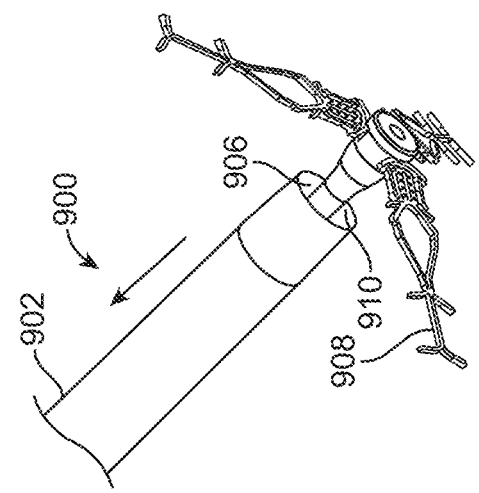

FIG. 9E shows that further proximal retraction of outer sheath 902 (or distal advancement of an intermediate shaft 910 disposed in the lumen 906 of outer sheath 902 allows the prosthetic valve to continue to open up and invert so that the paraboloid faces the opposite direction with the concave portion of the paraboloid facing toward the atrium. The prosthetic valve 908 remains coupled to the delivery catheter 900.

Figure 9F:
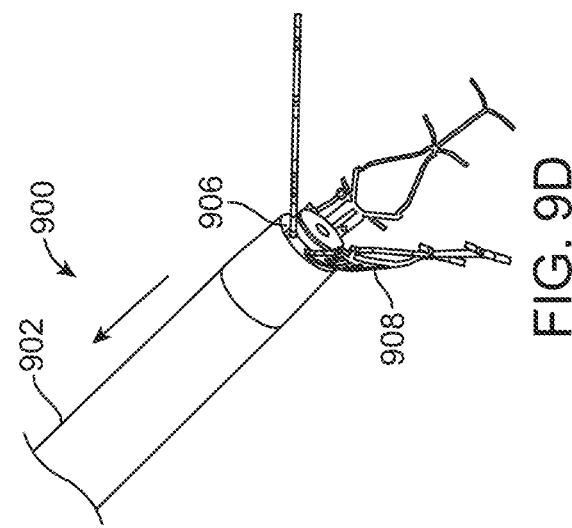

FIG. 9F shows release of the prosthetic valve 908 from the delivery catheter 900 once the prosthetic valve has been correctly positioned and expanded into the native valve. Here, an inner shaft 912 is slidably disposed in a lumen of intermediate shaft 910. As inner shaft 912 is advanced distally a disc or cap 914 is moved away from a hub coupled to the intermediate shaft 910. The hub includes slots 916 which capture the mushroom head or T-shaped head of the prosthesis. So, as the cap 914 moves away from the hub and slots 914, the mushroom head or T-shaped head becomes unconstrained and is free to self-expand out of the slot 914. Once out of the slot, the prosthesis 908 is then detached from the delivery catheter 900. Further details on the coupling mechanism are described below.

In the example of FIGS. 9A-9F, there are only 3 connections between the prosthetic valve and the delivery catheter. Additional connection points may be used such as by adding tabs on the ventricular anchors as seen in FIG. 7A so that there are six connection points. Any number of connection points may be used an any combination of connectors on the commissure or on the ventricular anchors may be used. Moreover, in this example or any example where there are multiple releasable connections between the prosthesis and the delivery catheter, the connections may all be released simultaneously, individually one after another in serial fashion and independently of one another, or in desired groupings, or in stages.

Figure 10C:
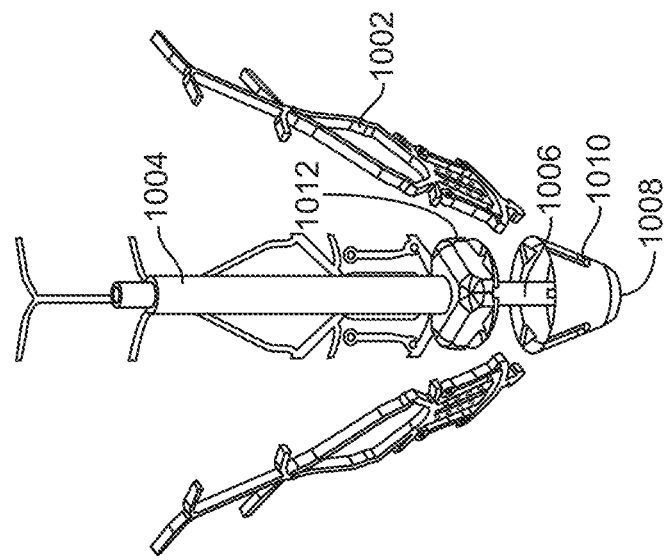
FIGS. 10A-10C show a locking mechanism for releasably coupling a prosthetic valve with a delivery catheter.
Figure 10B:
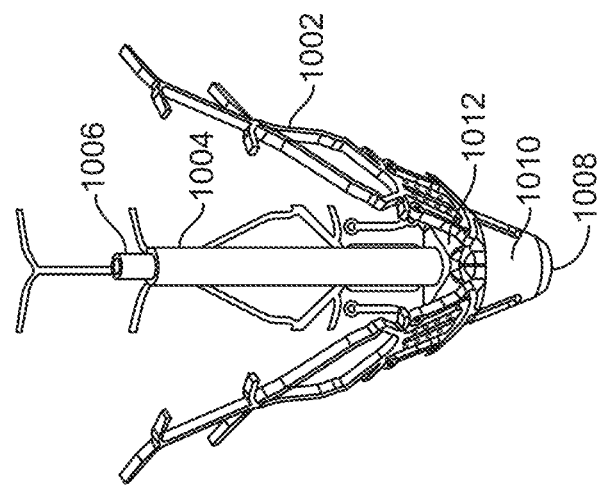
Figure 10A:
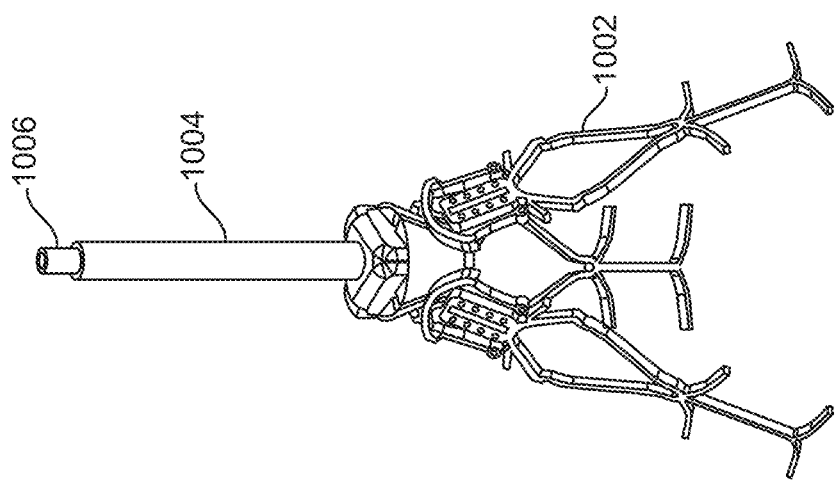

FIGS. 10A-10C show another example of a coupling mechanism that may be used to releasably couple a prosthetic valve with the delivery system. This example is similar to that shown in FIGS. 9A-9F with the major difference being that the slotted region on the hub and the disc or cap are reversed. The outer sheath is omitted from FIGS. 10A-10C for convenience.

In FIG. 10A the delivery catheter includes an inner shaft 1006 and an intermediate shaft 1004 slidably disposed over inner shaft 1006. Prosthetic valve 1002 is releasably coupled to the delivery catheter. Again, only the portions of prosthetic valve coupled to the delivery catheter are shown. The prosthetic valve 1002 may be any of the prosthetic valves disclosed herein. Also, in this view, the prosthesis is partially deployed and expanded to form the paraboloid with the concave portion facing downward toward the ventricle. The paraboloid also may be described as an inverted cone with the small end of the cone facing toward the atrium and the large end of the cone facing downward toward the ventricle.

In FIG. 10B further retraction of an outer sheath (not shown) allows the prosthesis to continue to expand and invert so that the prosthesis forms a cone with the larger diameter end facing toward the atrium and the smaller diameter end facing toward the ventricle. A hub 1008 with slots 1010 is coupled to the inner shaft 1006. The slots 1010 are sized to receive the T-shaped heads or mushroom heads on the prosthesis and hold them when the disc or cap 1012 is apposed with the hub 1008. Disc or cap 1012 is coupled to intermediate shaft 1004.

In FIG. 10C distal advancement of inner shaft 1006 moves hub 1008 away from cap or disc 1012 exposing slots 1010 and allowing the mushroom head or T-shaped heads of the prosthesis to release from the delivery catheter. Or intermediate shaft 1004 may be retracted proximally to separate the disc or cap from the hub, or a combination of proximal retraction of intermediate shaft 1004 and distal advancement inner shaft 1006 may be used to separate the two and release the prosthetic valve from the delivery catheter.

In the example of FIGS. 10A-10C, there are only 3 connections between the prosthetic valve and the delivery catheter. Additional connection points may be used such as by adding tabs on the ventricular anchors as seen in FIG. 7A so that there are six connection points. Any number of connection points may be used an any combination of connectors on the commissure or on the ventricular anchors may be used.

Figure 11:
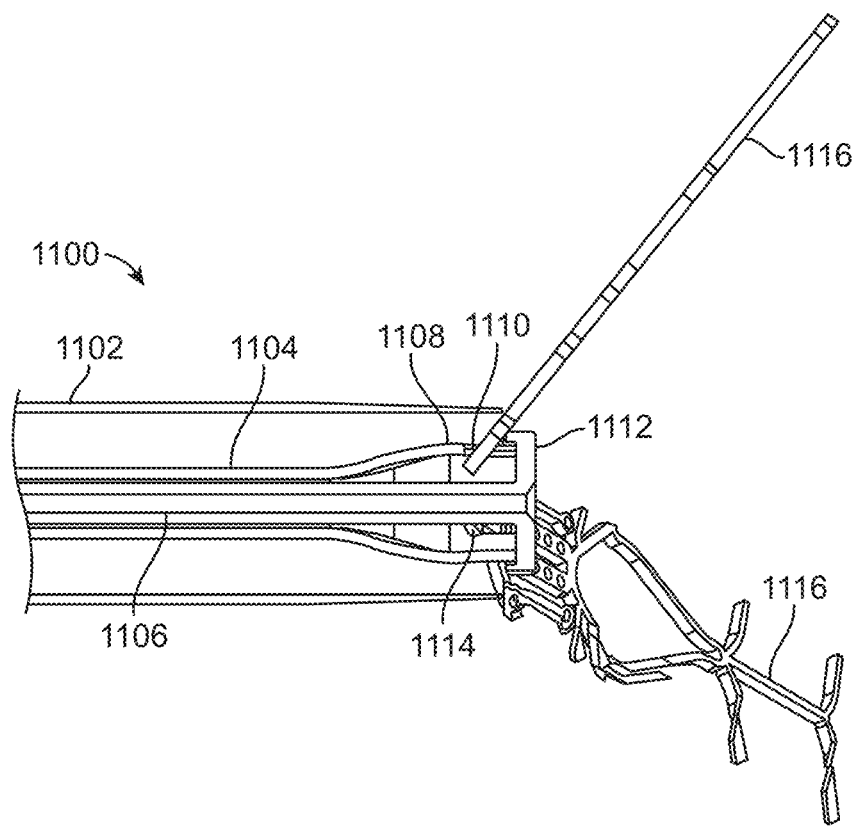
FIG. 11 shows a side view of a locking mechanism for releasably coupling a prosthetic valve with a delivery catheter.

FIG. 11 shows a side view of the releasable connection between a prosthetic valve and a delivery catheter and highlights an example of a locking mechanism that allows the prosthetic valve to be releasably coupled with the delivery catheter.

The delivery catheter 1100 includes an outer sheath 1102 slidably disposed over an intermediate shaft 1104 which is slidably disposed over an inner shaft 1106. All three shafts may move proximally or distally relative to one another. The outer sheath 1102 includes a lumen that houses a prosthetic valve 1116. The prosthetic valve 1116 may be any of the prosthetic valves disclosed herein. This figure only shows the portions of the prosthetic valve that are releasably coupled to the delivery catheter. The rest of the valve has been omitted for convenience. A hub 1108 with slots 1110 is coupled to the intermediate shaft. A cap or disc 1112 is coupled to the inner shaft 1106. Tabs 1114 such as mushroom heads or T-shaped heads may fit in the slots 1110 in the hub and when the cap 1112 is apposed with the hub, the tabs 1114 are captured and thus the prosthetic valve is coupled to the delivery catheter. Once the prosthetic valve is fully deployed and positioned, the inner shaft 1106 may be moved relative to the intermediate shaft 1104 so the cap is moved away from the hub, thereby allowing the tabs 1114 to release from the slots 1110 and decouple the prosthetic valve from the delivery catheter.

FIGS. 12A-12B illustrate another example of a locking mechanism for releasably coupling a prosthetic valve with a delivery catheter.

FIG. 12A shows delivery catheter 1200 which includes an outer sheath (not illustrated) for housing the prosthetic valve, an intermediate shaft 1202 slidably disposed in the outer sheath, and an inner shaft 1210 slidably disposed in the intermediate shaft 1202. A cap 1206 is coupled to the intermediate shaft 1202 and a hub 1208 has pins 1212 extending proximally from the hub and parallel with the longitudinal axis of the delivery catheter 1200. Here, only the arms or portions of the prosthetic valve 1204 that are releasably coupled with the delivery catheter are shown. The prosthetic valve 1204 may be any of the examples disclosed herein, and includes tabs 1214 with an aperture through the tip of the tab. The pins 1212 may be disposed in the apertures to releasably couple the prosthetic valve with the delivery catheter when the cap is apposed with the pins.

FIG. 12B shows release of the prosthetic valve 1204 from the delivery catheter 1200. Here, intermediate shaft 1202 is retracted proximally or inner shaft 1210 is advanced distally, or a combination of both proximal and distal motion of shafts 1202, 1210 move the cap 1206 away from the pins 1212 allowing the apertures 1214 in the connector tabs on the prosthetic valve 1204 to slide off the pins thereby decoupling the prosthetic valve from the delivery catheter.

In any of the examples of locking mechanisms for coupling and decoupling the prosthesis from the delivery catheter, it may be desirable to recapture the prosthetic valve. This may be accomplished any time up until the prosthetic valve is released from the delivery catheter. Thus, if the prosthesis requires repositioning or for some other reason the physician decides not to implant the prosthesis, the operator may allow the prosthesis to return to its unbiased shape of being concave facing downstream and the prosthesis may be resheathed and constrained in its collapsed configuration. Once it is repositioned or a decision is made to deploy the prosthesis, the deployment procedure may be recommenced.

Delivery Method

FIGS. 13A-13D illustrate an example of a method of delivering a prosthetic valve to a mitral valve in a patient.

Figure 13A:
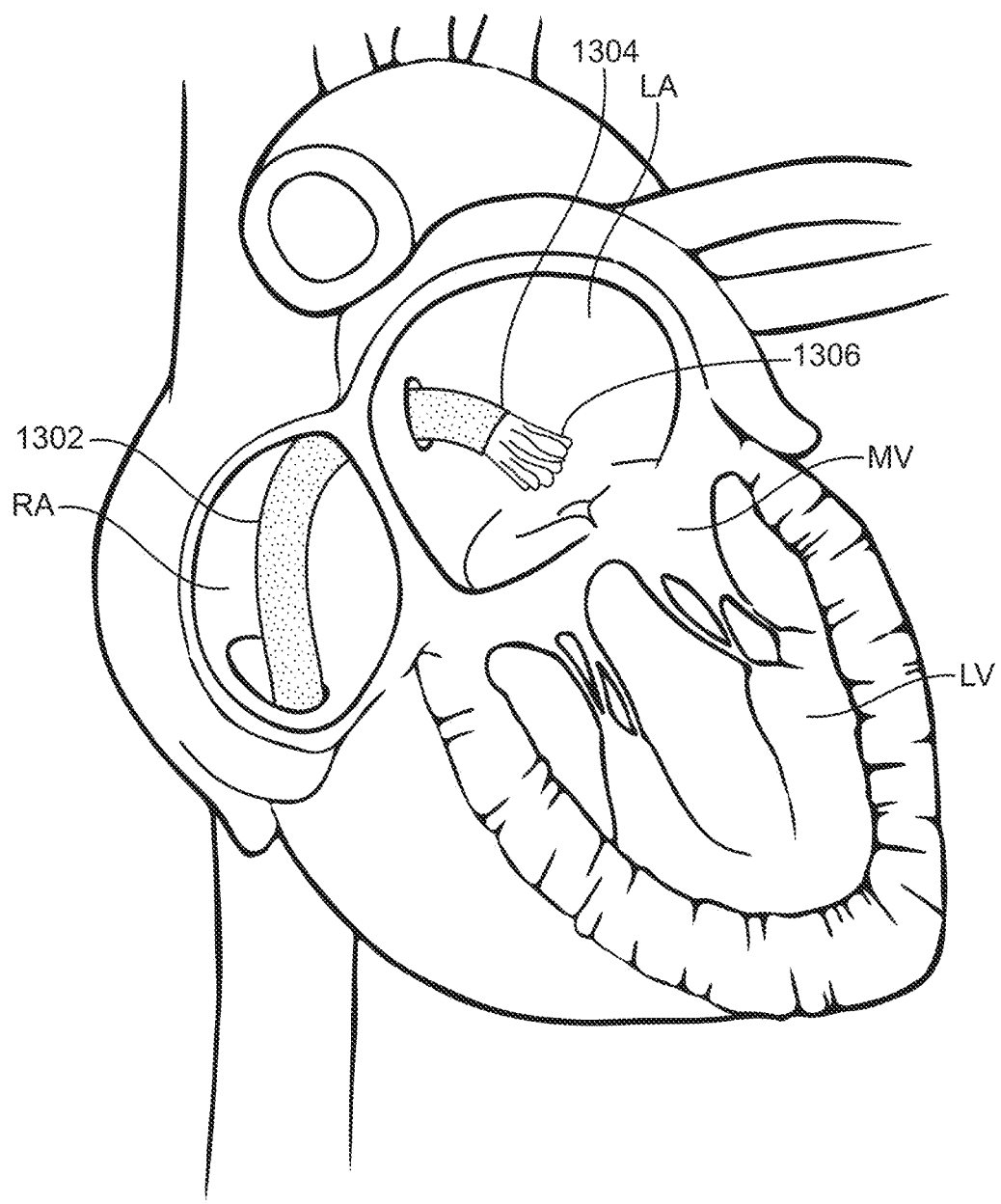
FIGS. 13A-13D illustrate an example of a method for deploying a prosthetic valve in a native valve.

In FIG. 13A, a sheath 1302 is introduced into the patient's heart using techniques known in the art such as percutaneously through a vein in the groin or via a cutdown, and over a guidewire. The sheath 1302 is advanced transseptally across the septal wall from the right atrium RA to the left atrium LA. A delivery catheter 1304 carrying a prosthetic valve 1306 such as any of the prosthetic valves described herein, is advanced through the sheath 1302 into the left atrium. The distal tip of the delivery catheter is positioned or steered so that it is adjacent the native mitral valve MV. The sheath may be proximally retracted or the delivery catheter advanced distally past the sheath to partially expose the prosthetic valve 1306.

Figure 13B:
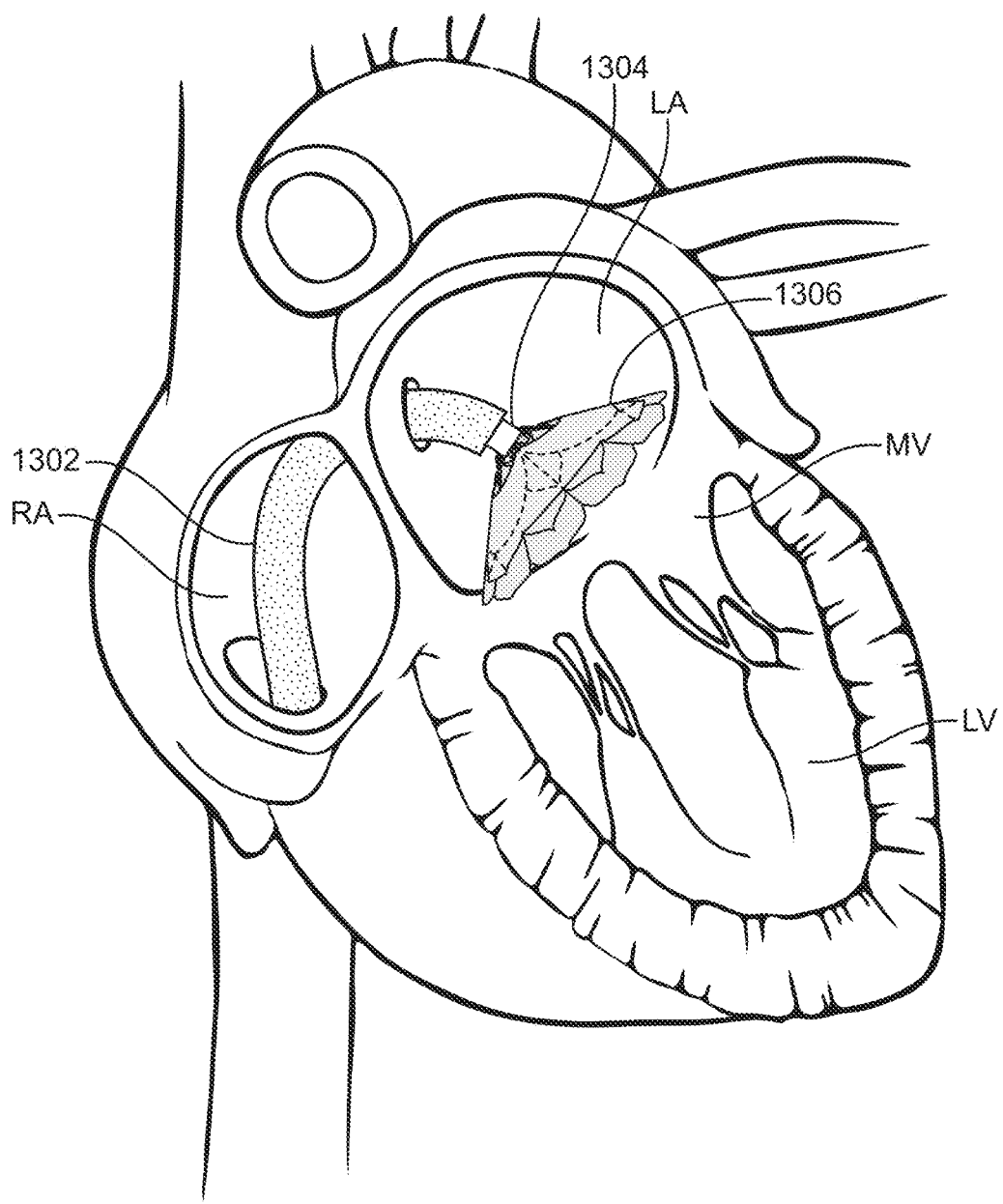

FIG. 13B the sheath is removed from the prosthetic valve 1306 thereby removing a constraint and allowing the prosthetic valve 1306 to expand into an intermediate configuration. The intermediate configuration is a cone shape or paraboloid with the concave surface facing downward toward the ventricle. The small diameter portion of the cone is facing the left atrium and the larger diameter portion of the cone faces the ventricle. The prosthetic valve is still coupled to the delivery catheter and disposed in the left atrium LA above the mitral valve MV.

Figure 13C:
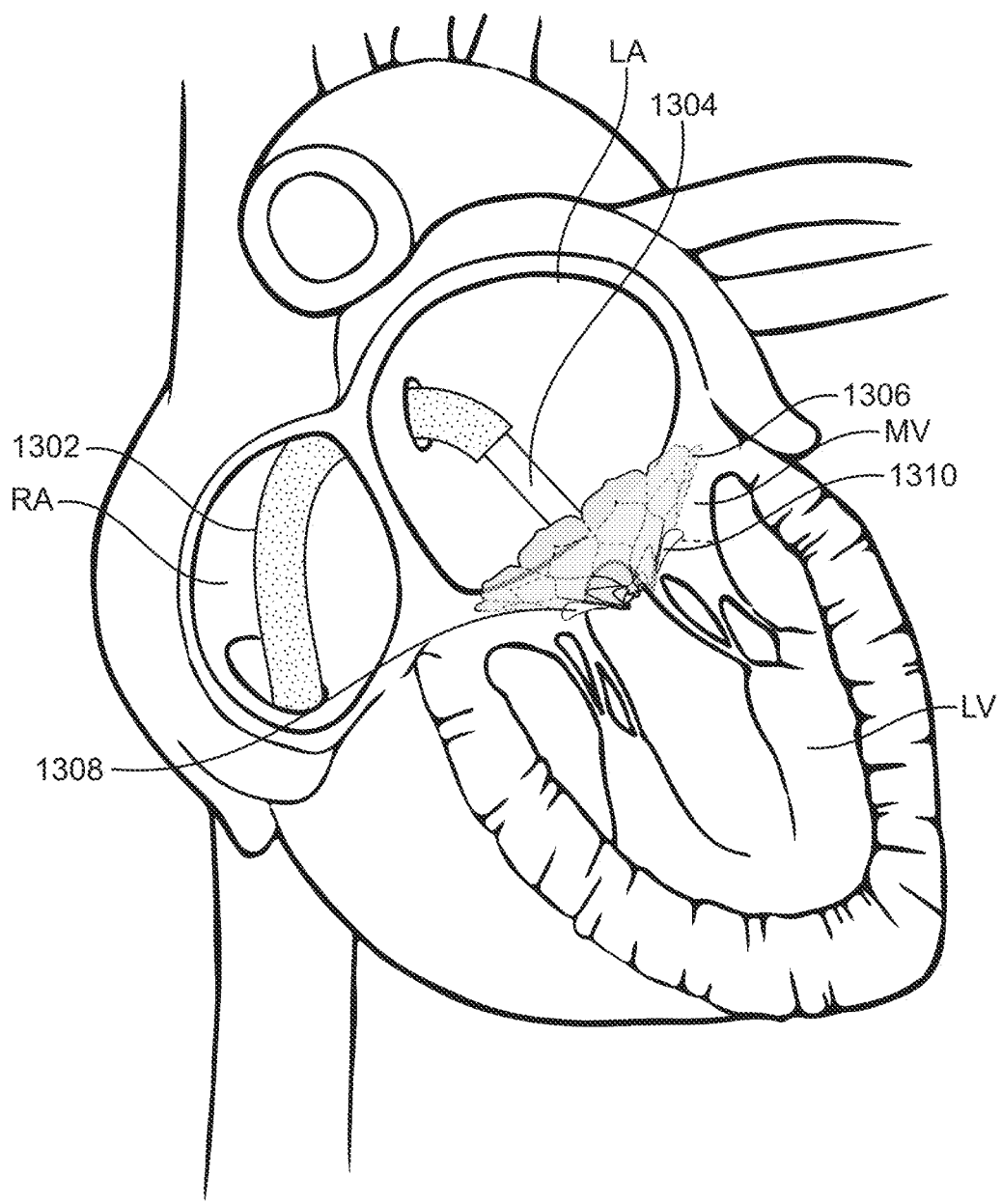

In FIG. 13C further expansion of the prosthetic valve 1306 and optionally with distal pressure applied to the prosthesis against the mitral valve MV, the prosthesis 1306 inverts so that the cone now has its large diameter portion facing the left atrium LA and the smaller diameter portion faces toward the left ventricle LV. The cone may be a paraboloid shape with the concave portion facing toward the left atrium LA and the convex portion facing toward the left ventricle. The ventricular anchor tabs also expand radially outward to engage a ventricular portion of the native valve. For example, the prosthetic valve may have two anterior ventricular anchors 1308 that engage the fibrous trigones on the anterior portion of the native mitral valve and a posterior ventricular anchor 1310 that engages a posterior portion of the native valve on the ventricular side. If the posterior portion has an annular posterior shelf region, the posterior ventricular anchor may land there.

Figure 13D:
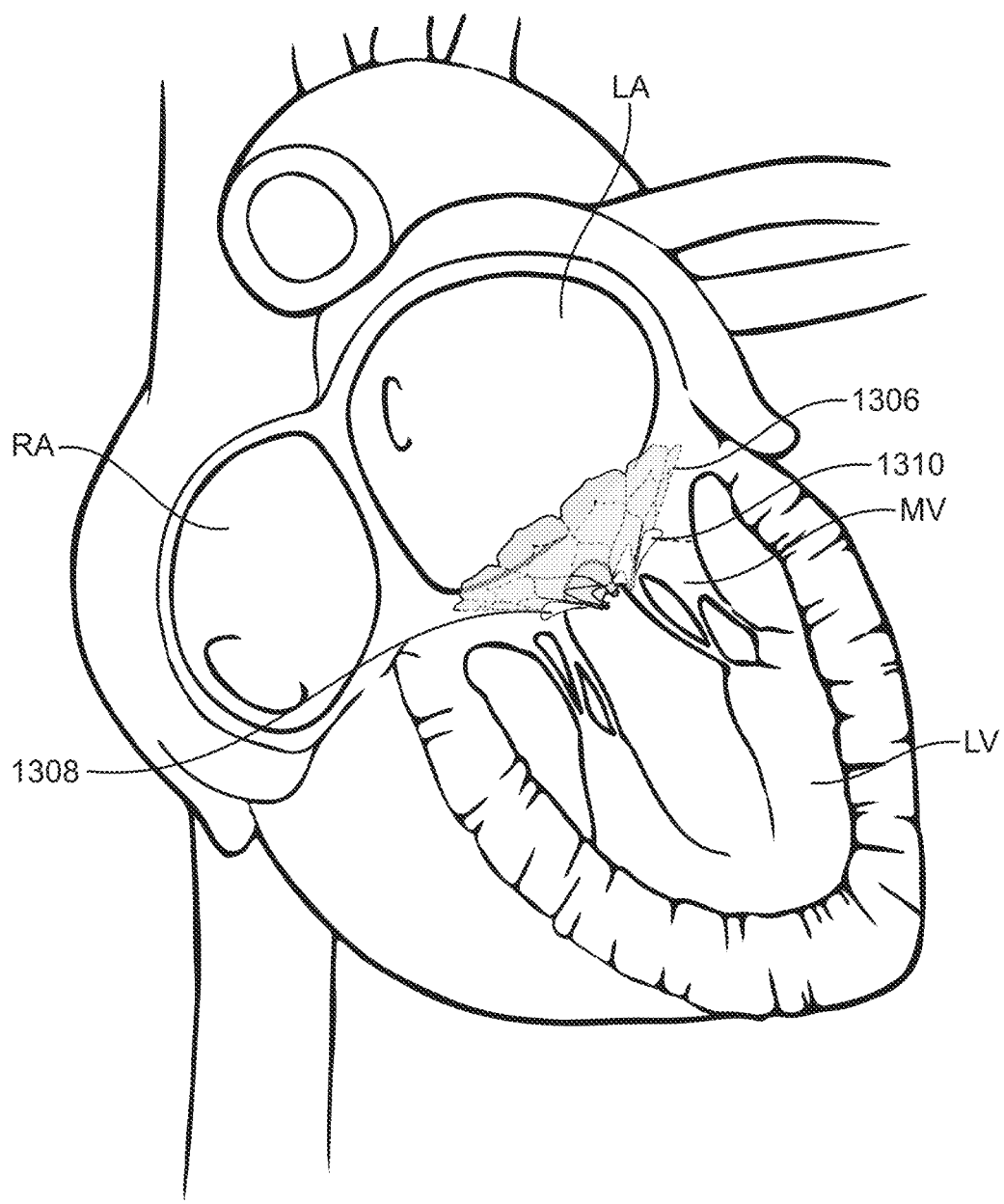

In FIG. 13D the prosthetic valve 1306 is fully deployed and anchored into the native valve and the delivery catheter and sheath have been removed from the patient.

Figure 14:
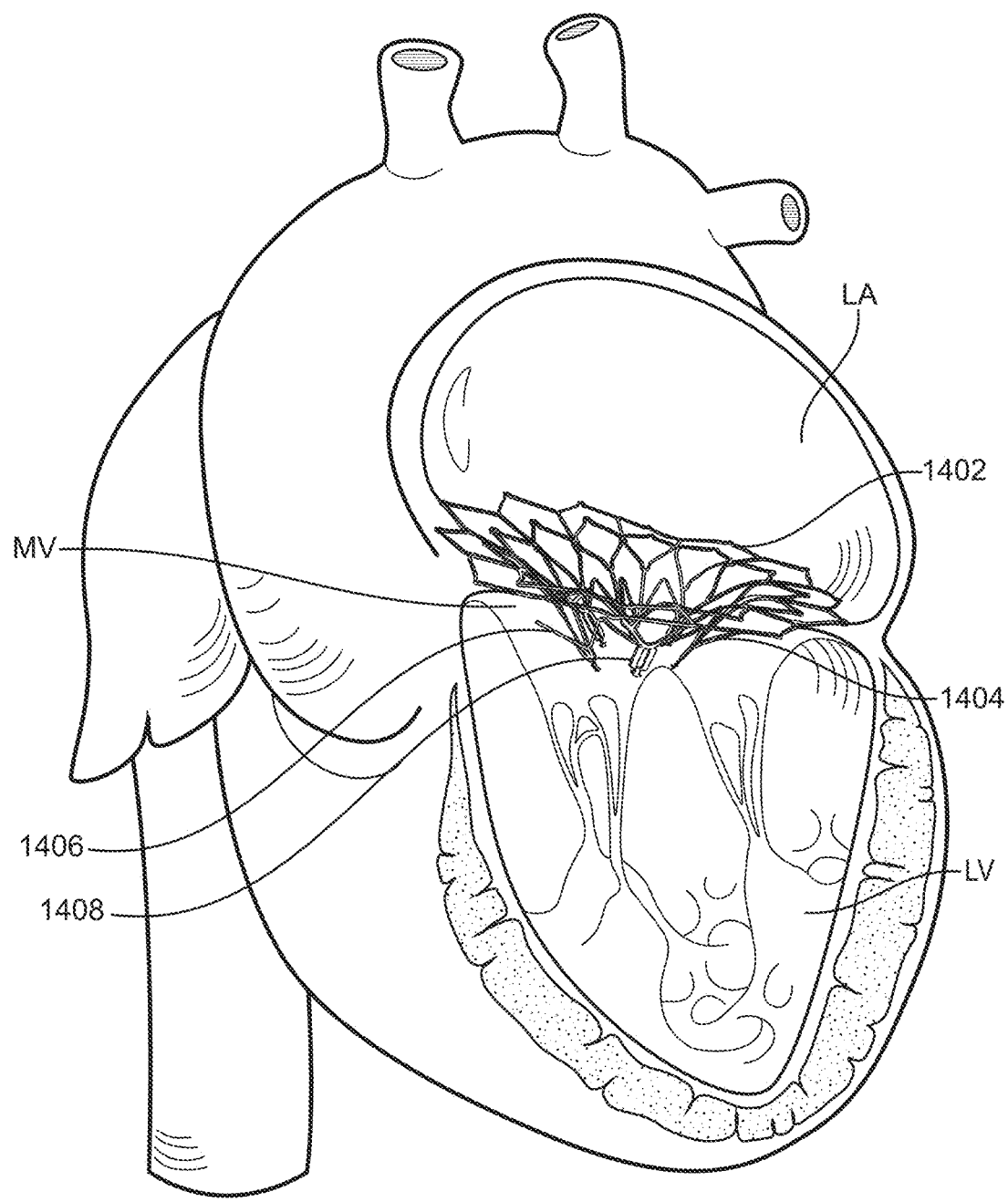
FIG. 14 shows an example of a prosthetic valve in a native valve.

FIG. 14 shows a prosthetic valve 1402 disposed in a native mitral valve MV. When fully deployed the larger diameter portion of the cone rests in the left atrium LA and prevents the prosthesis from migrating into the left ventricle. Ventricular anchor tabs may include two anterior anchor tabs 1406 for anchoring on the fibrous trigones on an anterior portion of the native valve and a posterior anchor tab 1404 which anchors on a posterior portion such as a posterior shelf of the native valve. FIG. 14 is shown without a cover and without the prosthetic leaflets in order to show the struts of the ventricular anchor tabs 1404, 1406 and the commissure tabs 1408. In this example all three ventricular anchors and all three commissure tabs include anchor tabs for releasable coupling with a delivery catheter such as those previously described.

FIGS. 15A-15D illustrate another example of deployment of a prosthetic valve such as the example in FIGS. 8A-8C.

Figure 15A:
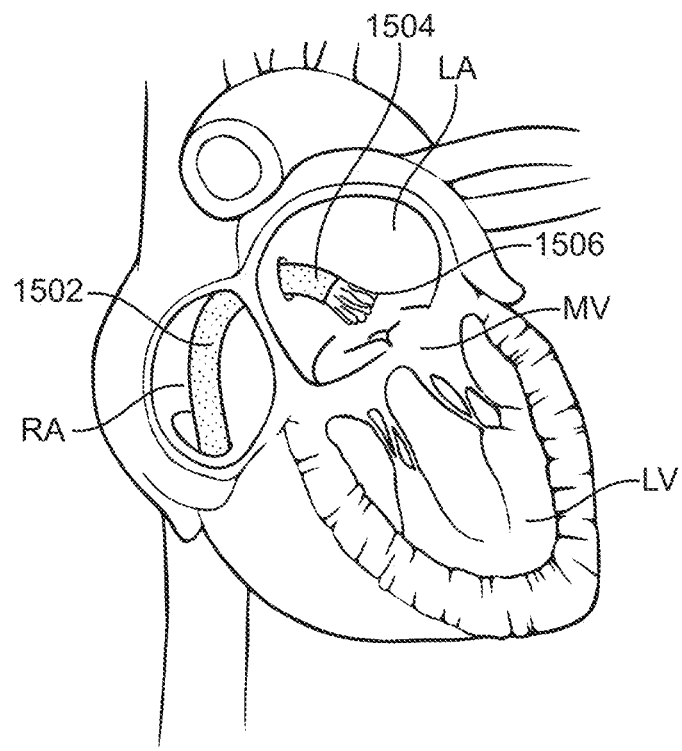
FIGS. 15A-15D show another example of a method for deploying a prosthetic valve in a native valve.

In FIG. 15A, a sheath 1502 is introduced into the patient's heart using techniques known in the art such as percutaneously through a vein in the groin or via a cutdown, and over a guidewire. The sheath 1502 is advanced transseptally across the septal wall from the right atrium RA to the left atrium LA. A delivery catheter 1504 carrying a prosthetic valve 1506 such as the valve in FIGS. 8A-8C is advanced through the sheath 1502 into the left atrium. The distal tip of the delivery catheter is positioned or steered so that it is adjacent the native mitral valve MV. The sheath may be proximally retracted, or the delivery catheter advanced distally past the sheath to partially expose the prosthetic valve 1506.

Figure 15B:
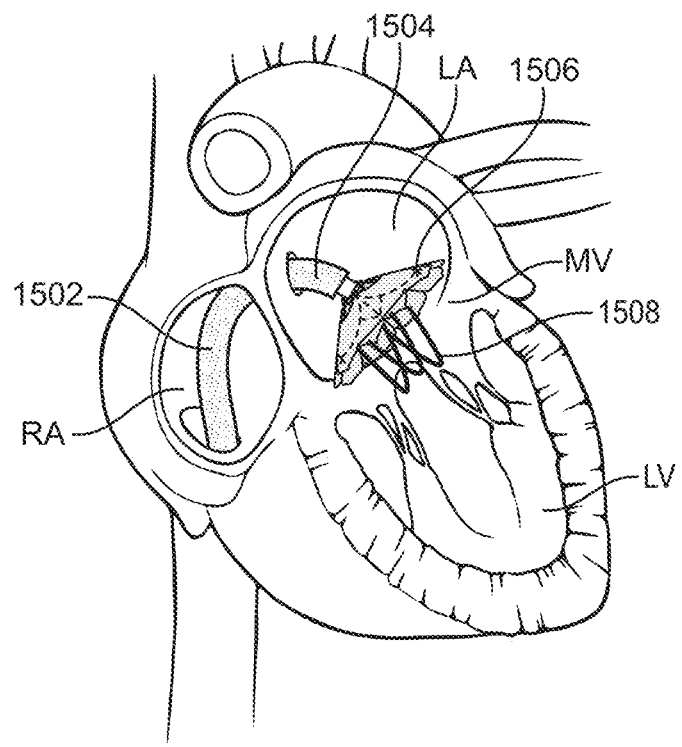

FIG. 15B the sheath is removed from the prosthetic valve 1506 thereby removing a constraint and allowing the prosthetic valve 1506 to expand into an intermediate configuration. The intermediate configuration is a cone shape or paraboloid with the concave surface facing downward toward the ventricle. The small diameter portion of the cone is facing the left atrium and the larger diameter portion of the cone faces the ventricle. The prosthetic valve is still coupled to the delivery catheter and disposed in the left atrium LA above the mitral valve MV. Wings or petals 1508 extend axially downward from prosthetic valve 1506 and may be substantially parallel with the longitudinal axis of the prosthetic valve. The wings or petals pass through the orifice of the native valve.

Figure 15C:
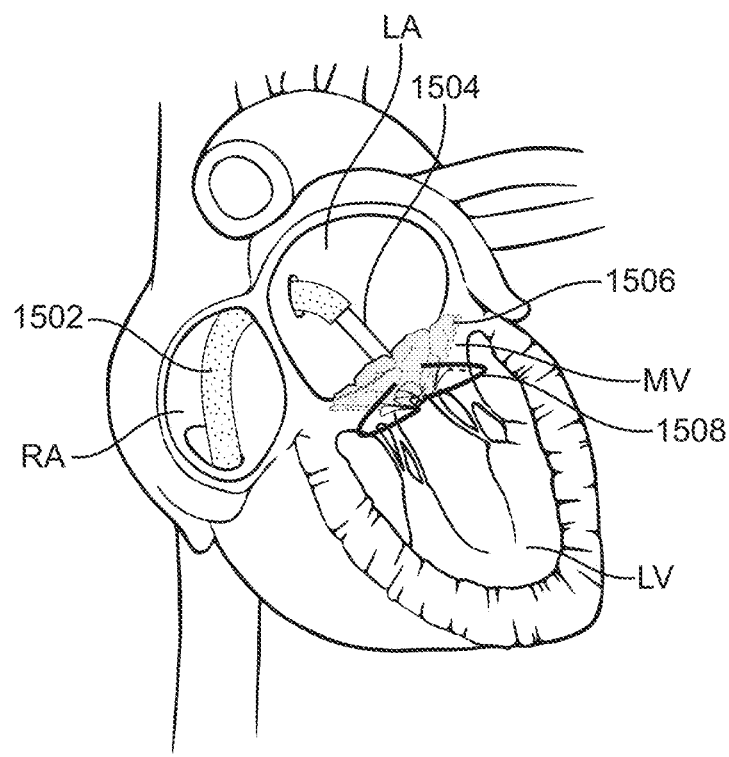

In FIG. 15C further expansion of the prosthetic valve 1506 and optionally with distal pressure applied to the prosthesis against the mitral valve MV, the prosthesis 1506 inverts so that the cone now has its large diameter portion facing the left atrium LA and the smaller diameter portion faces toward the left ventricle LV. The cone may be a paraboloid shape with the concave portion facing toward the left atrium LA and the convex portion facing toward the left ventricle. The ventricular anchor tabs if present, also expand radially outward to engage a ventricular portion of the native valve. For example, the prosthetic valve may have two anterior ventricular anchors that engage the fibrous trigones on the anterior portion of the native mitral valve and a posterior ventricular anchor that engages a posterior portion of the native valve on the ventricular side. If the posterior portion has an annular posterior shelf region, the posterior ventricular anchor may land there. The wings or petals 1508 expand radially outward so they are perpendicular or otherwise transverse to the longitudinal axis of the prosthesis to form a lower flange that can engage the bottom of the mitral valve on the ventricular surface to further anchor the device and also to help capture the native leaflets.

Figure 15D:
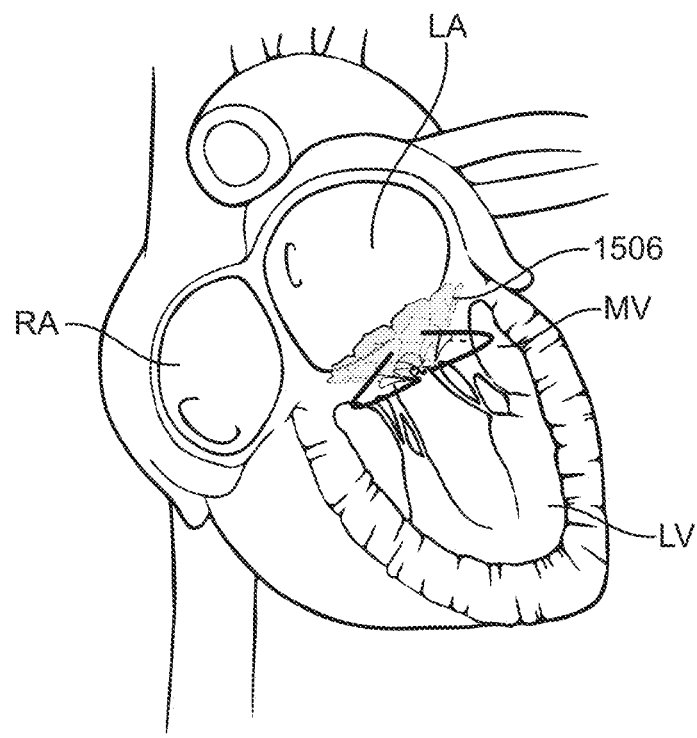

In FIG. 15D the prosthetic valve 1506 is fully deployed and anchored into the native valve and the delivery catheter and sheath have been removed from the patient.

Covering

Many of the figures illustrate only the expandable prosthetic valve frame without the prosthetic valve leaflets attached and also without a cover attached to the frame. However, as discussed above, a cover such as tissue, a polymer or fabric may be applied to the ventricular anchors to help form a foot that can engage tissue in the native valve without piercing or causing trauma to the tissue.

Additionally, in any of the examples disclosed herein, a cover may be applied to all of the frame or portions of the frame. The cover may be a fabric such as Dacron, or tissue such as pericardial tissue, or any other biocompatible material. The cover may be applied to the frame to prevent perivalvar leakage around the frame, as well as promoting tissue ingrowth to help further anchor and secure the prosthesis to the native anatomy. For example, the cover may be applied to the conical flange that rests against the atrial floor, or it may be applied to the ventricular flange that rests against the ventricular portion of the annulus, or the cover may be applied to both. The entire frame may be covered, or only portions covered.

Also, as discussed, the examples generally do not illustrate the prosthetic valve leaflets attached to the prosthetic valve frame for convenience. However, prosthetic valve leaflets are known in the art and commonly two or three prosthetic leaflets may be applied to the frame to form either a bicuspid or tricuspid prosthetic valve. Of course, any number of leaflets may be used such as a single prosthetic leaflet, or four leaflets or more than four leaflets. The prosthetic valve leaflets may be tissue such as pericardial tissue, or they me fabric, a polymer, or other materials known in the art.

Notes and Examples

The following, non-limiting examples, detail certain aspects of the present subject matter to solve the challenges and provide the benefits discussed herein, among others.

In Example 1 a low-profile prosthetic valve for treating a native valve in a patient comprises: a radially expandable frame having an expanded configuration, a collapsed configuration, an atrial end and a ventricular end, wherein in the collapsed configuration the expandable frame is sized and shaped for minimally invasive delivery to the native valve, wherein in the expanded configuration the expandable frame is configured to engage the native valve, wherein the atrial end forms a flared shape in the expanded configuration, and is configured to engage an atrial surface of the native valve, wherein the flared shape flares downward toward a ventricle of the native valve when initially expanded followed by inversion of the flared shape to form a tapered shape tapering toward the ventricle and flaring toward an atrium of the native valve when fully expanded; and a plurality of prosthetic valve leaflets having a free end and an opposite end coupled to an inner portion of the expandable frame, an open configuration and closed configuration, wherein the open configuration the free ends of the plurality of prosthetic valve leaflets are disposed away from one another relative thereby forming an aperture through which fluid flows in an antegrade direction, and wherein in the closed configuration the free ends are disposed closer together than in the open configuration thereby substantially closing the aperture and preventing the fluid from flowing therethrough in a retrograde direction.

Example 2 is the prosthetic valve of Example 1, further comprising a plurality of commissure posts each having a free end and an opposite end, the opposite end coupled to the expandable frame, the free end facing the ventricle when the expandable frame is in the expanded configuration, and wherein the plurality of prosthetic valve leaflets are coupled to the plurality of commissure posts.

Example 3 is the prosthetic valve of any of Examples 1-2, wherein the free end comprises a plurality of apertures extending therethrough, the plurality of apertures sized to receive a suture filament that secures the plurality of prosthetic valve leaflets to the plurality of commissure posts.

Example 4 is the prosthetic valve of any of Examples 1-3, wherein the plurality of commissure posts each have a locking tab coupled to the free end, the locking tab configured to releasably couple the prosthetic valve with a delivery catheter.

Example 5 is the prosthetic valve of any of Examples 1-4, further comprising a plurality of ventricular anchors coupled to the ventricular end of the expandable frame, the ventricular anchors extending radially outward from the expandable frame in the expanded configuration, and configured to engage a ventricular side of the native valve.

Example 6 is the prosthetic valve of any of Examples 1-5, wherein at least one of the plurality of ventricular anchors and at least one of the plurality of commissure posts are disposed in a common closed cell in the expandable frame that is bounded by a plurality of struts.

Example 7 is the prosthetic valve of any of Examples 1-6, wherein the plurality of ventricular anchors each comprise a locking tab coupled to an inferior portion of the ventricular anchor, the locking tab on the ventricular anchor configured to releasably couple the prosthetic valve with a delivery catheter.

Example 8 is the prosthetic valve of any of Examples 1-7, wherein the plurality of ventricular anchors comprise an anterior ventricular anchor configured to engage a fibrous trigone on an anterior portion of a native mitral valve in the native heart, and a posterior ventricular anchor configured to engage a posterior portion of an annulus of the mitral valve or a posterior ventricular portion of the native valve.

Example 9 is the prosthetic valve of any of Examples 1-8, wherein the plurality of ventricular anchors comprise a cover element disposed over at least two struts coupled to the expandable frame.

Example 10 is the prosthetic valve of any of Examples 1-9, wherein the plurality of ventricular anchors comprise a V-shaped strut coupled to the expandable frame, wherein an apex of the V-shaped strut is configured to engage tissue, the prosthetic valve further comprising a cover element disposed over the V-shaped strut.

Example 11 is the prosthetic valve of any of Examples 1-10, wherein the expandable frame comprises a plurality of annular rings coupled together to form a paraboloidal shape.

Example 12 is the prosthetic valve of any of Examples 1-11, wherein the plurality of annular rings comprises a plurality of concentric rings having decreasing diameter coupled together.

Example 13 is the prosthetic valve of any of Examples 1-12, wherein adjacent annular rings are coupled together to form a plurality of closed cells extending circumferentially around the expandable frame.

Example 14 is the prosthetic valve of any of Examples 1-13, further comprising a plurality of ventricular wings on the ventricular end, wherein the plurality of ventricular wings has an expanded configuration and a collapsed configuration, wherein in the collapsed configuration the plurality of ventricular wings are substantially parallel with a longitudinal axis of the prosthetic valve, and wherein the expanded configuration the plurality of ventricular wings extend radially outward from the longitudinal axis to form a flange configured to engage a ventricular surface of the native valve.

Example 15 is a low-profile prosthetic valve system for treating a native valve in a patient, said system comprising: the prosthetic valve of any of Examples 1-14; and a delivery catheter releasably coupled to the prosthetic valve, the delivery catheter configured to deliver the prosthetic valve to the native valve.

Example 16 is the system of Example 15, wherein the delivery catheter comprises a locking element for releasably engaging the prosthetic valve.

Example 17 is a method for delivering a prosthetic valve to a native valve in a heart of a patient, said method comprising: providing a delivery catheter carrying the prosthetic valve; positioning the prosthetic valve adjacent the native valve; partially deploying the prosthetic valve so the prosthetic valve forms a flared shape disposed above the native valve and flaring toward a ventricle of the heart; inverting the flared shape so the initial flared shape becomes a tapered shape disposed above the native valve and tapering toward the ventricle; radially expanding a plurality of ventricular anchors or ventricular wings on a ventricular end of the prosthetic valve to engage a ventricular surface of the native valve; and releasing the prosthetic valve from the delivery catheter.

Example 18 is the method of Example 17, wherein radially expanding the plurality of ventricular anchors or ventricular wings comprises anchoring at least some of the plurality of ventricular anchors on a fibrous trigone of the native valve or a posterior ventricular portion of the native valve.

Example 19 is the method of any of Examples 17-18, wherein radially expanding the plurality of ventricular anchors or ventricular wings comprises radially expanding a plurality of ventricular wings from a position substantially parallel with a longitudinal axis of the prosthetic valve to a position extending radially outward from the longitudinal axis, and engaging the plurality of ventricular wings with a ventricular surface of the native valve.

Example 20 is the method of any of Examples 17-19, further comprising reducing or eliminating regurgitation across the prosthetic valve.

Example 21 is the method of any of Examples 17-20, wherein the native valve is a mitral valve.

Example 22 is the method of any of Examples 17-21, wherein releasing the prosthetic valve from the delivery catheter comprises disengaging a plurality of commissure posts on the prosthetic valve from the delivery catheter.

Example 23 is the method of any of Examples 17-22, wherein releasing the prosthetic valve from the delivery catheter comprises disengaging a plurality of locking tabs on the plurality of ventricular anchors from the delivery catheter.

In Example 24, the apparatuses or methods of any one or any combination of Examples 1-23 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A method for delivering a prosthetic valve to a native valve in a heart of a patient, said method comprising:
   providing a delivery catheter carrying the prosthetic valve;
   positioning the prosthetic valve adjacent the native valve;
   partially deploying the prosthetic valve so the prosthetic valve forms a flared shape disposed above the native valve and flaring toward a ventricle of the heart;
   inverting the flared shape so the initial flared shape becomes a tapered shape disposed above the native valve contacting the native valve, and tapering toward the ventricle;
   radially expanding a plurality of ventricular anchors or ventricular wings on a ventricular end of the prosthetic valve to engage a ventricular surface of the native valve; and
   releasing the prosthetic valve from the delivery catheter.

2. The method of claim 1, wherein radially expanding the plurality of ventricular anchors or ventricular wings comprises anchoring at least some of the plurality of ventricular anchors on a fibrous trigone of the native valve or a posterior ventricular portion of the native valve.

3. The method of claim 1, wherein radially expanding the plurality of ventricular anchors or ventricular wings comprises radially expanding a plurality of ventricular wings from a position substantially parallel with a longitudinal axis of the prosthetic valve to a position extending radially outward from the longitudinal axis, and engaging the plurality of ventricular wings with a ventricular surface of the native valve.

4. The method of claim 3, wherein each of the plurality of ventricular wings comprises:
   a first opposed end;
   a second opposed end; and
   a curved connector connecting the first and second opposed ends;
   wherein each of the plurality of ventricular wings is attached to the prosthetic valve proximate the first and second opposed ends.

5. The method of claim 4, wherein in the flared shape, each of the first and second opposed ends are closer together as compared to in the tapered shape.

6. The method of claim 4, wherein each of the curved connectors is radially expand from the flared shape to the tapered shape.

7. The method of claim 4, wherein:
   in the flared shape, each of the plurality of ventricular wings are inside the prosthetic valve; and
   in the tapered shape each of the plurality of ventricular wings are outside the prosthetic valve.

8. The method of claim 4, wherein:
   in the flared shape, each of the plurality of ventricular wings are disposed inside an annular ring attached to the prosthetic valve; and
   in the tapered shape each of the plurality of ventricular wings are positioned against the annular ring.

9. The method of claim 8, wherein in the tapered shape, each of the plurality of ventricular wings forms a flange pivotable against the annular ring.

10. The method of claim 3, wherein the first and second opposed ends are attached to a Y-shaped strut of the prosthetic valve.

11. The method of claim 10, wherein the Y-shaped strut comprises first, second and third prongs and each of the plurality of ventricular wings is attached to two of the first, second and third prongs of the Y-shaped strut.

12. The method of claim 3, wherein in both the flared shape and tapered shape each of the plurality of ventricular wings is out of plane with the prosthetic valve.

13. The method of claim 3, wherein the plurality of ventricular wings consists of three ventricular wings.

14. The method of claim 1, further comprising reducing or eliminating regurgitation across the prosthetic valve.

15. The method of claim 1, wherein the native valve is a mitral valve.

16. The method of claim 1, wherein releasing the prosthetic valve from the delivery catheter comprises disengaging a plurality of commissure posts on the prosthetic valve from the delivery catheter.

17. The method of claim 1, wherein releasing the prosthetic valve from the delivery catheter comprises disengaging a plurality of locking tabs on the plurality of ventricular anchors from the delivery catheter.

18. The method of claim 1, wherein the tapered shape engages an atrial surface of the native valve.

* * * * *

UNITED STATES PATENT AND TRADEMARK OFFICE
CERTIFICATE OF CORRECTION

| | |
|---|---|
| PATENT NO. | : 11,311,376 B2 |
| APPLICATION NO. | : 16/906782 |
| DATED | : April 26, 2022 |
| INVENTOR(S) | : Fung et al. |

It is certified that error appears in the above-identified patent and that said Letters Patent is hereby corrected as shown below:

On the Title Page

Item (73), in "Assignee", in Column 1, Line 1, delete "Neovase" and insert --Neovasc-- therefor In the Specification In Column 1, Line 49, after "6A", insert --.--

In Column 4, Line 54, after "614", insert --.--

In Column 5, Line 63, delete "parabaloidal-like" and insert --paraboloidal-like-- therefor In Column 6, Line 3, delete "parabaloid" and insert --paraboloid-- therefor In Column 8, Line 27, delete "parabaloidal-like" and insert --paraboloidal-like-- therefor In Column 10, Line 30, delete "818" and insert --816-- therefor In Column 12, Line 17, delete "906" and insert --902-- therefor In the Claims In Column 20, Line 22, in Claim 1, after "valve", insert --,--

Signed and Sealed this
Twelfth Day of July, 2022

Katherine Kelly Vidal
*Director of the United States Patent and Trademark Office*